US012637697B2

(12) United States Patent (10) Patent No.: US 12,637,697 B2
Zhang et al. (45) Date of Patent: May 26, 2026

(54) COMPOSITIONS AND METHODS FOR GENERATING PHYSIOLOGICAL X CHROMOSOME INACTIVATION

(71) Applicant: Children's Medical Center Corporation, Boston, MA (US)

(72) Inventors: Yi Zhang, Boston, MA (US); Azusa Inoue, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 763 days.

(21) Appl. No.: 17/260,283

(22) PCT Filed: Jul. 19, 2018

(86) PCT No.: PCT/US2018/042890
§ 371 (c)(1),
(2) Date: Jan. 14, 2021

(87) PCT Pub. No.: WO2020/018106
PCT Pub. Date: Jan. 23, 2020

(65) Prior Publication Data
US 2021/0292793 A1 Sep. 23, 2021

(51) Int. Cl.
*C12N 15/877* (2010.01)
*A01K 67/0278* (2024.01)
*A61K 38/44* (2006.01)

(52) U.S. Cl.
CPC ...... *C12N 15/8775* (2013.01); *A01K 67/0278* (2013.01); *A61K 38/443* (2013.01); *A01K 2207/05* (2013.01); *A01K 2227/105* (2013.01); *C12Y 114/11027* (2013.01)

(58) Field of Classification Search
None
See application file for complete search history.

(56) References Cited

U.S. PATENT DOCUMENTS

| | | | |
|---|---|---|---|
| 4,441,972 A | 4/1984 | Pohl | |
| 4,578,168 A | 3/1986 | Hofmann | |
| 4,664,097 A | 5/1987 | McGrath et al. | |
| 4,994,384 A | 2/1991 | Prather et al. | |
| 5,057,420 A | 10/1991 | Massey | |
| 5,096,822 A | 3/1992 | Rosenkrans, Jr. et al. | |
| 5,177,196 A | 1/1993 | Meyer, Jr. et al. | |
| 5,213,979 A | 5/1993 | First et al. | |
| 5,223,618 A | 6/1993 | Cook et al. | |
| 5,272,071 A | 12/1993 | Chappel | |
| 5,283,194 A | 2/1994 | Schmukler | |
| 5,378,825 A | 1/1995 | Cook et al. | |
| 5,466,786 A | 11/1995 | Buhr et al. | |
| 5,578,461 A | 11/1996 | Sherwin et al. | |
| 5,602,240 A | 2/1997 | De Mesmaeker et al. | |
| 5,610,289 A | 3/1997 | Cook et al. | |
| 5,614,617 A | 3/1997 | Cook et al. | |
| 5,672,697 A | 9/1997 | Buhr et al. | |
| 5,705,629 A | 1/1998 | Bhongle | |
| 5,712,156 A | 1/1998 | Fry et al. | |
| 5,714,606 A | 2/1998 | Acevedo et al. | |
| 5,777,092 A | 7/1998 | Cook et al. | |
| 5,843,780 A | 12/1998 | Thomson | |
| 5,858,988 A | 1/1999 | Wang | |
| 5,945,577 A | 8/1999 | Stice et al. | |
| 5,981,732 A | 11/1999 | Cowsert | |
| 5,994,619 A | 11/1999 | Stice et al. | |
| 6,011,197 A | 1/2000 | Strelchenko et al. | |
| 6,046,321 A | 4/2000 | Cowsert | |
| 6,107,091 A | 8/2000 | Cowsert | |
| 6,107,543 A | 8/2000 | Sims et al. | |
| 6,200,806 B1 | 3/2001 | Thomson | |
| 6,235,970 B1 | 5/2001 | Stice et al. | |
| 6,365,354 B1 | 4/2002 | Bennett et al. | |
| 6,410,323 B1 | 6/2002 | Roberts et al. | |

(Continued)

FOREIGN PATENT DOCUMENTS

| | | |
|---|---|---|
| CN | 107299113 A | 10/2017 |
| GB | 2318578 B | 1/2000 |

(Continued)

OTHER PUBLICATIONS

Walport et al. Human UTY(KDM6C) Is a Male-specific N-Methyl Lysyl Demethylase. J Biol Chem. Jun. 27, 2014; 289(26): 18302-18313. Published online May 5, 2014. (Year: 2014).*
Derived. Dictionary.com (accessed at https://www.dictionary.com/browse/derived on Aug. 1, 2024) (Year: 2024).*
Tukiainen et al. Landscape of X chromosome inactivation across human tissues. Nature. Oct. 11, 2017;550(7675):244-248. (Year: 2017).*
Jones et al. Structural Basis of Histone Demethylase KDM6B Histone 3 Lysine 27 Specificity. Biochemistry. Feb. 6, 2018;57(5):585-592. (Year: 2018).*
Cascalho et al. The Future of Organ Replacement—Needs, Potential Applications and Obstacles to Application. Transplant Proc. Mar. 2006;38(2):362-364. (Year: 2006).*
Suchy et al. iPSC-Derived Organs In Vivo: Challenges and Promise. Cell Stem Cell. Jan. 4, 2018;22(1):21-24. (Year: 2018).*

(Continued)

*Primary Examiner* — Valarie E Bertoglio
*Assistant Examiner* — Briana N Ebbinghaus
(74) *Attorney, Agent, or Firm* — Greenberg Traurig LLP; Melissa Hunter-Ensor; Leslie Serunian

(57) ABSTRACT

The present invention features compositions and methods for recapitulating physiological X-chromosome inactivation (XCI) in a cell, including a cell of any embryo generated by Somatic Cell Nuclear Transfer (SCNT). In one aspect, the invention features a method for generating physiological X chromosome inactivation in an embryo generated by SCNT, the method comprising injecting the embryo generated via SCNT with an H3K27me3-specific demethylase polypeptide or a polynucleotide encoding said demethylase. Disclosed herein are methods, compositions, and kits comprising an agent which increases the expression of genes encoding an H3K27me3-specific demethylase, or increases the activity of human H3K27me3-specific demethylase.

13 Claims, 15 Drawing Sheets
Specification includes a Sequence Listing.

(56) References Cited

U.S. PATENT DOCUMENTS

| | | | |
|---|---|---|---|
| 6,566,131 | B1 | 5/2003 | Cowsert |
| 6,566,135 | B1 | 5/2003 | Watt |
| 6,700,037 | B2 | 3/2004 | Damiani et al. |
| 7,838,727 | B2 | 11/2010 | Lanza et al. |
| 8,173,592 | B1 | 5/2012 | Engel et al. |
| 8,278,036 | B2 | 10/2012 | Kariko et al. |
| 8,691,966 | B2 | 4/2014 | Kariko et al. |
| 8,748,089 | B2 | 6/2014 | Kariko et al. |
| 8,835,108 | B2 | 9/2014 | Kariko et al. |
| 10,266,848 | B2 | 4/2019 | Zhang et al. |
| 11,390,885 | B2 | 7/2022 | Zhang et al. |
| 2002/0013957 | A1 | 1/2002 | Damiani et al. |
| 2003/0003469 | A1 | 1/2003 | Stinchcomb et al. |
| 2004/0025193 | A1 | 2/2004 | Echelard et al. |
| 2004/0148648 | A1 | 7/2004 | Behboodi et al. |
| 2004/0268422 | A1 | 12/2004 | Schatten et al. |
| 2005/0042620 | A1 | 2/2005 | Hampel et al. |
| 2006/0015950 | A1 | 1/2006 | Overstrom et al. |
| 2008/0057041 | A1 | 3/2008 | Chung et al. |
| 2009/0055945 | A1 | 2/2009 | Kishigami et al. |
| 2009/0286852 | A1 | 11/2009 | Kariko et al. |
| 2010/0138947 | A1 | 6/2010 | Vassiliev et al. |
| 2011/0136145 | A1 | 6/2011 | Song et al. |
| 2011/0139145 | A1 | 6/2011 | Mackamul |
| 2011/0172107 | A1 | 7/2011 | Katz et al. |
| 2012/0034192 | A1 | 2/2012 | Young et al. |
| 2012/0322864 | A1 | 12/2012 | Rossi et al. |
| 2013/0111615 | A1 | 5/2013 | Kariko et al. |
| 2013/0189780 | A1 | 7/2013 | Shoemaker et al. |
| 2014/0094387 | A1 | 4/2014 | Hamamoto et al. |
| 2014/0161785 | A1 | 6/2014 | Liu et al. |
| 2014/0234968 | A1 | 8/2014 | Chung et al. |
| 2015/0038496 | A1 | 2/2015 | Amigorena et al. |
| 2017/0327846 | A1 | 11/2017 | Zhang et al. |
| 2018/0291400 | A1 | 10/2018 | Zhang et al. |
| 2018/0298405 | A1 | 10/2018 | Zhang et al. |
| 2020/0181648 | A1 | 6/2020 | Zhang et al. |
| 2021/0155959 | A1 | 5/2021 | Zhang et al. |
| 2023/0015276 | A1 | 1/2023 | Zhang et al. |

FOREIGN PATENT DOCUMENTS

| | | |
|---|---|---|
| GB | 2331751 B | 1/2000 |
| JP | 2007117081 A | 5/2007 |
| JP | 2017528142 A | 9/2017 |
| WO | 1990003432 A1 | 4/1990 |
| WO | 1991006667 A1 | 5/1991 |
| WO | 1991009955 A1 | 7/1991 |
| WO | 1992020808 A1 | 11/1992 |
| WO | 1993005166 A1 | 3/1993 |
| WO | 1993009222 A2 | 5/1993 |
| WO | 1994012650 A2 | 6/1994 |
| WO | 1994024274 A1 | 10/1994 |
| WO | 1994026884 A1 | 11/1994 |
| WO | 1999032619 A1 | 7/1999 |
| WO | 2000059542 A1 | 10/2000 |
| WO | 2001068836 A2 | 9/2001 |
| WO | 2006052646 A2 | 5/2006 |
| WO | 2009143421 A2 | 11/2009 |
| WO | 2010033920 A2 | 3/2010 |
| WO | 2012029957 A1 | 3/2012 |
| WO | 20120299571 A1 | 3/2012 |
| WO | 2014197835 A2 | 12/2014 |
| WO | 2016044271 A2 | 3/2016 |
| WO | 2017062706 A1 | 4/2017 |
| WO | 2018073787 A2 | 4/2018 |
| WO | 2019018635 A1 | 1/2019 |
| WO | 2019195738 A1 | 10/2019 |

OTHER PUBLICATIONS

Takeo et al. Organ regeneration based on developmental biology: past and future. Curr Opin Genet Dev. Oct. 2018:52:42-47. Epub Jun. 5, 2018. (Year: 2018).*

Canovas et al. Jumonji domain-containing protein 3 regulates histone 3 lysine 27 methylation during bovine preimplantation development. Proc Natl Acad Sci U S A. Feb. 14, 2012;109(7):2400-5. Epub Jan. 30, 2012. (Year: 2012).*

Oback et al. Cloning Cattle. Cloning Stem Cells. 2003;5(4):243-56. (Year: 2003).*

Van de Berg et al. X Chromosome Inactivation Is Initiated in Human Preimplantation Embryos. Am J Hum Genet. Jun. 2009;84(6):771-9. Epub May 28, 2009. (Year: 2009).*

De Santa et al. The Histone H3 Lysine-27 Demethylase Jmjd3 Links Inflammation to Inhibition of Polycomb-Mediated Gene Silencing. Cell. Sep. 21, 2007;130(6):1083-94. Epub Sep. 6, 2007. (Year: 2007).*

Lysine-specific demethylase 6B isoform 2 [Homo sapiens]. NCBI. (accessed at: https://www.ncbi.nlm.nih.gov/protein/NP_001335645.1) (Year: 2025).*

Iu et al., "Cloning of Macaque Monkeys by Somatic Cell Nuclear Transfer," Cell, Feb. 8, 2018, vol. 172, pp. 881-887.

Liu et al., "H3K9 demethylase KDM4E is an epigenetic regulator for bovine embryonic development and a defective factor for nuclear reprogramming," Development, 2018, vol. 145, No. 4, dev158261, pp. 1-12.

Matoba et al., "Embryonic Development following Somatic Cell Nuclear Transfer Impeded by Persisting Histone Methylation," Cell, Nov. 6, 2014, vol. 159, pp. 884-895.

Bai et al., "Kdm6a overexpression improves the development of cloned mouse embryos," Zygote, Feb. 2018, vol. 26, No. 1, pp. 24-32.

Barberi et al., "Neural subtype specification of fertilization and nuclear transfer embryonic stem cells and application in parkinsonian mice," Nature Biotechnology, Oct. 2003, vol. 21, No. 10, pp. 1200-1207.

Borensztein et al., "Xist-dependent imprinted X inactivation and the early developmental consequences of its failure," Nature Structural & Molecular Biology, 2017, vol. 24, No. 3, pp. 226-233.

Branco et al., "Maternal DNA Methylation Regulates Early Trophoblast Development," Developmental Cell, Jan. 25, 2016 vol. 36, pp. 152-163.

Brind'Amour et al., "An ultra-low-input native ChIP-seq protocol for genome-wide profiling of rare cell populations," Nature Communications, 2015, vol. 6, Article No. 6033, pp. 1-8.

Chung et al., "Embryonic and extraembryonic stem cell lines derived from single mouse blastomeres," Nature, Jan. 12, 2006, vol. 439, pp. 216-219.

Collas et al., "Factors Affecting the Efficiency of Nuclear Transplantation in the Rabbit Embryo," Biology of Reproduction, 1990, vol. 43, pp. 877-884.

Fukuda et al., "Chromatin condensation of Xist genomic loci during oogenesis in mice," Development, 2015, vol. 142, pp. 4049-4055.

Giorgetti et al., "Predictive Polymer Modeling Reveals Coupled Fluctuations in Chromosome Conformation and Transcription," Cell, May 8, 2014, vol. 157, pp. 950-963.

Inoue et al., "Maternal H3K27me3 controls DNA methylation-independent imprinting," Nature, Jul. 27, 2017, vol. 547, pp. 419-424.

Inoue et al., "Nucleosome assembly is required for nuclear pore complex assembly in mouse zygotes, " Nature Structural & Molecular Biology, 2014, vol. 21, pp. 609-616.

Kobayashi et al., "Contribution of Intragenic DNA Methylation in Mouse Gametic DNA Methylomes to Establish Docyte-Specific Heritable Marks," PLoS Genetics, Jan. 2012, vol. 8, No. 1, e1002440, pp. 1-14.

Liu et al., "Distinct features of H3K4me3 and H3K27me3 chromatin domains in pre-implantation embryos," Nature, Sep. 22, 2016, vol. 537, pp. 558-562.

Liu et al., "Identification of key factors conquering developmental arrest of somatic cell cloned embryos by combining embryo biopsy and single-cell sequencing," Cell Discovery, 2016, vol. 2, No. 16010, pp. 1-15.

Matoba et al., "RNAi-mediated knockdown of Xist can rescue the impaired postimplantation development of cloned mouse embryos,"

(56) References Cited

OTHER PUBLICATIONS

Proceedings of the National Academy of Sciences of the United States of America, Dec. 20, 2011, vol. 108, No. 51, pp. 20621-20626.

Ogonuki et al., "The Effect on Intracytoplasmic Sperm Injection Outcome of Genotype, Male Germ Cell Stage and Freeze-Thawing in Mice," PLoS ONE, Jun. 2010, vol. 5, No. 6, e11062, pp. 1-7.

Ogura et al., "Birth of Mice After Nuclear Transfer by Electrofusion Using Tail Tip Cells," Molecular Reproduction and Development, 2000, vol. 57, pp. 55-59.

Ogura et al., "Microinsemination and Nuclear Transfer Using Male Germ Cells," International Review of Cytology, 2005, vol. 246, pp. 189-229.

Ogura et al., "Recent advancements in cloning by somatic cell nuclear transfer," Philosophical Transactions of The Royal Society B, 2013, vol. 368, Article No. 20110329, pp. 1-12.

Okae et al., "RNA sequencing-based identification of aberrant imprinting in cloned mice," Human Molecular Genetics, 2014, vol. 23, No. 4, pp. 992-1001.

Okamoto et al., "Evidence for de novo imprinted X-chromosome inactivation independent of meiotic inactivation in mice," Nature, Nov. 17, 2005, vol. 438, pp. 369-373.

Piedrahita et al., "Generation of Transgenic Porcine Chimeras using Primordial Germ Cell-Derived Colonies," Biology of Reproduction, 1998, vol. 58, pp. 1321-1329.

Rideout et al., "Correction of a Genetic Defect by Nuclear Transplantation and Combined Cell and Gene Therapy," Cell, Apr. 5, 2002, vol. 109, pp. 17-27.

Ruan et al., "XIST Derepression in Active X Chromosome Hinders Pig Somatic Cell Nuclear Transfer," Stem Cell Reports, 2018, vol. 10, No. 2, pp. 494-508.

Shao et al., "MAnorm: a robust model for quantitative comparison of ChIP-Seq data sets," Genome Biology, 2012, vol. 13, Article No. R16, pp. 1-16.

Shim et al., "Isolation of Pluripotent Stem Cells from Cultured Porcine Primordial Germ Cells," Biology of Reproduction, 1997, vol. 57, pp. 1089-1095.

Tan et al., "Impaired imprinted X chromosome inactivation is responsible for the skewed sex ratio following in vitro fertilization," Proceedings of the National Academy of Sciences of the United States of America, Mar. 22, 2016, vol. 113, No. 12, pp. 3197-3202.

The Encode Portal, Dec. 23, 2011, (https://www.encodeproject.org/files/ENCFF001KDT/).

Thomson et al., "Embryonic Stem Cell Lines Derived from Human Blastocysts," Science, Nov. 6, 1998, vol. 282, pp. 1145-1147.

Thomson et al., "Isolation of a primate embryonic stem cell line," Proceedings of the National Academy of Sciences of the United States of America, Aug. 1995, vol. 92, pp. 7844-7848.

Tsung et al., "[Expression of exogenous porcine transforming growth factor beta-1 gene in ES cells and its effect on their differentiation in vitro]," Shi yan Sheng wu xue bao, Jun. 1, 1995, vol. 28, No. 2, pp. 173-189. (English Abstract Only).

Wagoner et al., "Functional Enucleation of Bovine Oocytes: Effects of Centrifugation and Ultraviolet Light," Theriogenology, 1996, vol. 46, pp. 279-284.

Wang et al., "Programming and Inheritance of Parental DNA Methylomes in Mammals," Cell, May 8, 2014, vol. 157, pp. 979-991.

Wheeler, Matthew B., "Development and validation of swine embryonic stem cells: a review," Reproduction, Fertility and Development, 1994, vol. 6, pp. 563-568.

Wutz et al., "A Shift from Reversible to Irreversible X Inactivation Is Triggered during ES Cell Differentiation," Molecular Cell, Apr. 2000, vol. 5, pp. 695-705.

Yamaguchi et al., "Role of Tet1 in genomic imprinting erasure," Nature, Dec. 19, 2013, vol. 504, No. 7480, pp. 460-464.

Zheng et al., "Resetting Epigenetic Memory by Reprogramming of Histone Modifications in Mammals," Molecular Cell, Sep. 15, 2016, vol. 63, pp. 1066-1079.

Extended European Search Report dated Feb. 4, 2022 in corresponding European Patent Application No. 18927137.2 (10 pages).

Inoue, et al., "Genomic imprinting of Xist by maternal H3K27 me3," Genes & Development, Oct. 1, 2017, vol. 31, pp. 1927-1932.

Welstead, et al., "X-linked H3K27 me3 demethylase Utx is required for embryonic development in a sex-specific manner," Proceedings of the National Academy of Sciences USA, Jul. 23, 2012, vol. 109, pp. 13004-13009.

International Search Report and Written Opinion for corresponding PCT/US2018/072890, dated Nov. 16, 2018 (17 pages).

Loi et al., "A New, Dynamic Era for Somatic Cell Nuclear Transfer?," Trends in Biotechnology, 2016, vol. 34, No. 10, pp. 791-797.

Lagutina et al., "Interspecies Somatic Cell Nuclear Transfer: Advancements and Problems," Cellular Reprogramming, 2013, vol. 15, No. 5, pp. 374-384.

Meirelles et al., "Complete Replacement of the Mitochondrial Genotype in a Bos indicus Calf Reconstructed by Nuclear Transfer to a Bos taurus Oocyte," Genetics, May 2001, vol. 158, pp. 351-356.

Xie et al., "Histone H3 lysine 27 trimethylation acts as an epigenetic barrier in porcine nuclear reprogramming," Reproduction, 2016, vol. 151, pp. 9-16.

Office Action dated Oct. 16, 2023 in corresponding Korean Patent Application No. 10-2021-7004477 (4 pages).

English translation of Office Action dated Oct. 16, 2023 in corresponding Korean Patent Application No. 10-2021-7004477 (3 pages).

Office Action dated Dec. 30, 2023 in corresponding Chinese Patent Application No. 201880097483.8 (7 pages).

English translation of Office Action dated Dec. 30, 2023 in corresponding Chinese Patent Application No. 201880097483.8 (7 pages).

Office Action dated Jan. 22, 2024 in corresponding Japanese Patent Application No. 2023-010707 (7 pages).

English translation of Office Action dated Jan. 22, 2024 in corresponding Japanese Patent Application No. 2023-010707 (7 pages).

Akagi et al., "Treatment with a Histone Deacetylase Inhibitor after Nuclear Transfer Improves the Preimplantation Development of Cloned Bovine Embryos," Journal of Reproduction and Development, 2011, vol. 57, No. 1, pp. 120-126.

Antony et al., "Transient JMJD2B-Mediated Reduction of H3K9me3 Levels Improves Reprogramming of Embryonic Stem Cells into Cloned Embryos," Molecular and Cellular Biology, Mar. 2013, vol. 33, No. 5, pp. 974-983.

Antony, Jisha, "Manipulation of the epigenetic mark histone 3 lysine 9 tri-methylation (H3K9me3) in donor cells prior to nuclear transfer," Doctoral Dissertation at The University of Auckland, 2011, ResearchSpace@Auckland, 2011, pp. i-141.

Apostolou et al., "Chromatin Dynamics during Cellular Reprogramming," Nature, Oct. 24, 2013, vol. 502, No. 7472, pp. 462-471.

Braasch et al., "RNA Interference in Mammalian Cells by Chemically-Modified RNA," Biochemistry, 2003, vol. 42, No. 26, pp. 7967-7975.

Campbell et al., "Sheep cloned by nuclear transfer from a cultured cell line," Nature, Mar. 7, 1996, vol. 380, pp. 64-66.

Chang et al., "High-throughput sequencing reveals the disruption of methylation of imprinted gene in induced pluripotent stem cells," Cell Research, Mar. 2014, vol. 24, No. 3, pp. 293-306.

Chen et al., "H3K9 methylation is a barrier during somatic cell reprogramming into iPSCs," Nature Genetics, Jan. 2013, vol. 45, No. 1, pp. 34-42.

Chung et al., "Histone Demethylase Expression Enhances Human Somatic Cell Nuclear Transfer Efficiency and Promotes Derivation of Pluripotent Stem Cells," Cell Stem Cell, 2015, vol. 17, No. 6, pp. 758-766.

Chung et al., "Human Somatic Cell Nuclear Transfer Using Adult Cells," Cell Stem Cell, Jun. 5, 2014, vol. 14, No. 6, pp. 777-780.

Chung et al., "Reprogramming of Human Somatic Cells Using Human and Animal Oocytes," Cloning and Stem Cells, 2009, vol. 11, No. 2, pp. 213-223.

Cibelli et al., "Cloned Transgenic Calves Produced from Nonquiescent Fetal Fibroblasts," Science, May 22, 1998, vol. 280, No. 5367, pp. 1256-1258.

(56)                    References Cited

OTHER PUBLICATIONS

Cibelli et al., "Rapid Communication: Somatic Cell Nuclear Transfer in Humans: Pronuclear and Early Embryonic Development," e-biomed: The Journal of Regenerative Medicine, Nov. 2001, vol. 2, No. 5, pp. 25-31.

Cibelli et al., "Transgenic bovine chimeric offspring produced from somatic cell-derived stem-like cells," Nature Biotechnology, Jul. 1998, vol. 16, pp. 642-646.

Coburn et al., "Potent and Specific Inhibition of Human Immunodeficiency Virus Type 1 Replication by RNA Interference," Journal of Virology, Sep. 2002, vol. 76, No. 18, pp. 9225-9231.

Colas et al., "Genetic selection of peptide aptamers that recognize and inhibit cyclin-dependent kinase 2," Nature, Apr. 11, 1996, vol. 380, pp. 548-550.

Collas et al., "Nuclear Transplantation by Microinjection of Inner Cell Mass and Granulosa Cell Nuclei," Molecular Reproduction and Development, 1994, vol. 38, No. 3, pp. 264-267.

Drukker et al., "The immunogenicity of human embryonic stem-derived cells," Trends in Biotechnology, Mar. 2004, vol. 22, No. 3, pp. 136-141.

Elbashir et al., "Duplexes of 21-nucleotide RNAs mediate RNA interference in cultured mammalian cells," Nature, May 24, 2001, vol. 411, pp. 494-498.

Elbashir et al., "RNA interference is mediated by 21- and 22-nucleotide RNAs," Genes & Development, 2001, vol. 15, pp. 188-200.

Eskeland et al., "The N-Terminus of Drosophila SU(VAR)3-9 Mediates Dimerization and Regulates Its Methyltransferase Activity," Biochemistry, 2004, vol. 43, No. 12, pp. 3740-3749.

French et al., "Development of Human Cloned Blastocysts Following Somatic Cell Nuclear Transfer with Adult Fibroblasts," Stem Cells, 2008, vol. 26, pp. 485-493.

Fu et al., "Abnormal histone H3K9 dimethylation but normal dimethyltransferase EHMT2 expression in cloned sheep embryos," Theriogenology, 2012, vol. 78, No. 9, pp. 1929-1938.

Fu et al., "Effects of the Histone Methyltransferase Inhibitor UNC0638 on Histone H3K9 Dimethylation of Cultured Ovine Somatic Cells and Development of Resulting Early Cloned Embryos," Reproduction in Domestic Animals, 2014, vol. 49, pp. e21-e25.

GenBank Accession No. BC156878.1, "Synthetic construct Mus musculus clone", Create Date: Dec. 11, 2007, 3 pages.

Gurdon, J.B., "The Effects of Ultraviolet Irradiation on Uncleaved Eggs of Xenopus Laevis," The Quarterly Journal of Microscopical Science, Sep. 1960, vol. s3-101, pp. 299-311.

Harborth et al., "Identification of essential genes in cultured mammalian cells using small interfering RNAs," Journal of Cell Science, 2001, vol. 114, No. 24, pp. 4557-4565.

Hochedlinger et al., "Nuclear Transplantation, Embryonic Stem Cells, and the Potential for Cell Therapy," The New England Journal of Medicine, Jul. 17, 2003, vol. 349, No. 3, pp. 275-286.

Inoue et al., "Impeding Xist Expression from the Active X Chromosome Improves Mouse Somatic Cell Nuclear Transfer," Science, Oct. 22, 2010, vol. 330, pp. 496-499.

Inoue, K. et al., "Inefficient reprogramming of the hematopoietic stem cell genome following nuclear transfer," Journal of Cell Science, 2006, vol. 119, pp. 1985-1991.

Jackson et al., "Expression profiling reveals off-target gene regulation by RNAi," Nature Biotechnology, 2003, vol. 21, No. 6, pp. 635-637.

Jaenisch et al., "Gene Targeting: Mouse Embryonic Stem Cell," Open Biosystems Product Catalog, 2007, pp. 60-62.

Jaenisch, Rudolf, "Human Cloning-The Science and Ethics of Nuclear Transplantation," The New England Journal of Medicine, Dec. 30, 2004, vol. 351, No. 27, pp. 2787-2791.

Jullien et al., "Mechanisms of nuclear reprogramming by eggs and oocytes: a deterministic process?," Nature Reviews Molecular Cell Biology, 2011, vol. 12, No. 7, pp. 453-459.

Kallingappa et al., "Quiescence Induces Long-Term Epigenetic Changes in Bovine Fibroblasts That Improve Their Reprogramming Into Cloned Animals," Reproduction, Fertility and Development, Dec. 4, 2012, vol. 25, No. 1, pp. 171-172.

Kanka et al., "Transcriptional Activity and Nucleolar Ultrastructure of Embryonic Rabbit Nuclei After Transplantation to Enucleated Oocytes," Molecular Reproduction and Development, 1996, vol. 43, No. 2, pp. 135-144.

Kawase et al., "Mouse Embryonic Stem (ES) Cell Lines Established From Neuronal Cell-Derived Cloned Blastocysts," Genesis, 2000, vol. 28, pp. 156-163.

Keefer et al., "Bovine Inner Cell Mass Cells as Donor Nuclei in the Production of Nuclear Transfer Embryos and Calves," Biology of Reproduction, Apr. 1994, vol. 50, No. 4, pp. 935-939.

Kigami et al., "MuERV-L Is One of the Earliest Transcribed Genes in Mouse One-Cell Embryos," Biology of Reproduction, 2003, vol. 68, pp. 651-654.

Kim et al., "Regulation of Tumor Suppressor p53 and HCT116 Cell Physiology by Histone Demethylase JMJD2D/KDM4D," PLoS One, Apr. 2012, vol. 7, No. 4, e34618, pp. 1-8.03, vol. 68, No. 2, pp. 651-654.

Kishigami et al., "Significant improvement of mouse cloning technique by treatment with trichostatin A after somatic nuclear transfer," Biochemical and Biophysical Research Communications, 2006, vol. 340, pp. 183-189.

Lachner et al., "Methylation of histone H3 lysine 9 creates a binding site for HP1 proteins," Nature, Mar. 1, 2001, vol. 410, pp. 116-120.

Lanza et al., "Human therapeutic cloning," Nature Medicine, Sep. 1999, vol. 5, No. 9, pp. 975-977.

Li et al., "Inhibition of SUV39H1 Methyltransferase Activity by DBC1," The Journal of Biological Chemistry, Apr. 17, 2009, vol. 284, No. 16, pp. 10361-10366.

Li et al., "Rabbits generated from fibroblasts through nuclear transfer," Reproduction, 2006, vol. 131, No. 6, pp. 1085-1090.

Liao et al., "Dnmt3l-knockout donor cells improve somatic cell nuclear transfer reprogramming efficiency," Reproduction, 2015, vol. 150, pp. 245-256.

Lieber et al., "Selection of Efficient Cleavage Sites in Target RNAs by Using a Ribozyme Expression Library," Molecular and Cellular Biology, Jan. 1995, vol. 15, No. 1, pp. 540-551.

Liu et al., "Optimization of Cellular Activity of G9a Inhibitors 7-Aminoalkoxy-quinazolines," Journal of Medicinal Chemistry, Sep. 8, 2011, vol. 54, No. 17, pp. 6139-6150.

Loh et al., "Jmjd1a and Jmjd2c histone H3 Lys 9 demethylases regulate self-renewal in embryonic stem cells," Genes & Development, 2007, vol. 21, No. 20, pp. 2545-2557.

Ma et al., "Abnormalities in human pluripotent cells due to reprogramming mechanisms," Nature, 2014, vol. 511, No. 7508, pp. 177-183.

Ma et al., "Metabolic rescue in pluripotent cells from patients with mtDNA disease," Nature, Aug. 13, 2015, vol. 524, pp. 234-238.

Markoulaki et al., "Somatic cell nuclear transfer and derivation of embryonic stem cells in the mouse," Methods, Jun. 2008, vol. 45, No. 2, pp. 101-114.

Masters et al., "Short tandem repeat profiling provides an international reference standard for human cell lines," Proceedings of the National Academy of Sciences of the United States of America, 2001, vol. 98, No. 14, pp. 8012-8017.

Matoba et al., "Loss of H3K27me3 Imprinting in Somatic Cell Nuclear Transfer Embryos Disrupts Post-Implantation Development," Cell Stem Cell, Sep. 6, 2018, vol. 23, No. 3, pp. 343-354.

Matsui et al., "Proviral silencing in embryonic stem cells requires the histone methyltransferase ESET," Nature, 2010, vol. 464, No. 7290, pp. 927-931.

Mcmanus et al., "Gene silencing using micro-RNA designed hairpins," RNA, 2002, vol. 8, pp. 842-850.

Mitalipov et al., "Totipotency, Pluripotency and Nuclear Reprogramming," Advances in Biochemical Engineering / Biotechnology, 2009, vol. 114, pp. 185-199.

Munsie et al., "Isolation of pluripotent embryonic stem cells from reprogrammed adult mouse somatic cell nuclei," Current Biology, Aug. 2000, vol. 10, No. 16, pp. 989-992.

NCBI "NM_018039" accessed at https://www.ncbi.nlm.nih.gov/nuccore/39653316?sat=18&satkey=1438804, on Oct. 14, 2019, pp. 1-3.

Noggle et al., "Human oocytes reprogram somatic cells to a pluripotent state," Nature, Oct. 2011, vol. 478, pp. 70-75.

(56)          References Cited

OTHER PUBLICATIONS

Ono et al., "Cloned Mice from Fetal Fibroblast Cells Arrested at Metaphase by a Serial Nuclear Transfer," Biology of Reproduction, 2001, vol. 64, No. 1, pp. 44-50.

Paddison et al., "Short hairpin RNAs (shRNAs) induce sequence-specific silencing in mammalian cells," Genes & Development, 2002, vol. 16, pp. 948-958.

Pasque et al., "Efficiencies and Mechanisms of Nuclear Reprogramming," Cold Spring Harbor Symposia on Quantitative Biology, 2010, vol. 75, pp. 189-200.

Pasque et al., "Epigenetic factors influencing resistance to nuclear reprogramming," Trends in Genetics, Dec. 2011, vol. 27, No. 12, pp. 516-525.

Pedersen et al., "The Demethylase JMJD2C Localizes to H3K4me3-Positive Transcription Start Sites and Is Dispensable for Embryonic Development," Molecular and Cellular Biology, Mar. 2014, vol. 34, No. 6, pp. 1031-1045.

Peters et al., "Loss of the Suv39h Histone Methyltransferases Impairs Mammalian Heterochromatin and Genome Stability," Cell, Nov. 2, 2001, vol. 107, No. 3, pp. 323-337.

Pichugin et al., "Dynamics of constitutive heterochromatin: two contrasted kinetics of genome restructuring in early cloned bovine embryos," Reproduction, 2010, vol. 139, pp. 129-137.

Pontecorvo et al., "Time and mode of fusion of human fibroblasts treated with polyethylene glycol (PEG)," Nature, Jan. 20, 1977, vol. 265, pp. 257-258.

Probst et al., "A Strand-Specific Burst in Transcription of Pericentric Satellites Is Required for Chromocenter Formation and Early Mouse Development," Developmental Cell, Oct. 19, 2010, vol. 19, No. 4, pp. 625-638.

Qin et al., "Inhibiting HIV-1 infection in human T cells by lentiviral-mediated delivery of small interfering RNA against CCR5," Proceedings of the National Academy of Sciences of the United States of America, Jan. 7, 2003, vol. 100, No. 1, pp. 183-188.

Rideout et al., "Generation of mice from wild-type and targeted ES cells by nuclear cloning," Nature Genetics, Feb. 2000, vol. 24, No. 2, pp. 109-110.

Rodriguez-Osorio et al., "Reprogramming mammalian somatic cells," Theriogenology, Dec. 2012, vol. 78, No. 9, pp. 1869-1886.

Rubinson et al., "A lentivirus-based system to functionally silence genes in primary mammalian cells, stem cells and transgenic mice by RNA interference," Nature Genetics, Mar. 2003, vol. 33, pp. 401-406.

Santos et al., "Epigenetic Marking Correlates with Developmental Potential in Cloned Bovine Preimplantation Embryos," Current Biology, Jul. 1, 2003, vol. 13, No. 13, pp. 1116-1121.

Schneider et al., "Building blocks for oligonucleotide analogs with dimethylene-sulfide, -sulfoxide, and -sulfone groups replacing phosphodiester linkages," Tetrahedron Letters, 1990, vol. 31, No. 3, pp. 335-338.

Schultz, Richard M., "The molecular foundations of the maternal to zygotic transition in the preimplantation embryo," Human Reproduction Update, 2002, vol. 8, No. 4, pp. 323-331.

Shaaban et al., "Reprogramming the Histone Code," Chemistry & Biology, Mar. 2007, vol. 14, No. 3, pp. 242-244.

Shu et al., "Preliminary study on human cumulus cell nuclear transfer," Fertility and Sterility, Sep. 2002, vol. 78, Suppl. 1, p. S286.

Sims et al., "Production of calves by transfer of nuclei from cultured inner cell mass cells," Proceedings of the National Academy of Sciences of the United States of America, Jun. 1994, vol. 91, No. 13, pp. 6143-6147.

Sridharan et al., "Proteomic and genomic approaches reveal critical functions of H3K9 methylation and heterochromatin protein-1γ in reprogramming to pluripotency," Nature Cell Biology, 2013, vol. 15, No. 7, pp. 872-882.

Sterneckert et al., "Investigating human disease using stem cell models," Nature Reviews Genetics, Sep. 2014, vol. 15, pp. 625-639.

Stewart et al., "Lentivirus-delivered stable gene silencing by RNAi in primary cells," RNA, 2003, vol. 9, No. 4, pp. 493-501.

Stice et al., "Nuclear Reprogramming in Nuclear Transplant Rabbit Embryos," Biology of Reproduction, 1988, vol. 39, No. 3, pp. 657-664.

Sui et al., "A DNA vector-based RNAi technology to suppress gene expression in mammalian cells," Proceedings of the National Academy of Sciences of the United States of America, Apr. 16, 2002, vol. 99, No. 8, pp. 5515-5520.

Suzuki et al., "Zygotically Activated Genes Are Suppressed in Mouse Nuclear Transferred Embryos," Cloning and Stem Cells, 2006, vol. 8, No. 4, pp. 295-304.

Sweis et al., "Discovery and Development of Potent and Selective Inhibitors of Histone Methyltransferase G9a," ACS Medicinal Chemistry Letters, 2014, vol. 5, No. 2, pp. 205-209.

Tachibana et al., "Human Embryonic Stem Cells Derived by Somatic Cell Nuclear Transfer," Cell, Jun. 6, 2013, vol. 153, No. 6, pp. 1228-1238.

Takahashi et al., "Inhibition of histone H3K9 methyltransferases by gliotoxin and related epipolythiodioxopiperazines," The Journal of Antibiotics, 2012, vol. 65, pp. 263-265.

Teperek et al., "Nuclear reprogramming of sperm and somatic nuclei in eggs and oocytes," Reproductive Medicine and Biology, 2013, vol. 12, pp. 133-149.

The Encode Project Consortium, "A User's Guide to the Encyclopedia of DNA Elements (ENCODE), " PLoS Biology, Apr. 2011, vol. 9, No. 4, e1001046, pp. 1-21.

The Encode Project Consortium, "An integrated encyclopedia of DNA elements in the human genome," Nature, Sep. 6, 2012, vol. 489, pp. 57-74.

Tuschl et al., "Targeted mRNA degradation by double-stranded RNA in vitro," Genes & Development, 1999, vol. 13, pp. 3191-3197.

Van Thuan et al., "The histone deacetylase inhibitor scriptaid enhances nascent mRNA production and rescues full-term development in cloned inbred mice," Reproduction, 2009, vol. 138, pp. 309-317.

Vassena et al., "Tough beginnings: Alterations in the transcriptome of cloned embryos during the first two cell cycles," Developmental Biology, 2007, vol. 304, pp. 75-89.

Vedadi et al., "A chemical probe selectively inhibits G9a and GLP methyltransferase activity in cells," Nature Chemical Biology, 2011, vol. 7, No. 8, pp. 566-574.

Wakayama et al., "Differentiation of Embryonic Stem Cell Lines Generated from Adult Somatic Cells by Nuclear Transfer," Science, Apr. 27, 2001, vol. 292, No. 5517, pp. 740-743.

Wakayama et al., "Full-term development of mice from enucleated oocytes injected with cumulus cell nuclei," Nature, Jul. 23, 1998, vol. 394, pp. 369-374.

Wang et al., "Stable and controllable RNA interference: Investigating the physiological function of glutathionylated actin," Proceedings of the National Academy of Sciences of the United States of America, Apr. 29, 2003, vol. 100, No. 9, pp. 5103-5106.

Wilmut et al., "Viable offspring derived from fetal and adult mammalian cells," Nature, Feb. 27, 1997, vol. 385, pp. 810-813.

Wu et al., "Establishment of totipotency does not depend on Oct4A," Nature Cell Biology, Sep. 2013, vol. 15, No. 9, pp. 1089-1097.

Xie et al., "Seamless gene correction of B-thalassemia mutations in patient-specific iPSCs using CRISPR/Cas9 and piggyBac," Genome Research, 2014, vol. 24, pp. 1526-1533.

Yamada et al., "Human oocytes reprogram adult somatic nuclei of a type 1 diabetic to diploid pluripotent stem cells," Nature, Jun. 26, 2014, vol. 510, pp. 533-536.

Yamanaka et al., "Nuclear reprogramming to a pluripotent state by three approaches," Nature, Jun. 10, 2010, vol. 465, No. 7299, pp. 704-712.

Yang et al., "Nuclear reprogramming of cloned embryos and its implications for therapeutic cloning," Nature Genetics, Mar. 2007, vol. 39, No. 3, pp. 295-302.

Yang et al., "The Maternal Effect Genes UTX and JMJD3 Play Contrasting Roles in Mus musculus Preimplantation Embryo Development," Scientific Reports, 2016, vol. 6, Article No. 26711, pp. 1-11.

(56)                    References Cited

OTHER PUBLICATIONS

Yang et al., "KDM6A and KDM6B play contrasting roles in nuclear transfer embryos revealed by MERVL reporter system," EMBO Reports, 2018, vol. 19: e46240, pp. 1-19.

Yu et al., "RNA interference by expression of short-interfering RNAs and hairpin RNAs in mammalian cells," Proceedings of the National Academy of Sciences of the United States of America, Apr. 2002, vol. 99, No. 9, pp. 6047-6052.

Yusa, Kosuke, "Seamless genome editing in human pluripotent stem cells using custom endonuclease-based gene targeting and the piggyBac transposon," Nature Protocols, 2013, vol. 8, No. 10, pp. 2061-2078.

Zeng et al., "Both Natural and Designed Micro RNAs Can Inhibit the Expression of Cognate mRNAs When Expressed in Human Cells," Molecular Cell, Jun. 2002, vol. 9, No. 6, pp. 1327-1333.

Zhang et al., "Defective Chromatin Structure in Somatic Cell Cloned Mouse Embryos," Journal of Biological Chemistry, 2009, vol. 284, No. 37, pp. 24981-24987.

Zhao et al., "Significant Improvement in Cloning Efficiency of an Inbred Miniature Pig by Histone Deacetylase Inhibitor Treatment after Somatic Cell Nuclear Transfer," Biology of Reproduction, 2009, vol. 81, No. 3, pp. 525-530.

Zimmermann et al., "Fusion of Avena sativa mesophyll cell protoplasts by electrical breakdown," Biochimica et Biophysica Acta, 1981, vol. 641, No. 1, pp. 160-165.

Office Action dated Jan. 2, 2026, in corresponding Chinese Patent Application No. 201880097483.8 (3 pages).

English Translation of content of the Office Action dated Jan. 2, 2026, in corresponding Chinese Patent Application No. 201880097483.8 (1 page).

Peat et al., "Incomplete methylation reprogramming in SCNT embryos," Nature Genetics, 2012, vol. 44, No. 9, pp. 965-966.

Dominiguez-Bendala et al., "Islet Cell Therapy and Pancreatic Stem Cells," Handbook of Stem Cells, Chapter 70, 2013, pp. 835-853.

Hiendleder, "Mitochondrial DNA Inheritance after SCNT," In: Somatic Cell Nuclear Transfer; Ed. Peter Sutovskiy, Landes Bioscience and Springer Science+Business Media, LLC, Chapter 8, 2007 (16 pages).

Lai et al., "SRY (sex determining region Y)-box2 (Sox2)/polyADP-ribose polymerase 1 (Parp1) complexes regulate pluripotency,"

Proceedings of the National Academy of Sciences USA, Mar. 6, 2012, vol. 109, No. 10, pp. 3772-3777.

Reubinoff et al., "Embryonic stem cell lines from human blastocysts: somatic differentiation in vitro," Nature Biotechnology, 2000, vol. 18, pp. 399-404.

UK House of Parliaments' Select Committee on Science and Technology, "Government proposals for the regulation of hybrid and chimera embryos," Fifth Report of Session 2006-07, vol. II, Apr. 5, 2007 (7 pages).

Wang et al., "Generation and Characterization of Pluripotent Stem Cells from Cloned Bovine Embryos," Biology of Reproduction, 2005, vol. 73, pp. 149-155.

Wu et al., "Effects of Overexpression of H3K9me3 Demethylase on In Vitro Developmental Efficiency of Cloned Pig Embryos," Guangdong Agricultural Sciences, Oct. 15, 2017, vol. 44, No. 10, (English Abstract, 1 page).

Office Action dated Apr. 21, 2021, in corresponding Chinese Patent Application No. 201880097483.8 (1 page).

English Translation of the Office Action dated Apr. 21, 2021, in corresponding Chinese Patent Application No. 201880097483.8 (1 page).

Office Action dated Jun. 8, 2022, in corresponding Japanese Patent Application No. 2021-502810 (5 pages).

English Translation of the Office Action dated Jun. 8, 2022, in corresponding Japanese Patent Application No. 2021-502810 (6 pages).

Office Action dated Sep. 28, 2022 in corresponding Japanese Patent Application No. 2021-502810 (7 pages).

English Translation of the Office Action dated Sep. 28, 2022, in corresponding Japanese Patent Application No. 2021-502810 (7 pages).

Office Action dated Nov. 11, 2024, in corresponding Chinese Patent Application No. 201880097483.8 (4 pages).

English translation of Office Action dated Nov. 11, 2024, in corresponding Chinese Patent Application No. 201880097483.8 (2 pages).

Office Action dated Jun. 30, 2025, in corresponding Chinese Patent Application No. 201880097483.8 (5 pages).

English Translation of the Office Action dated Jun. 30, 2025, in corresponding Japanese Patent Application No. 201880097483.8 (6 pages).

Office Action dated Aug. 11, 2025, in corresponding European Patent Application No. 18927137.2 (7 pages).

\* cited by examiner

COMPOSITIONS AND METHODS FOR GENERATING PHYSIOLOGICAL X CHROMOSOME INACTIVATION

SEQUENCE LISTING

The present application contains a Sequence Listing which has been submitted electronically in ASCII format and is hereby incorporated by reference in its entirety. Said ASCII copy, created on Aug. 23, 2018, is named 167705_015900_PCT_SL.txt and is 57,179 bytes in size.

BACKGROUND OF THE INVENTION

In females of certain therian mammals, including rodents, one of the two X chromosomes is inactivated to achieve gene dosage compensation. During development, X-chromosome inactivation (XCI) can take place in either an imprinted or a random manner. For imprinted XCI, the paternal X chromosome (Xp) is selectively inactivated during preimplantation development. Although imprinted XCI is maintained in the extraembryonic cell lineage, it is lost in the pre-epiblast cell lineage of late blastocysts. At the peri-implantation stage, epiblast cells undergo random XCI, resulting in the silencing of either the Xp or maternal X chromosome (Xm). Previous studies have demonstrated an important role of Xist, an X-linked long noncoding RNA, in both imprinted and random XCI. The Xist RNA participates in XCI by coating and inactivating the X chromosome in cis.

To selectively silence the Xp during preimplantation development, Xist is imprinted in the Xm with a long sought-after but yet-to-be-identified mechanism. Previous studies using nuclear transfer approaches have suggested that genomic imprinting of Xist is established during oogenesis. However, analyses of DNA methyltransferase maternal knockout embryos revealed that oocyte DNA methylation is dispensable for Xist imprinting. A recent study demonstrated that overexpression of an H3K9me3 demethylase, Kdm4b, in parthenogenetic (PG) embryos partially derepresses Xist, suggesting the involvement of H3K9me3 in imprinted Xist silencing. However, the fact that PG embryos undergo nonphysiological Xist derepression of a single maternal allele raises the question of whether the derepression effect observed in the H3K9me3-depleted PG embryos is physiologically relevant. Recently, it was discovered that maternal H3K27me3 serves as an imprinting mark for DNA methylation-independent autosomal gene imprinting.

Such observations are relevant to therapeutic and reproductive cloning, where a donor nucleus from a somatic cell is transferred into an enucleated oocyte. This process is termed Somatic Cell Nuclear Transfer (SCNT) and may be accomplished by fusion of the somatic cell with the enucleated oocyte, injection of the nucleus into the enucleated oocyte, or by any other method. At present, only about 1 percent of SCNT result in the successful generation of a viable embryo. The low success rate of SCNT is associated with defects in imprinting. Accordingly, novel compositions and methods for increasing the success of SCNT and correcting defects in imprinting are required.

SUMMARY OF THE INVENTION

As described below, the present invention features compositions and methods for recapitulating physiological X-chromosome inactivation (XCI) in a cell, including a cell of any embryo generated by SCNT.

In one aspect, the invention features a method for generating physiological X chromosome inactivation in an embryo generated by Somatic Cell Nuclear Transfer (SCNT), the method comprising injecting the embryo generated via SCNT with an H3K27me3-specific demethylase polypeptide or a polynucleotide encoding said demethylase. In one embodiment, the embryo is injected with an mRNA encoding a H3K27me3-specific demethylase. In another embodiment, the polynucleotide encodes a Kdm6a, Kdm6b, or Kdm6c polypeptide. In another embodiment, the embryo is injected with between about 1000 and 2000 ng/µL of the mRNA. In another embodiment, the embryo is injected with 1800 ng/µL of mRNA. In another embodiment, the X chromosome is present in a donor nucleus derived from a somatic cell. In another embodiment, the donor nucleus is transferred into an oocyte or embryonic stem cell. In another embodiment, the polynucleotide encodes an enzymatically active fragment of an H3K27me3-specific demethylase. In another embodiment, the polynucleotide is present in a mammalian expression vector. In another embodiment, the mammalian expression vector comprises a promoter directing constitutive or inducible expression of the H3K27me3-specific demethylase. In another embodiment, the injected polypeptide is Kdm6a, Kdm6b, or Kdm6c. In another embodiment, the method reduces the expression of X-linked genes. In another embodiment, the method does not significantly change the expression of genes that escape X-chromosome imprinting. In another embodiment, the method does not significantly change autosomal gene expression. In another embodiment, the maternal allele expression bias of X-linked genes is greater than about 35-60%. In another embodiment, maternal allele expression bias of X-linked genes is greater than about 50%. In other embodiments, the embryo is an early blastocyst stage embryo or is derived from an adult somatic cell. In another embodiment, the somatic cell is obtained from a human subject. In another embodiment, the method further comprises culturing a cell from the embryo to obtain a tissue suitable for transplantation into the human subject.

In another aspect, the invention features a blastocyst produced according to the method of a previous claim.

In another aspect, the invention features a cell or tissue produced according to the method of a previous aspect.

In another aspect, the invention features a cloned organism produced by implanting the blastocyst of a previous aspect into a host uterus.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994): The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "H3K27me3-specific demethylase" is meant a protein that specifically demethylates trimethylated H3 'Lys-27. Exemplary demethylases include Kdm6a, Kdm6b, and Kdm6c.

By "KDM6A polypeptide" (lysine-specific demethylase 6A, also referred to as histone demethylase UTX) is meant a protein having at least about 85% amino acid identity to the sequence provided at NCBI Reference Sequence: 015550.2, or a fragment thereof, and having demethylase activity. An exemplary KDM6A amino acid sequence is provided below (SEQ ID NO: 1):

```
   1 mkscgvslat aaaaaaafgd eekkmaagka sgeseeasps ltaeerealg gldsrlfgfv 61 rfhedgartk allgkavrcy eslilkaegk vesdffcqlg hfnllledyp kalsayqryy 121 slqsdywkna aflyglglvy fhynafqwai kafqevlyvd psfcrakeih lrlglmfkvn 181 tdyesslkhf qlalvdcnpc tlsnaeiqfh iahlyetrk yhsakeayeq llqtenlsag 241 vkatvlqqlg wmhhtvdllg dkatkesyai qylqkslead pnsgqswyfl grcyssigkv 301 qdafisyrqs idkseasadt wcsigvlyqq qnqpmdalga yicavqldhg haaawmdlgt 361 lyescnqpqd aikcylnatr skscsntsal aarikylqaq lcnlpqgslq nktklipsie 421 eawslpipae ltsrqgamnt aqqntsdnws gghavshppv qqqahswclt pqklqhleql 481 ranrnnlnpa qklmleqles qfvlmqqhqm rptgvaqvrs tgipngptad sslptnsvsg 541 qqpqlaltrv psvsqpgvrp acpgqplang pfsaghvpcs tsrtlgstdt ilignnhitg 601 sgsngnvpyl qrnaltlphn rtnltssaee pwknqlsnst qglhkgqssh sagpngerpl 661 sstgpsqhlq aagsgignqn ghptlpsnsv tqgaalnhls shtatsggqq gitltkeskp 721 sgniltvpet srhtgetpns tasveglpnh vhqmtadavc spshgdsksp gllssdnpql 781 sallmgkann nvgtgtcdkv nnihpavhtk tdnsvassps saistatpsp ksteqtttns 841 vtslnsphsg lhtingegme esqspmktdl llvnhkpspq iipsmsvsiy pssaevlkac 901 rnlgknglsn ssilldkcpp prppsspypp lpkdklnppt psiylenkrd affpplhqfc 961 tnpnnpvtvi rglagalkld lglfstktlv eannehmvev rtqllqpade nwdptgtkki 1021 whcesnrsht tiakyaqyqa ssfqeslree nekrshhkdh sdsestssdn sgrrrkgpfk 1081 tikfgtnidl sddkkwklql heltklpafv rvvsagnlls hvghtilgmn tvqlymkvpg 1141 srtpghqenn nfcsvninig pgdcewfvvp egywgvlndf ceknnlnflm gswwpnledl 1201 yeanvpvyrf iqrpgdlvwi nagtvhwvga igwcnniawn vgpltacqyk laveryewnk 1261 lqsvksivpm vhlswnmarn ikvsdpklfe mikycllrtl kqcqtlreal iaagkeiiwh 1321 grtkeepahy csicevevfd llfvtnesns rktyivhcqd carktsgnle nfvvleqykm 1381 edlmqvydqf tlapplpsas s
```

By "KDM6A polynucleotide" is meant a nucleic acid molecule encoding a KDM6A polypeptide. An exemplary KDM6A polynucleotide sequence is provided at NM_001291415.1.

By "KDM6B polypeptide" (lysine-specific demethylase 6, also referred to as JmjC domain-containing protein 3) is meant a protein having at least about 85% amino acid identity to the sequence provided at NCBI Reference Sequence: O15054.4, or a fragment thereof, and having demethylase activity. An exemplary KDM6B amino acid sequence is provided below (SEQ ID NO: 2):

```
   1 mhravdppga raareafalg glscagawss cpphppprsa wlpggrcsas igqpplpapl 61 ppshgsssgh pskpyyapga ptprplhgkl eslhgcvqal lrepaqpglw eqlgqlyese 121 hdseeatrcy hsalryggsf aelgprigrl qqaqlwnfht gscqhrakvl ppleqvwnll 181 hlehkrnyga krggppvkra aeppvvqpvp paalsgpsge eglspggkrr rgcnseqtgl 241 ppglplpppp lppppppppp ppplpglat sppfqltkpg lwstlhgdaw gperkgsapp
```

-continued

```
 301 erqeqrhslp hpypypapay tahppghrlv paappgpgpr ppgaeshgcl patrppgsdl 361 resrvqrsrm dssvspaatt acvpyapsrp pglpgtttss ssssssntgl rgvepnpgip 421 gadhyqtpal evshhgrlgp sahssrkpfl gapaatphls lppgpssppp ppcprllrpp 481 pppawlkgpa craaredgei leelffgteg pprpappplp hregflgppa srfsvgtqds 541 htpptpptpt tsssnsnsgs hsssspagpvs fppppylars idplprppsp agnpqdpplv 601 pltlalppap psschontsg sfrrpesprp rvsfpktpev gpgpppgpls kapqpvppgv 661 gelpargprl fdfpptpled qfeepaefki lpdglanimk mldesirkee eqqqheagva 721 pqpplkepfa slqspfptdt aptttapava vttttttttt ttatqeeekk pppalpppppp 781 lakfpppsqp qpppppppsp asllkslasv legqkycyrg tgaavstrpg plpttqyspg 841 ppsgatalpp tsaapsaggs pqpsassssq fstsggpwar errageepvp gpmtptqppp 901 plslppparse sevleeisra cetlvervgr satdpadpvd taepadsgte rllppagake 961 eaggvaavsg sckrrqkehq kehrrhrrac kdsvgrrpre grakakakvp keksrrvlgn 1021 ldlqseeiqg reksrpdlgg askakpptap appsapapsa qptppsasvp gkkareeapg 1081 ppgvsradml klrslsegpp kelkirlikv esgdketfia seveerrlrm adltishcaa 1141 dvvrasrnak vkgkfresyl spaqsvkpki nteeklprek lnpptpsiyl eskrdafspv 1201 llqfctdprn pitvirglag slrlnlglfs tktlveasge htvevrtqvq qpsdenwdlt 1261 gtrqiwpces srshttiaky aqyqassfqe slqeekesed eeseepdstt gtppssapdp 1321 knhhiikfgt nidlsdakrw kpqlqellkl pafmrvtstg nmlshvghti lgmntvqlym 1381 kvpgsrtpgh qennnfcsvn inigpgdcew favhehywet isafcdrhgv dyltgswwpi 1441 lddlyasnip vyrfvqrpgd lvwinagtvh wvgatgwenn iawnvgplta yqyqlalery 1501 ewnevknvks ivpmihvswn vartvkisdp dlfkmikfcl lqsmkhcqvq reslvragkk 1561 iayqgrvkde payycnecdv evfnilfvts engsrntylv hcegcarrrs aglqgvvvle 1621 qyrteelaga ydaftlapas tsr
```

By "KDM6B polynucleotide" is meant a nucleic acid molecule encoding a KDM6B polypeptide. An exemplary KDM6B polynucleotide sequence is provided at NM_001080424.2 and reproduced below (SEQ ID NO: 3):

```
   1 ggcaacatgc cagccccgta gcactgccca ccccacccac tgtggtctgt tgtaccccac 61 tgctggggtg gtggttccaa tgagacaggg cacaccaaac tccatctggc tgttactgag 121 gcggagacac gggtgatgat tggctttctg gggagagagg aagtcctgtg attggccaga 181 tctctggagc ttgccgacgc ggtgtgagga cgctcccacg gaggccggaa ttggctgtga 241 aaggactgag gcagccatct gggggtagcg ggcactctta tcagagcggc tggagccgga 301 ccatcgtccc agagagctgg ggcaggggc cgtgcccaat ctccaggct cctggggcca 361 ctgctgacct ggctggatgc atcgggcagt ggaccctcca ggggcccgcg ctgcacggga 421 agcctttgcc cttgggggcc tgagctgtgc tggggcctgg agctcctgcc cgcctcatcc 481 ccctcctcgt agcgcatggc tgcctggagg cagatgctca gccagcattg ggcagccccc 541 gcttcctgct cccctacccc cttcacatgg cagtagttct gggcacccca gcaaaccata 601 ttatgctcca ggggcgccca ctccaagacc cctccatggg aagctggaat ccctgcatgg 661 ctgtgtgcag gcattgctcc gggagccagc ccagccaggg ctttgggaac agcttgggca 721 actgtacgag tcagagcacg atagtgagga ggccacacgc tgctaccaca gcgcccttcg 781 atacggagga agcttcgctg agctggggcc ccgcattggc cgactgcagc aggcccagct
```

-continued

```
 841 ctggaacttt catactggct cctgccagca ccgagccaag gtcctgcccc cactggagca 901 agtgtggaac ttgctacacc ttgagcacaa acggaactat ggagccaagc gggggaggtcc 961 cccggtgaag cgagctgctg aacccccagt ggtgcagcct gtgcctcctg cagcactctc 1021 aggcccctca ggggaggagg gcctcagccc tggaggcaag cgaaggagag gctgcaactc 1081 tgaacagact ggccttcccc cagggctgcc actgcctcca ccaccattac caccaccacc 1141 accaccacca ccaccaccac caccacccct gcctggcctg gctaccagcc ccccatttca 1201 gctaaccaag ccagggctgt ggagtaccct gcatggagat gcctggggcc cagagcgcaa 1261 gggttcagca cccccagagc gccaggagca gcggcactcg ctgcctcacc catatccata 1321 cccagctcca gcgtacaccg cgcacccccc tggccaccgg ctggtcccgg ctgctccccc 1381 aggcccaggc ccccgccccc caggagcaga gagccatggc tgcctgcctg ccacccgtcc 1441 ccccggaagt gaccttagag agagcagagt tcagaggtcg cggatggact ccagcgtttc 1501 accagcagca accaccgcct gcgtgcctta cgcccttcc cggcccctg gcctccccgg 1561 caccaccacc agcagcagca gtagcagcag cagcaacact ggtctccggg gcgtggagcc 1621 gaacccaggc attcccggcg ctgaccatta ccaaactccc gcgctggagg tctctcacca 1681 tggccgcctg gggccctcgg cacacagcag tcggaaaccg ttcttggggg ctcccgctgc 1741 cactccccac ctatccctgc cacctggacc ttcctcaccc cctccacccc cctgtccccg 1801 cctcttacgc cccccaccac cccctgcctg gttgaagggt ccggcctgcc gggcagcccg 1861 agaggatgga gagatcttag aagagctctt ctttgggact gagggacccc cccgccctgc 1921 cccaccaccc ctcccccatc gcgagggctt cttggggcct ccggcctccc gctttttctgt 1981 gggcactcag gattctcaca cccctcccac tcccccaacc ccaaccacca gcagtagcaa 2041 cagcaacagt ggcagccaca gcagcagccc tgctgggcct gtgtcctttc ccccaccacc 2101 ctatctggcc agaagtatag accccttcc ccggcctccc agcccagcac agaaccccca 2161 ggacccacct cttgtacccc tgactcttgc cctgcctcca gcccctcctt cctcctgcca 2221 ccaaaatacc tcaggaagct tcaggcgccc ggagagcccc cggcccaggg tctccttccc 2281 aaagaccccc gaggtggggc cggggccacc cccaggcccc ctgagtaaag cccccccagcc 2341 tgtgccgccc ggggttgggg agctgcctgc ccgaggccct cgactctttg attttccccc 2401 cactccgctg gaggaccagt ttgaggagcc agccgaattc aagatcctac ctgatgggct 2461 ggccaacatc atgaagatgc tggacgaatc cattcgcaag gaagaggaac agcaacaaca 2521 cgaagcaggc gtggcccccc aacccccgct gaaggagccc tttgcatctc tgcagtctcc 2581 tttccccacc gacacagccc ccaccactac tgctcctgct gtcgccgtca ccaccaccac 2641 caccaccacc accaccacca cggccaccca ggaagaggag aagaagccac caccagccct 2701 accaccacca ccgcctctag ccaagttccc tccaccctct cagccacagc caccaccacc 2761 cccacccccc agcccggcca gcctgctcaa atccttggcc tccgtgctgg agggacaaaa 2821 gtactgttat cgggggactg gagcagctgt ttccacccgg cctgggccct tgcccaccac 2881 tcagtattcc cctggccccc catcaggtgc taccgccctg ccgcccacct cagcggcccc 2941 tagcgcccag ggctccccac agccctctgc ttcctcgtca tctcagttct ctacctcagg 3001 cgggccctgg gccgggagc gcagggcggg cgaagagcca gtcccgggcc ccatgacccc 3061 cacccaaccg cccccacccc tatctctgcc ccctgctcgc tctgagtctg aggtgctaga 3121 agagatcagc cgggcttgcg agacccttgt ggagcgggtg ggccggagtg ccactgaccc 3181 agccgaccca gtggacacag cagagccagc ggacagtggg actgagcgac tgctgccccc 3241 cgcacaggcc aaggaggagg ctggcgggt ggcggcagtg tcaggcagct gtaagcggcg
```

-continued

```
3301 acagaaggag catcagaagg agcatcggcg gcacaggcgg gcctgtaagg acagtgtggg 3361 tcgtcggccc cgtgagggca gggcaaaggc caaggccaag gtccccaaag aaaagagccg 3421 ccgggtgctg gggaacctgg acctgcagag cgaggagatc cagggtcgtg agaagtcccg 3481 gcccgatctt ggcggggcct ccaaggccaa gccacccaca gctccagccc ctccatcagc 3541 tcctgcacct tctgcccagc ccacaccccc gtcagcctct gtccctggaa agaaggctcg 3601 ggaggaagcc ccagggccac cgggtgtcag ccgggccgac atgctgaagc tgcgctcact 3661 tagtgagggg cccccccaagg agctgaagat ccggctcatc aaggtagaga gtggtgacaa 3721 ggagaccttt atcgcctctg aggtggaaga gcggcggctg cgcatggcag acctcaccat 3781 cagccactgt gctgctgacg tcgtgcgcgc cagcaggaat gccaaggtga aagggaagtt 3841 tcgagagtcc tacctttccc ctgcccagtc tgtgaaaccg aagatcaaca ctgaggagaa 3901 gctgccccgg gaaaaactca acccccctac acccagcatc tatctggaga gcaaacggga 3961 tgccttctca cctgtcctgc tgcagttctg tacagaccct cgaaatccca tcacagtgat 4021 ccgggggcctg gcgggctccc tgcggctcaa cttgggcctc ttctccacca agaccctggt 4081 ggaagcgagt ggcgaacaca ccgtggaagt tcgcacccag gtgcagcagc cctcagatga 4141 gaactgggat ctgacaggca ctcggcagat ctggccttgt gagagctccc gttcccacac 4201 caccattgcc aagtacgcac agtaccaggc ctcatccttc caggagtctc tgcaggagga 4261 gaaggagagt gaggatgagg agtcagagga gccagacage accactggaa cccctcctag 4321 cagcgcacca gacccgaaga accatcacat catcaagttt ggcaccaaca tcgacttgtc 4381 tgatgctaag cggtggaagc cccagctgca ggagctgctg aagctgcccg ccttcatgcg 4441 ggtaacatcc acgggcaaca tgctgagcca cgtgggccac accatcctgg gcatgaacac 4501 ggtgcagctg tacatgaagg tgcccggcag ccgaacgcca ggccaccagg agaataacaa 4561 cttctgctcc gtcaacatca acattggccc aggcgactgc gagtggttcg cggtgcacga 4621 gcactactgg gagaccatca gcgctttctg tgatcggcac ggcgtggact acttgacggg 4681 ttcctggtgg ccaatcctgg atgatctcta tgcatccaat attcctgtgt accgcttcgt 4741 gcagcgaccc ggagacctcg tgtggattaa tgcggggact gtgcactggg tgcaggccac 4801 cggctggtgc aacaacattg cctggaacgt ggggcccctc accgcctatc agtaccagct 4861 ggccctggaa cgatacgagt ggaatgaggt gaagaacgtc aaatccatcg tgcccatgat 4921 tcacgtgtca tggaacgtgg ctcgcacggt caaaatcagc gacccccgact tgttcaagat 4981 gatcaagttc tgcctgctgc agtccatgaa gcactgccag gtgcaacgcg agagcctggt 5041 gcgggcaggg aagaaaatcg cttaccaggg ccgtgtcaag gacgagccag cctactactg 5101 caacgagtgc gatgtggagg tgtttaacat cctgttcgtg acaagtgaga atggcagccg 5161 caacacgtac ctggtacact gcgagggctg tgcccggcgc cgcagcgcag gcctgcaggg 5221 cgtggtggtg ctggagcagt accgcactga ggagctggct caggcctacg acgccttcac 5281 gctggtgagg gcccggcggg cgcgcgggca gcggaggagg gcactggggc aggctgcagg 5341 gacgggcttc gggagcccgg ccgcgccttt ccctgagccc ccgccggctt tctccccca 5401 ggccccagcc agcacgtcgc gatgaggccg gacgccccgc ccgcctgcct gcccgcgcaa 5461 ggcgccgcgg ggccaccagc acatgcctgg gctggaccta ggtcccgcct gtggccgaga 5521 aggggtcgg gcccagccct tccacccat tggcagctcc cctcacttaa tttattaaga 5581 aaaacttttt ttttttttt agcaaatatg aggaaaaaag gaaaaaaat gggagacggg 5641 ggaggggct ggcagcccct cgcccaccag cgcctcccct caccgacttt ggccttttta
```

12

-continued

```
5701 gcaacagaca caaggaccag gctccggcgg cggcgggggt cacatacggg ttccctcacc 5761 ctgccagccg cccgcccgcc cggcgcagat gcacgcggct cgtgtatgta catagacgtt 5821 acggcagccg aggttttaa tgagattctt tctatgggct ttaccccctcc cccggaacct 5881 ccttttttac ttccaatgct agctgtgacc cctgtacatg tctctttatt cacttggtta 5941 tgatttgtat ttttttgttct tttcttgttt ttttgttttt aatttataac agtcccactc 6001 acctctattt attcatttt gggaaaaccc gacctcccac accccaagc catcctgccc 6061 gcccctccag ggaccgcccg tcgccgggct ctccccgcgc cccagtgtgt gtccgggccc 6121 ggcccgaccg tctccacccg tccgcccgcg gctccagccg ggttctcatg gtgctcaaac 6181 ccgctcccct cccctacgtc ctgcactttc toggaccagt cccccacte ccgacccgac 6241 cccagcccca cctgagggtg agcaactct gtactgtagg ggaagaagtg ggaactgaaa 6301 tggtattttg taaaaaaaat aaataaaata aaaaattaa aggttttaaa gaaagaacta 6361 tgaggaaaag gaaccccgtc cttcccagcc ccggccaact ttaaaaaaca cagaccttca 6421 cccccacccc cttttcttt taagtgtgaa acaacccagg gccagggcct cactgggca 6481 gggacacccc gggtgagtt tctctggggc tttattttcg ttttgttggt tgttttttct 6541 ccacgctggg gctgcggagg ggtggggggt ttacagtccc gcaccctcgc actgcactgt 6601 ctctctgccc caggggcaga ggggtcttcc caaccctacc cctattttcg gtgattttg 6661 tgtgagaata ttaatattaa aaataaacgg agaaaaaaa aaaaaaaaaa aaaaaaaaa 6721 aaaaaaaaa a
```

By "KDM6C polypeptide" (histone demethylase UTY, also referred to as ubiquitously-transcribed TPR protein on the Y chromosome) is meant a protein having at least about 85% amino acid identity to the sequence provided at NCBI Reference Sequence: O14607.2, or a fragment thereof, and having demethylase activity. An exemplary KDM6C amino acid sequence is provided below (SEQ ID NO: 4):

```
  1 mkscavsltt aavafgdeak kmaegkasre seeesvsltv eerealggmd srlfgfvrlh 61 edgartktll gkavrcyesl ilkaegkves dffcqlghfn llledyskal saygryyslq 121 adywknaafl yglglvyfyy nafhwaikaf qdvlyvdpsf crakeihlrl glmfkvntdy 181 ksslkhfqla lidcnpctls naeiqfhiah lyetqrkyhs akeayeqllq tenlpaqvka 241 tvlqqlgwmh hnmdlvgdka tkesyaiqyl qksleadpns gqswyflgrc yssigkvqda 301 fisyrqsidk seasadtwcs igvlyqqqnq pmdalqayic avqldhghaa awmdlgtlye 361 scnqpqdaik cylnaarskr csntstlaar ikflqngsdn wnggqslshh pvqqvyslcl 421 tpqklqhleq lranrdnlnp aqkhqleqle sqfvlmqqmr hkevaqvrtt gihngaitds 481 slptnsvsnr qphgaltrvs svsqpgvrpa cvekllssga fsagcipcgt skilgstdti 541 llgsnciags esngnvpylq qnthtlphnh tdlnssteep wrkqlsnsaq glhksqsscl 601 sgpneeqplf stgsaqyhqa tstgikkane hltlpsnsvp qgdadshlsc htatsggqqg 661 imftkeskps knrslvpets rhtgdtsngc advkglsnhv hqliadavss pnhgdspnll 721 iadnpqlsal ligkangnvg tgtcdkvnni hpavhtktdh svasspssai statpspkst 781 eqrsinsvts Insphsglht vngeglgksq sstkvdlpla shrstsqilp smsvsicpss 841 tevlkacrnp gknglsnsci lldkcppprp ptspypplpk dklnpptpsi ylenkrdaff 901 pplhqfctnp knpvtvirgl agalkldlgl fstktlvean nehmvevrtq llqpadenwd 961 ptgtkkiwrc esnrshttia kyaqyqassf qeslreenek rtqhkdhsdn estssensgr
```

-continued

```
1021 rrkgpfktik fgtnidlsdn kkwklqlhel tklpafarvv sagnllthvg htilgmntvq 1081 lymkvpgsrt pghqennnfc svninigpgd cewfvvpedy wgvindfcek nnlnflmssw 1141 wpnledlyea nvpvyrfiqr pgdlvwinag tvhwvqavgw cnniawnvgp ltacqyklav 1201 eryewnklks vkspvpmvhl swnmarnikv sdpklfemik ycllkilkqy qtlrealvaa 1261 gkeviwhgrt ndepahycsi cevevfnllf vtnesntqkt yivhchdcar ktskslenfv 1321 vleqykmedl iqvydqftla lslssss
```

By "KDM6C polynucleotide is meant a nucleic acid molecule encoding a KDM6C polypeptide. An exemplary KDM6A polynucleotide sequence is provided at NM_001258249.1, which sequence is reproduced below (SEQ ID NO: 5):

```
   1 gctcatcgtt tgttgtttag ataatatcat gaactgataa atgcagttgc cacgttgatt 61 ccctagggcc tggcttaccg actgaggtca taagatatta tgccttctct ttagacttgg 121 tcagtggaga ggaaatgggc aaagaaccag cctatggagg tgacaaggcc ttagggccaa 181 aagtcttgag ggtgaaggtt tagggcctgc gcagcttccc tgccatgccc cgcaaggtct 241 cgcattcgca aggcttgtga cagtgggagc ctcattacgg actctcctaa agtccatggt 301 gtcctctttt cgcatttgcg ccccgtgggg gatgcccgat gccgcccttc ccatcgctct 361 cttccccttc aagcgtatcg caactgcaaa aacacccagc acagacactc cattttctat 421 cttaatgcat ttaactagca caacctacag gttgttccat cccagagact acccttttct 481 ccatagacgt gaccatcaac caaccagcgg tcagaatcag tcagcctctg tcatgttcct 541 aggtccttgg cgaactggct gggcggggtc ccagcagcct aggagtacag tggagcaatg 601 cctgacgtaa gtcaacaaag atcacgtgag acgaatcagt cgcctagatt ggctacaact 661 aagtggttgg gagcggggag gtcgcggcgg ctgcgtgggg ttcgcccgtg acacaattac 721 aactttgtgc tggtgctggc aaagtttgtg attttaagaa attctgctgt gctctccagc 781 actgcgagct tctgccttcc ctgtagtttc ccagatgtga tccaggtagc cgagttccgc 841 tgcccgtgct tcggtagctt aagtctttgc ctcagctttt ttccttgcag ccgctgagga 901 ggcgataaaa ttggcgtcac agtctcaagc agcgattgaa ggcgtctttt caactactcg 961 attaaggttg ggtatcgtcg tgggacttgg aaatttgttg tttccatgaa atcctgcgca 1021 gtgtcgctca ctaccgccgc tgttgccttc ggtgatgagg caaagaaaat ggcggaagga 1081 aaagcgagcc gcgagagtga agaggagtct gttagcctga cagtcgagga aagggaggcg 1141 cttggtggca tggacagccg tctcttcggg ttcgtgaggc ttcatgaaga tggcgccaga 1201 acgaagaccc tactaggcaa ggctgttcgc tgctacgaat ctttaatctt aaaagctgaa 1261 ggaaaagtgg agtctgactt cttttgccaa ttaggtcact tcaacctctt gttggaagat 1321 tattcaaaag cattatctgc atatcagaga tattacagtt tacaggctga ctactggaag 1381 aatgctgcgt ttttatatgg ccttggtttg gtctacttct actacaatgc atttcattgg 1441 gcaattaaag catttcaaga tgtcctttat gttgacccca gcttttgtcg agccaaggaa 1501 attcatttac gacttgggct catgttcaaa gtgaacacag actacaagtc tagtttaaag 1561 cattttcagt tagccttgat tgactgtaat ccatgtactt tgtccaatgc tgaaattcaa 1621 tttcatattg cccatttgta tgaaacccag aggaagtatc attctgcaaa ggagggcatat 1681 gaacaacttt tgcagacaga aaaccttcct gcacaagtaa aagcaactgt attgcaacag 1741 ttaggttgga tgcatcataa tatggatcta gtaggagaca aagccacaaa ggaaagctat
```

-continued

```
1801 gctattcagt atctccaaaa gtctttggag gcagatccta attctggcca atcgtggtat 1861 tttcttggaa ggtgttattc aagtattggg aaagttcagg atgcctttat atcttacagg 1921 caatctattg ataaatcaga agcaagtgca gatacatggt gttcaatagg tgtgttgtat 1981 cagcagcaaa atcagcctat ggatgcttta caggcatata tttgtgctgt acaattggac 2041 catgggcatg ccgcagcctg gatggaccta ggtactctct atgaatcctg caatcaacct 2101 caagatgcca ttaaatgcta cctaaatgca gctagaagca aacgttgtag taatacctct 2161 acgcttgctg caagaattaa atttctacag gctcagttgt gtaaccttcc acaaagtagt 2221 ctacagaata aaactaaatt acttcctagt attgaggagg catggagcct accaatcccc 2281 gcagagctta cctccaggca gggtgccatg aacacagcac agcaggctta tagagctcat 2341 gatccaaata ctgaacatgt attaaaccac agtcaaacac caattttaca gcaatccttg 2401 tcactacaca tgattacttc tagccaagta gaaggcctgt ccagtcctgc caagaagaaa 2461 agaacatcta gtccaacaaa gaatggttct gataactgga atggtggcca gagtctttca 2521 catcatccag tacagcaagt ttattcgttg tgtttgacac cacagaaatt acagcacttg 2581 gaacaactgc gagcaaatag agataattta aatccagcac agaagcatca gctggaacag 2641 ttagaaagtc agtttgtctt aatgcagcaa atgagacaca aagaagttgc tcaggtacga 2701 actactggaa ttcataacgg ggccataact gattcatcac tgcctacaaa ctctgtctct 2761 aatcgacaac cacatggtgc tctgaccaga gtatctagcg tctctcagcc tggagttcgc 2821 cctgcttgtg ttgaaaaact tttgtccagt ggagctttt ctgcaggctg tattccttgt 2881 ggcacatcaa aaattctagg aagtacagac actatcttgc taggcagtaa ttgtatagca 2941 ggaagtgaaa gtaatggaaa tgtgccttac ctgcagcaaa atacacacac tctacctcat 3001 aatcatacag acctgaacag cagcacagaa gagccatgga gaaaacagct atctaactcc 3061 gctcaggggc ttcataaaag tcagagttca tgtttgtcag gacctaatga agaacaacct 3121 ctgtttttcca ctgggtcagc ccagtatcac caggcaacta gcactggtat taagaaggcg 3181 aatgaacatc tcactctgcc tagtaattca gtaccacagg gggatgctga cagtcacctc 3241 tcctgtcata ctgctacctc aggtggacaa caaggcatta tgtttaccaa agagagcaag 3301 ccttcaaaaa atagatcctt ggtgcctgaa acaagcaggc atactggaga cacatctaat 3361 ggctgtgctg atgtcaaggg actttctaat catgttcatc agttgatagc agatgctgtt 3421 tccagtccta accatggaga ttcaccaaat ttattaattg cagacaatcc tcagctctct 3481 gctttgttga ttggaaaagc caatggcaat gtgggtactg gaacctgtga caaagtgaat 3541 aatattcacc cagctgttca tacaaagact gatcattctg ttgcctcttc accctcttca 3601 gccatttcca cagcaacacc ttctcctaaa tccactgagc agagaagcat aaacagtgtt 3661 accagcctta acagtcctca cagtggatta cacacagtca atggagaggg gctggggaag 3721 tcacagagct ctacaaaagt agacctgcct ttagctagcc acagatctac ttctcagatc 3781 ttaccatcaa tgtcagtgtc tatatgcccc agttcaacag aagttctgaa agcatgcagg 3841 aatccaggta aaaatggctt gtctaatagc tgcattttgt tagataaatg tccacctcca 3901 agaccaccaa cttcaccata cccacccttg ccaaaggaca agttgaatcc acccacacct 3961 agtatttact tggaaaataa acgtgatgct ttctttcctc cattcatca attttgtaca 4021 aatccaaaaa accctgttac agtaatacgt ggccttgctg gagctcttaa attagatctt 4081 ggacttttct ctaccaaaac tttggtagaa gctaacaatg aacatatggt agaagtgagg 4141 acacagttgc tgcaaccagc agatgaaaac tgggatccca ctggaacaaa gaaaatctgg
```

-continued

```
4201 cgttgtgaaa gcaatagatc tcatactaca attgccaaat acgcacaata ccaggcttcc 4261 tccttccagg aatcattgag agaagaaaat gagaaaagaa cacaacacaa agatcattca 4321 gataacgaat ccacatcttc agagaattct ggaaggagaa ggaaaggacc tttttaaaacc 4381 ataaaatttg ggaccaacat tgacctctct gataacaaaa agtggaagtt gcagttacat 4441 gaactgacta aacttcctgc ttttgcgcgt gtggtgtcag caggaaatct tctaacccat 4501 gttgggcata ccattctggg catgaataca gtacaactgt atatgaaagt tccagggagt 4561 cggacaccag gtcaccaaga aaataacaac ttctgctctg ttaacataaa tattggtcca 4621 ggagattgtg aatggtttgt tgtacctgaa gattattggg gtgttctgaa tgacttctgt 4681 gaaaaaaata atttgaattt tttaatgagt tcttggtggc ccaaccttga agatctttat 4741 gaagcaaatg tccctgtgta tagatttatt cagcgacctg agatttggt ctggataaat 4801 gcaggcactg tgcattgggt tcaagctgtt ggctggtgca ataacattgc ctggaatgtt 4861 ggtccactta cagcctgcca gtataaattg gcagtggaac ggtatgaatg gaacaaattg 4921 aaaagtgtga agtcaccagt acccatggtg catctttcct ggaatatggc acgaaatatc 4981 aaagtctcag atccaaagct ttttgaaatg attaagtatt gtcttttgaa aattctgaag 5041 caatatcaga cattgagaga agctcttgtt gcagcaggaa aagaggttat atggcatggg 5101 cggacaaatg atgaaccagc tcattactgt agcatttgtg aggtggaggt ttttaatctg 5161 ctttttgtca ctaatgaaag caatactcaa aaaacctaca tagtacattg ccatgattgt 5221 gcacgaaaaa caagcaaaag tttggaaaat tttgtggtgc tcgaacagta caaaatggag 5281 gacctaatcc aagtttatga tcaatttaca ctagctcttt cattatcatc ctcatcttga 5341 tatagttcca tgaatattaa atgagattat ttctgctctt caggaaattt ctgcaccact 5401 ggttttgtag ctgtttcata aaactgttga ctaaaagcta tgtctatgca accttccaag 5461 aatagtatgt caagcaactg gacacagtgc tgcctctgct tcaggactta acatgctgat 5521 ccagctgtac ttcagaaaaa taatattaat catatgtttt gtgtacgtat gacaaactgt 5581 caaagtgaca cagaatactg atttgaagat agcctttttt atgtttctct atttctgggc 5641 tgatgaatta atattcattt gtattttaac cctgcagaat tttccttagt taaaaacact 5701 ttcctagctg gtcatttctt cataagatag caaatttaaa tctctcctcg atcagctttt 5761 aaaaaatgtg tactattatc tgaggaagtt ttttactgct ttatgttttt gtgtgttttg 5821 aggccatgat gattacattt gtggttccaa aataattttt ttaaatatta atagcccata 5881 tacaaagata atggattgca catagacaaa gaaataaact tcagatttgt gattttttgtt 5941 tctaaacttg atacagattt acactattta taaatacgta tttattgcct gaaaatattt 6001 gtgaatggaa tgttgttttt ttccagacgt aactgccatt aaatactaag gagttctgta 6061 gttttaaaaca ctactcctat tacatttat atgtgtagat aaaactgctt agtattatac 6121 agaaattttt attaaaattg ttaaatgttt aaagggtttc ccaatgtttg agtttaaaaa 6181 agactttctg aaaaaatcca cttttttgttc attttcaaac ctaatgatta tatgtatttt 6241 atatgtgtgt gtatgtgtac acacatgtat aatatataca gaaacctcga tatataattg 6301 tatagatttt aaaagtttta tttttttacat ctatggtagt ttttgaggtg cctattataa 6361 agtattacgg aagtttgctg tttttaaagt aaatgtcttt tagtgtgatt tattaagttg 6421 tagtcaccat agtgatagcc cataaataat tgctggaaaa ttgtatttta taacagtaga 6481 aaacatatag tcagtgaagt aaatatttta aaggaaacat tatatagatt tgataaatgt 6541 tgtttataat taagagtttc ttatggaaaa gagattcaga atgataacct cttttagaga 6601 acaaataagt gacttatttt tttaaagcta gatgactttg aaatgctata ctgtcctgct
```

```
6661 tgtacaacat ggtttggggt gaaggggagg aaagtattaa aaaatctata tcgctagtaa 6721 attgtaataa gttctattaa aacttgtatt tcatatgaaa aatttgctaa tttaatatta 6781 actcatttga taataatact tgtcttttct acctctc
```

By "tri-methylated histone H3 at lysine 27 (H3K27me3)" is meant the trimethylation of lysine 27 on histone H3 protein subunit. The H3K27me3 modification is generally associated with gene repression.

By "agent" is meant a peptide, nucleic acid molecule, or small compound.

By "allele" is meant one of two or more alternative forms of a gene that are found at the same place on a chromosome.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

The term "blastula" as used herein refers to an early stage in the development of an embryo consisting of a hollow sphere of cells enclosing a fluid-filled cavity called the blastocoel. The term blastula sometimes is used interchangeably with blastocyst.

The term "blastomere" is used throughout to refer to at least one blastomere (e.g., 1, 2, 3, 4, etc.) obtained from a preimplantation embryo. The term "cluster of two or more blastomeres" is used interchangeably with "blastomere-derived outgrowths" to refer to the cells generated during the in vitro culture of a blastomere. For example, after a blastomere is obtained from a SCNT embryo and initially cultured, it generally divides at least once to produce a cluster of two or more blastomeres (also known as a blastomere-derived outgrowth). The cluster can be further cultured with embryonic or fetal cells. Ultimately, the blastomere-derived outgrowths will continue to divide. From these structures, ES cells, totipotent stem (TS) cells, and partially differentiated cell types will develop over the course of the culture method.

The term "cloned (or cloning)" as used herein refers to a gene manipulation technique for preparing a new individual unit to have a gene set identical to another individual unit. In the present invention, the term "cloned" as used herein refers to a cell, embryonic cell, fetal cell, and/or animal cell has a nuclear DNA sequence that is substantially similar or identical to the nuclear DNA sequence of another cell, embryonic cell, fetal cell, differentiated cell, and/or animal cell. The terms "substantially similar" and "identical" are described herein. The cloned SCNT embryo can arise from one nuclear transfer, or alternatively, the cloned SCNT embryo can arise from a cloning process that includes at least one re-cloning step.

In this disclosure, "comprises," "comprising." "containing" and "having" and the like can have the meaning ascribed to them in U.S. Patent law and can mean "includes," "including," and the like: "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages, or interferes with the normal function or development of a cell, tissue, or organ. Examples of disorders include defects (e.g., developmental defects, loss of viability) associated with the disruption of X chromosome imprinting in an embryo.

By "DNA" is meant deoxyribonucleic acid. In various embodiments, the term DNA refers to genomic DNA, recombinant DNA, or cDNA. In particular embodiments, the DNA comprises a "target region." DNA libraries contemplated herein include genomic DNA libraries, and cDNA libraries constructed from RNA, e.g., an RNA expression library. In various embodiments, the DNA libraries comprise one or more additional DNA sequences and/or tags.

By "effective amount" is meant the amount of an agent required to restore a cell to a physiologically normal condition. In one embodiment, an effective amount of the agent is the amount required to correct an imprinting defect and to impart a physiologically normal imprinting phenotype to the cell. In one embodiment, the injection of Kdm6b mRNA is sufficient to correct an imprinting defect associated with abnormal and/or undesirable X chromosome inactivation. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "embryo" is meant

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector: into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity." to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl. G. M. and S. L. Berger (1987) Methods Enzymol. 152:399; Kimmel. A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C. more preferably of at least about 37° C. and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 mu·g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C. and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975): Ausubel et al. (Current Protocols in Molecular Biology, Wiley Interscience, New York, 2001): Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "Somatic Cell Nuclear Transfer" or "SCNT" is meant the transfer of a donor nucleus from a somatic cell into an enucleated oocyte. The process can be used in either reproductive or therapeutic cloning and may be accomplished by fusion of the somatic cell with the enucleated oocyte, injection of the nucleus into the enucleated oocyte, or by any other method.

The nucleus of the somatic cell provides the genetic information, while the oocyte provides the nutrients and other energy-producing materials that are necessary for development of an embryo. Once fusion has occurred, the cell is totipotent, and eventually develops into a blastocyst, at which point the inner cell mass is isolated.

The term "nuclear transfer" as used herein refers to a gene manipulation technique allowing an identical characteristics and qualities acquired by artificially combining an enucleated oocytes with a cell nuclear genetic material or a nucleus of a somatic cell. In some embodiments, the nuclear transfer procedure is where a nucleus or nuclear genetic material from a donor somatic cell is transferred into an enucleated egg or oocyte (an egg or oocyte from which the nucleus/pronuclei have been removed). The donor nucleus can come from a somatic cell.

The term "nuclear genetic material" refers to structures and/or molecules found in the nucleus which comprise polynucleotides (e.g., DNA) which encode information about the individual. Nuclear genetic material includes the chromosomes and chromatin. The term also refers to nuclear genetic material (e.g., chromosomes) produced by cell division such as the division of a parental cell into daughter cells. Nuclear genetic material does not include mitochondrial DNA.

The term "SCNT embryo" refers to a cell, or the totipotent progeny thereof, of an enucleated oocyte which has been fused with the nucleus or nuclear genetic material of a somatic cell. The SCNT embryo can develop into a blastocyst and develop post-implantation into living offspring. The SCNT embryo can be a 1-cell embryo, 2-cell embryo, 4-cell embryo, or any stage embryo prior to becoming a blastocyst.

The term "donor human cell" or "donor human somatic cell" refers to a somatic cell or a nucleus of human cell which is transferred into a recipient oocyte as a nuclear acceptor or recipient.

The term "somatic cell" refers to a plant or animal cell which is not a reproductive cell or reproductive cell precursor. In some embodiments, a differentiated cell is not a germ cell. A somatic cell does not relate to pluripotent or totipotent cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

The term "oocyte" as used herein refers to a mature oocyte which has reached metaphase II of meiosis. An oocyte is also used to describe a female gamete or germ cell involved in reproduction, and is commonly also called an egg. A mature egg has a single set of maternal chromosomes (23, X in a human primate) and is halted at metaphase II.

A "hybrid oocyte" refers to an enucleated oocyte that has the cytoplasm from a first human oocyte (termed a "recipient") but does not have the nuclear genetic material of the recipient oocyte: it has the nuclear genetic material from another human cell, termed a "donor." In some embodiments, the hybrid oocyte can also comprise mitochondrial DNA (mtDNA) that is not from the recipient oocyte, but is from a donor cell (which can be the same donor cell as the nuclear genetic material, or from a different donor, e.g., from a donor oocyte).

The term "enucleated oocyte" as used herein refers to an human oocyte which its nucleus has been removed.

The term "enucleation" as used herein refers to a process whereby the nuclear material of a cell is removed, leaving only the cytoplasm. When applied to an egg, enucleation refers to the removal of the maternal chromosomes, which are not surrounded by a nuclear membrane. The term "enucleated oocyte" refers to an oocyte where the nuclear material or nuclei is removed.

The "recipient human oocyte" as used herein refers to a human oocyte that receives a nucleus from a human nuclear donor cell after removing its original nucleus.

The term "fusion" as used herein refers to a combination of a nuclear donor cell and a lipid membrane of a recipient oocyte. For example, the lipid membrane may be the plasma membrane or nuclear membrane of a cell. Fusion may occur upon application of an electrical stimulus between a nuclear donor cell and a recipient oocyte when they are placed adjacent to each other or when a nuclear donor cell is placed in a perivitelline space of a recipient oocyte.

The term "living offspring" as used herein means an animal that can survive ex utero. Preferably, it is an animal that can survive for one second, one minute, one day, one week, one month, six months or more than one year. The animal may not require an in utero environment for survival.

The term "prenatal" refers to existing or occurring before birth. Similarly, the term "postnatal" is existing or occurring after birth.

The term "transgenic organism" as used herein refers to an organism into which genetic material from another organism has been experimentally transferred, so that the host acquires the genetic traits of the transferred genes in its chromosomal composition.

The term "implanting" as used herein in reference to SCNT embryos as disclosed herein refers to impregnating a surrogate female animal with a SCNT embryo described herein. This technique is well known to a person of ordinary skill in the art. See, e.g., Seidel and Elsden, 1997, Embryo Transfer in Dairy Cattle, W. D. Hoard & Sons, Co., Hoards Dairyman. The embryo may be allowed to develop in utero, or alternatively, the fetus may be removed from the uterine environment before parturition.

By "subject" is meant a mammal, including, but not limited to, a human or non-human mammal, such as an agriculturally significant mammal (e.g., bovine, equine, ovine, porcine), a pet (e.g., canine, feline), or a rare or endangered mammal (e.g., panda).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "Somatic Cell Nuclear Transfer" or "SCNT" is meant the transfer of a donor nucleus from a somatic cell into an enucleated oocyte. The process can be used in either reproductive or therapeutic cloning and may be accomplished by fusion of the somatic cell with the enucleated oocyte, injection of the nucleus into the enucleated oocyte, or by any other method.

The nucleus of the somatic cell provides the genetic information, while the oocyte provides the nutrients and other energy-producing materials that are necessary for development of an embryo. Once fusion has occurred, the cell is totipotent, and eventually develops into a blastocyst, at which point the inner cell mass is isolated.

The term "nuclear transfer" as used herein refers to a gene manipulation technique allowing an identical characteristics and qualities acquired by artificially combining an enucleated oocytes with a cell nuclear genetic material or a nucleus of a somatic cell. In some embodiments, the nuclear transfer procedure is where a nucleus or nuclear genetic material from a donor somatic cell is transferred into an enucleated egg or oocyte (an egg or oocyte from which the nucleus/ pronuclei have been removed). The donor nucleus can come from a somatic cell.

The term "nuclear genetic material" refers to structures and/or molecules found in the nucleus which comprise polynucleotides (e.g., DNA) which encode information about the individual. Nuclear genetic material includes the chromosomes and chromatin. The term also refers to nuclear genetic material (e.g., chromosomes) produced by cell division such as the division of a parental cell into daughter cells. Nuclear genetic material does not include mitochondrial DNA.

The term "SCNT embryo" refers to a cell, or the totipotent progeny thereof, of an enucleated oocyte, which has been fused with the nucleus or nuclear genetic material of a somatic cell. The SCNT embryo can develop into a blastocyst and develop post-implantation into living offspring. The SCNT embryo can be a 1-cell embryo, 2-cell embryo, 4-cell embryo, or any stage embryo prior to becoming a blastocyst.

The term "donor human cell" or "donor human somatic cell" refers to a somatic cell or a nucleus of human cell that is transferred into a recipient oocyte as a nuclear acceptor or recipient.

The term "somatic cell" refers to an animal cell, which is not a reproductive cell or reproductive cell precursor. In some embodiments, a differentiated cell is not a germ cell. A somatic cell does not relate to pluripotent or totipotent cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

The term "oocyte" as used herein refers to a mature oocyte which has reached metaphase II of meiosis. An oocyte is also used to describe a female gamete or germ cell involved in reproduction, and is commonly also called an egg. A mature egg has a single set of maternal chromosomes (23, X in a human primate) and is halted at metaphase II.

A "hybrid oocyte" refers to an enucleated oocyte that has the cytoplasm from a first human oocyte (termed a "recipient") but does not have the nuclear genetic material of the recipient oocyte: it has the nuclear genetic material from another human cell, termed a "donor." In some embodiments, the hybrid oocyte can also comprise mitochondrial DNA (mtDNA) that is not from the recipient oocyte, but is from a donor cell (which can be the same donor cell as the nuclear genetic material, or from a different donor, e.g., from a donor oocyte).

The term "enucleated oocyte" as used herein refers to an human oocyte whose nucleus has been removed.

The term "enucleation" as used herein refers to a process whereby the nuclear material of a cell is removed, leaving only the cytoplasm. When applied to an egg, enucleation refers to the removal of the maternal chromosomes, which are not surrounded by a nuclear membrane.

The "recipient human oocyte" as used herein refers to a human oocyte that receives a nucleus from a human nuclear donor cell after removing its original nucleus.

The term "fusion" as used herein refers to a combination of a nuclear donor cell and a lipid membrane of a recipient oocyte. For example, the lipid membrane may be the plasma membrane or nuclear membrane of a cell. Fusion may occur upon application of an electrical stimulus between a nuclear donor cell and a recipient oocyte when they are placed adjacent to each other or when a nuclear donor cell is placed in a perivitelline space of a recipient oocyte.

The term "living offspring" as used herein means an animal that can survive ex utero. Preferably, it is an animal that can survive for one or more hours, one day, one week, one month, six months or more than one year. The animal may not require an in utero environment for survival.

The term "prenatal" refers to existing or occurring before birth. Similarly, the term "postnatal" is existing or occurring after birth.

The term "blastocyst" as used herein refers to a preimplantation embryo in placental mammals (about 3 days after fertilization in the mouse, about 5 days after fertilization in humans) of about 30-150 cells. The blastocyst stage follows the morula stage, and can be distinguished by its unique morphology. The blastocyst consists of a sphere made up of a layer of cells (the trophectoderm), a fluid-filled cavity (the blastocoel or blastocyst cavity), and a cluster of cells on the interior (the inner cell mass, or ICM). The ICM, consisting of undifferentiated cells, gives rise to what will become the fetus if the blastocyst is implanted in a uterus. These same ICM cells, if grown in culture, can give rise to embryonic stem cell lines. At the time of implantation the mouse blastocyst is made up of about 70 trophoblast cells and 30 ICM cells.

The term "transgenic organism" as used herein refers to an organism into which genetic material from another organism has been experimentally transferred, so that the host acquires the genetic traits of the transferred genes in its chromosomal composition.

The term "implanting" as used herein in reference to SCNT embryos as disclosed herein refers to impregnating a surrogate female animal with a SCNT embryo described herein. This technique is well known to a person of ordinary skill in the art. See, e.g., Seidel and Elsden, 1997, Embryo Transfer in Dairy Cattle, W. D. Hoard & Sons, Co., Hoards Dairyman. The embryo may be allowed to develop in utero, or alternatively, the fetus may be removed from the uterine environment before parturition.

By "subject" is meant a mammal, including, but not limited to, a human or non-human mammal, such as an agriculturally significant mammal (e.g., bovine, equine, ovine, porcine), a pet (e.g., canine, feline), or a rare or endangered mammal (e.g., panda).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. In one embodiment, the term "treating" refers to the treatment of imprinting defects in SCNT embryos.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "or" is understood to be inclusive. Unless specifically stated or obvious from context, as used herein, the terms "a", "an", and "the" are understood to be singular or plural (i.e., at least one). By way of example, "an element" means one element or more than one element.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A depicts representative images of zygotes stained with anti-H3K9me3 antibody. (M) Maternal pronucleus: (P) paternal pronucleus. The bar graph shows relative H3K9me3 signal intensity of the maternal pronuclei. The average signal intensity of noninjected zygotes was set as 1.0. The total numbers of embryos examined were eight (no injection), nine (1000 ng/μL Kdm4b), and nine (2600 ng/μL Kdm4b). Error bars indicate standard error (SE). (***) P<0.001: (*) P<0.05, two-tailed Student's/-test. FIG. 1B depicts representative images of Xist RNA FISH (magenta) in Kdm4b-injected four-cell embryos. The gender of each embryo was assessed by simultaneous DNA FISH against the Rnf12 locus (gray). Arrows indicate the blastomeres, which are shown enlarged in the bottom panels. FIG. 1C depicts graphs showing the ratio of blastomeres with the indicated number of Xist RNA clouds and spots in male embryos. Each bar represents an individual embryo. The numbers of male embryos examined were six (no injection), five (1000 ng/μL Kdm4b), and 12 (2600 ng/μL Kdm4b). FIG. 1D depicts graphs showing the ratio of blastomeres with the indicated number of Xist RNA clouds and spots in female embryos. Each bar represents an individual embryo. The numbers of female embryos examined were six (no injection), six (1000 ng/μL Kdm4b), and eight (2600 ng/μL Kdm4b).

FIG. 2A depicts a genome browser view of H3K27me3 ChIP-seq (Zheng et al. 2016. Mol Cell 63:1066-1079), DNase I-seq (Inoue et al. 2017. Nature 547:419-424), and DNA methylation levels (Kobayashi et al. 2012. PLOS Genet 8: e1002440) at the Xist locus. (Oo) MII oocyte: (Sp) sperm: (7d) growing oocytes collected from 7-day-old females: (14d) growing oocytes collected from 14-day-old females: (GV) fully grown GV stage oocytes. FIG. 2B depicts a genome browser view of allelic H3K27me3 in one-cell, two-cell, and blastocyst embryos and E6.5 epiblast at the Xist locus. The highlighted square indicates a computationally determined region where the maternal allele bias of H3K27me3 enrichment is retained in blastocyst embryos. (Mat) Maternal allele: (Pat) paternal allele. The H3K27me3 ChIP-seq data sets were described in Zheng et al. (2016; Mol Cell 63: 1066-1079). FIG. 2C depicts a higher-resolution view of the Xist locus in blastocyst embryos. The maternal allele-biased H3K27me3 domain is shaded.

FIG. 3A depicts representative images of zygotes stained with anti-H3K27me3 antibody. (M) Maternal pronucleus, (P) paternal pronucleus. The bar graph indicates the relative H3K27me3 signal intensity of maternal pronuclei. The average signal of $Kdm6b^{MUT}$-injected zygotes was set as 1.0. The total numbers of embryos examined were 15 ($Kdm6b^{MUT}$) and 13 ($Kdm6b^{WT}$). Error bars indicate standard error (SE). (***) P<0.001, two-tailed Student's t-test. FIG. 3B is a genome browser view of the Xist locus showing loss of maternal H3K27me3 ChIP-seq signal in $Kdm6b^{WT}$-injected morula embryos. (Mat) Maternal allele; (Pat) paternal allele. FIG. 3C depicts representative images of Xist RNA FISH (light gray) in Kdm6b-injected four-cell embryos. The gender of each embryo was assessed by simultaneous DNA FISH against the Rnf12 locus (gray). FIG. 3D depicts graphs showing the ratio of blastomeres with the indicated number of Xist RNA clouds and spots in male four-cell embryos. Each bar represents an individual embryo. The numbers of male embryos examined were eight (Kdm6bMUT) and 15 (Kdm6bWT). FIG. 3E depicts graphs showing the ratio of blastomeres with the indicated number of Xist RNA clouds and spots in female four-cell embryos. Each bar represents an individual embryo. The numbers of female embryos examined were eight ($Kdm6b^{MUT}$) and 12 ($Kdm6^{WT}$).

FIG. 4A is an illustration depicting maternal XCI caused by $Kdm6^{WT}$-mediated maternal Xist expression. FIG. 4B depicts representative images of Xist RNA FISH (light gray) in Kdm6b-injected morula embryos. The gender of each embryo was assessed by simultaneous DNA FISH against the Rnf12 locus (gray). FIG. 4C depicts graphs showing the ratio of blastomeres with the indicated number of Xist RNA clouds in male morula embryos. Each bar represents an individual embryo. The numbers of male embryos examined were 19 (Kdm6bMUT) and 35 (Kdm6bWT). FIG. 4D depicts graphs showing the ratio of blastomeres with the indicated number of Xist RNA clouds in female morula embryos. Each bar represents an individual embryo. The numbers of female embryos examined were 34 (Kdm6bMUT) and 35 (Kdm6bWT). FIG. 4E depicts a box plot showing the relative expression of genes on individual maternal chromosomes between Kdm6b$^{MUT}$- and Kdm6b$^{WT}$-injected blastocysts. Genes with enough SNP reads (SNP reads >10, RPM [reads per million]>0.5) were analyzed. The middle lines in the boxes represent the medians. Box edges and whiskers indicate the 25th/75th and 2.5th/97.5th percentiles, respectively. (***) P<0.001, Mann-Whitney-Wilcoxon test.

FIG. 5A depicts representative images of Kdm6b-injected 4-cell and morula embryos immunostained with H3K27me3 antibody. Kdm6b mRNA was injected into zygotes. The embryos were fixed at 46 (4-cell) and 78 (morula) hrs after fertilization. FIG. 5B is a graph depicting relative H3K27me3 signal intensity. The signal intensities of multiple blastomeres were measured and averaged to obtain the value of a single embryo. The average signals of Kdm6b$^{MUT}$ embryos were set as 1.0. The total numbers of embryos examined were 9 (Kdm6b$^{MUT}$) and 9) (Kdm6b$^{WT}$) for 4-cell and 19 (Kdm6b$^{MUT}$) and 22 (Kdm6b$^{WT}$) for morulae. Error bars indicate standard error (SE). ***, p<0.001, * p<0.05 (two-tailed Student t-test).

FIG. 6A is a scatterplot showing a correlation between H3K27me3 peaks detected in mouse ESCs in the ENCODE project and in our hands using 500 or 2,000 ESCs. FIG. 6B depicts a scatterplot showing a correlation between H3K27me3 peaks of a published dataset (Liu et al. 2016. Nature 537:558-562) and Kdm6b$^{MUT}$-injected morula embryos. FIG. 6C depicts a Venn diagram showing a correlation between H3K27me3 peaks of a published dataset (Liu et al. 2016. Nature 537:558-562) and Kdm6b$^{MUT}$-injected morula embryos. FIG. 6D depicts genome browser views of representative loci showing almost identical H3K27me3 enrichment in the public dataset and Kdm6b$^{MUT}$-injected morula embryos. FIG. 6E is a graph depicting the number of H3K27me3 peaks detected in Kdm6b$^{MUT}$- and Kdm6b$^{WT}$-injected morula embryos. FIG. 6F depicts a genome browser view of the Xist locus showing loss of H3K27me3 domain in Kdm6b$^{WT}$-injected embryos. The parental alleles were not distinguished in these tracks.

FIG. 8A is a scatter plot showing the correlation between biological duplicate of RNA-seq samples. FIG. 8B is a box plot showing the maternal allelic expression ratios [Mat/(Mat+Pat)] of individual chromosomes in Kdm6b-injected blastocysts. Middle lines in the boxes represent the medians. Box edges and whiskers indicate the 25th/75th and 2.5th/97.5th percentiles, respectively. Kdm6bMUT: light gray, left bar; Kdm6b$^{WT}$: dark gray, right bar; p-value<2.2e-16. FIG. 8C is a graph showing the relative expression levels of X-linked genes between Kdm6bWT- and Kdm6bMUT-injected blastocyst embryos. The expression levels of the maternal allele were analyzed. Each dot represents an individual gene showing enough SNP reads (RPM>0.5). FIG. 8C shows genes excluding known escapees, depicted in FIG. 8D. FIG. 8D is a graph showing the relative expression levels of X-linked genes between Kdm6bWT- and Kdm6bMUT-injected blastocyst embryos. The expression levels of the maternal allele were analyzed. Each dot represents an individual gene showing enough SNP reads (RPM>0.5). FIG. 8D shows genes that are known escapees. From left to right: Rbm3, Suv39h1, Tbcld25, Atp6ap2, Araf, Ndufb11, Nkap, Lamp2, Utp14a, Idh3g, Eif2s3x, Xist, Kdm5c, Sms, Pdha1, Syap1, and Msl3.

DETAILED DESCRIPTION OF THE INVENTION

Figure 1A:
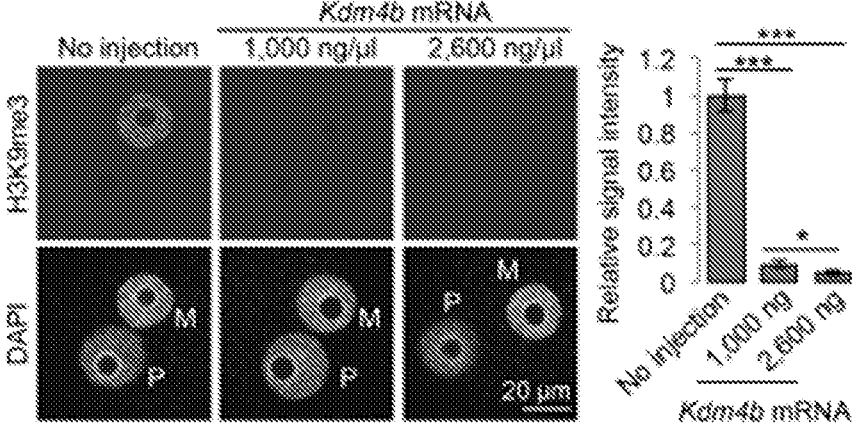
FIGS. 1A-1D show that ectopic removal of H3K9me3 did not induce maternal Xist expression.

The present invention features compositions and methods for recapitulating physiological X chromosome inactivation in a cell, including a cell of any embryo generated by Somatic Cell Nuclear Transfer (SCNT).

Kdm6b is an H3K27me3-specific demethylase. The present invention is based at least in part on the discovery that Kdm6b-mediated maternal X-chromosome inactivation recapitulates physiological-chromosome inactivation.
X-Chromosome Inactivation During development, X-chromosome inactivation (XCI) occurs in an imprinted or a random manner. For imprinted XCI, the paternal X chromosome (Xp) is selectively inactivated during preimplantation development. Random XCI occurs in epiblasts where it results in the silencing of either the Xp or maternal X chromosome (Xm). Xist is an X-linked long noncoding RNA that functions in both imprinted and random XCI. Xist is imprinted in the Xm during oogenesis. Xist RNA participates in XCI by coating and inactivating the X chromosome in cis.
H3K27Me3-Specific Demethylase In one aspect, the invention provides a method of increasing the efficiency of human SCNT comprising: contacting the nuclei or cytoplasm of a donor human somatic cell, a recipient human oocyte, a hybrid oocyte (e.g., human enucleated oocyte comprising donor genetic material prior to fusion or activation) or a human SCNT embryo (i.e., after fusion of the donor nuclei with the enucleated oocyte) with an H3K27me3-specific demethylase (Kdm6a, Kdm6b, Kdm6c, etc.) capable of recapitulating physiological X-chromosome inactivation. As discussed herein, the inventors have discovered that H3K27me3-specific demethylase can be used to normalize maternal X chromosome inactivation relative to paternal X chromosome inactivation thereby increasing the efficiency of human SCNT.
H3K27Me3-Specific Demethylase Activators In one aspect, the invention provides a method of increasing the efficiency of human SCNT comprising: contacting the nuclei or cytoplasm of donor human somatic cell, a recipient human oocyte, a hybrid oocyte (e.g., human enucleated oocyte comprising donor genetic material prior to fusion or activation) or a human SCNT embryo (i.e., after fusion of the donor nuclei with the enucleated oocyte) with an agent that activates an H3K27me3-specific demethylase (Kdm6a, Kdm6b, Kdm6c, etc.).

In some embodiments, a H3K27me3-specific demethylase activator useful in the methods, compositions and kits as disclosed herein is an agent which increases the expression of genes encoding an H3K27me3-specific demethylase, or increases the activity of human H3K27me3-specific demethylase, for example, human Kdm6a, Kdm6b, Kdm6c, etc.

In some embodiments, a H3K27me3-specific demethylase activator useful in the methods, compositions and kits as disclosed herein is a nucleic acid agent which encodes a Kdm6a. Kdm6b, or Kdm6c polypeptide.

In some embodiment, the agent comprises a nucleic acid sequence encoding a human H3K27me3-specific demethylase activator, including but not limited to Kdm6a. Kdm6b, or Kdm6c, or a biologically active fragment or homologue or variant thereof having at least 80% sequence identity (or at least about 85%, or at least about 90%, or at least about 95%, or at least about 98%, or at least about 99% sequence identity) thereto which increases the efficiency of human SCNT to a similar or greater extent as compared to the corresponding wild-type sequence encoding human Kdm6a, Kdm6b, or Kdm6c.

In some embodiments, a H3K27me3-specific demethylase activator activator for use in the methods as disclosed herein is selected from any human Kdm6a, Kdm6b, or Kdm6c polypeptide, or a variant or biological active fragment of such a human human Kdm6a. Kdm6b, or Kdm6c polypeptide. It is encompassed in the present invention that one of ordinary skill in the art can identify an appropriate human homologue of human Kdm6a, Kdm6b, or Kdm6c polypeptides, and the nucleic acid encoding such a human homologue for use in the methods and composition as disclosed herein. In some embodiments, a H3K27me3-specific demethylase activator is a nucleic acid agent encoding a H3K27me3-specific demethylase polypeptide, which is expressed from a vector, e.g., a viral vector.

In alternative embodiments, a H3K27me3-specific demethylase activator encompassed for use herein is a synthetic modified RNA (modRNA) encoding Kdm6a. Kdm6b, or Kdm6c, or functional fragments thereof. Synthetic modified RNA (modRNA) are described in U.S. applications US2012/03228640; US2009/0286852 and US2013/0111615 and U.S. Pat. Nos. 8,278,036; 8,691,966; 8,748,089; 8,835,108, which are incorporated herein in their entirety by reference. In some embodiments, the synthetic, modified RNA molecule is not expressed in a vector, and the synthetic, modified RNA molecule can be a naked synthetic, modified RNA molecule. In some embodiments, a composition can comprises at least one synthetic, modified RNA molecule present in a lipid complex.

In some embodiments, the synthetic, modified RNA molecule comprises at least two modified nucleosides, for example, at least two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2'deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm) N2,7-dimethylguanosine (m2.7G), N2, N2, 7-trimethylguanosine (m2,2,7G), and inosine (I). In some embodiments, the synthetic, modified RNA molecule further comprises a 5' cap, such as a 5' cap analog, e.g., a 5' diguanosine cap. In some embodiments, a synthetic, modified RNA molecule for use in the methods and compositions as disclosed herein does not comprise a 5' triphosphate. In some embodiments, a synthetic, modified RNA molecule for use in the methods and compositions as disclosed herein further comprises a poly(A) tail, a Kozak sequence, a 3' untranslated region, a 5' untranslated region, or any combination thereof, and in some embodiments, a synthetic, modified RNA molecule can optionally treated with an alkaline phosphatase.

In introducing polynucleotides described herein, essentially any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and translation of the encoded protein. Other methods known in the art for introducing nucleic acids to cells can be used, such as lipid-mediated carrier transport, chemical mediated transport, such as calcium phosphate, and the like.

For expression within cells, DNA vectors, for example plasmid vectors comprising a promoter directing expression of a polynucleotide encoding the H3K27me3-specific demethylase polypeptide can be employed. In some embodiments, expression of the encoded protein is controlled by an inducible promoter or a conditional expression system. Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies.

Somatic Cell Nuclear Transfer

Somatic cell nuclear transfer (SCNT) is a technique that may be used, for example, for the reproductive cloning of livestock (e.g., cows, horses, sheep, goats, pigs) or for therapeutic cloning, in which desired tissues are produced for cell replacement therapy. Unfortunately, cloned animals suffer from certain defects arising from improper X-chromosome inactivation. The present invention addresses these defects by restoring physiologic X chromosome inactivation to embryos generated from in vitro fertilization, i.e., generating using SCNT.

Somatic cell nuclear transfer involves obtaining a nuclear donor cell, then fusing this nuclear donor cell into an enucleated recipient cell, most preferably an enucleated oocyte, to form a nuclear transfer embryo, activating this embryo, and finally culturing the embryo or transferring this embryo into a maternal host. During nuclear transfer a full complement of nuclear DNA from one cell is introduced to an enucleated cell. Nuclear transfer methods are well known to a person of ordinary skill in the art. See, U.S. Pat. No. 4,994,384 to Prather et al., entitled "Multiplying Bovine Embryos," issued on Feb. 19, 1991: U.S. Pat. No. 5,057,420 to Massey, entitled "Bovine Nuclear Transplantation," issued on Oct. 15, 1991: U.S. Pat. No. 5,994,619, issued on Nov. 30, 1999 to Stice et al., entitled "Production of Chimeric Bovine or Porcine Animals Using Cultured Inner Cell Mass Cells: U.K. Patents Nos. GB 2,318,578 GB 2,331,751, issued on Jan. 19, 2000 to Campbell et al. and Wilmut et al., respectively, entitled "Quiescent Cell Populations For Nuclear Transfer": U.S. Pat. No. 6,011,197 to Strelchenko et al., entitled "Method of Cloning Bovines Using Reprogrammed Non-Embryonic Bovine Cells." issued on Jan. 4, 2000; and in U.S. patent application Ser. No. 09/753,323 entitled "Method of Cloning Porcine Animals, filed Dec. 28, 2000), each of which are hereby incorporated by reference in its entirety including all figures, tables and drawings. Nuclear transfer may be accomplished by using oocytes that are not surrounded by a zona pellucida.

In a nuclear transfer procedure, a nuclear donor cell, or the nucleus thereof, is introduced into a recipient cell. A recipient cell is preferably an oocyte and is preferably enucleated. However, the invention relates in part to nuclear transfer, where a nucleus of an oocyte is not physically extracted from the oocyte. It is possible to establish a nuclear transfer embryo where nuclear DNA from the donor cell is replicated during cellular divisions. See, e.g., Wagoner et al., 1996, "Functional enucleation of bovine oocytes: effects of centrifugation and ultraviolet light." Theriogenology 46:279-284. In addition, nuclear transfer may be accomplished by combining one nuclear donor and more than one enucleated oocyte. Also, nuclear transfer may be accomplished by combining one nuclear donor, one or more enucleated oocytes, and the cytoplasm of one or more enucleated oocytes. The resulting combination of a nuclear donor cell and a recipient cell can be referred to as a "hybrid cell."

The term "nuclear donor" as used herein refers to any cell, or nucleus thereof, having nuclear DNA that can be translocated into an oocyte. A nuclear donor may be a nucleus that has been isolated from a cell. Multiple techniques are available to a person of ordinary skill in the art for isolating a nucleus from a cell and then utilizing the nucleus as a nuclear donor. See, e.g., U.S. Pat. Nos. 4,664,097, 6,011,197, and 6,107,543, each of which is hereby incorporated by reference in its entirety including all figures, tables and drawings. Any type of cell can serve as a nuclear donor. Examples of nuclear donor cells include, but are not limited to, cultured and non-cultured cells isolated from an embryo arising from the union of two gametes in vitro or in vivo: embryonic stem cells (ES cells) arising from cultured embryonic cells (e.g., pre-blastocyst cells and inner cell mass cells); cultured and non-cultured cells arising from inner cell mass cells isolated from embryos: cultured and non-cultured pre-blastocyst cells: cultured and non-cultured fetal cells: cultured and non-cultured adult cells: cultured and non-cultured primordial germ cells: cultured and non-cultured germ cells (e.g., embryonic germ cells); cultured and non-cultured somatic cells isolated from an animal: cultured and non-cultured cumulus cells: cultured and non-cultured amniotic cells; cultured and non-cultured fetal fibroblast cells: cultured and non-cultured genital ridge cells; cultured and non-cultured differentiated cells: cultured and non-cultured cells in a synchronous population: cultured and non-cultured cells in an asynchronous population; cultured and non-cultured serum-starved cells: cultured and non-cultured permanent cells; and cultured and non-cultured totipotent cells. See, e.g., Piedrahita et al., 1998, Biol. Reprod. 58:1321-1329; Shim et al., 1997, Biol. Reprod. 57:1089-1095: Tsung et al., 1995, Shih Yen Sheng Wu Hsueh Pao 28:173-189; and Wheeler, 1994, Reprod. Fertil. Dev. 6:563-568, each of which is incorporated herein by reference in its entirety including all figures, drawings, and tables. In addition, a nuclear donor may be a cell that was previously frozen or cryopreserved.

Hybrid cells made by the process of nuclear transfer may be used, for example, in reproductive cloning or in regenerative cloning.

SCNT experiments showed that nuclei from adult differentiated somatic cells can be reprogrammed to a totipotent state. Accordingly, a SCNT embryo generated using the methods as disclosed herein can be cultured in a suitable in vitro culture medium for the generation of totipotent or embryonic stem cell or stem-like cells and cell colonies. Culture media suitable for culturing and maturation of embryos are well known in the art. Examples of known media, which may be used for bovine embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, new born serum, estrual cow serum, lamb serum or steer serum. A preferred maintenance medium includes TCM-199 with Earl salts, 10% fetal calf serum, 0.2 Ma pyruvate and 50 µg/ml gentamicin sulphate. Any of the above may also involve co-culture with a variety of cell types such as granulosa cells, oviduct cells, BRL cells and uterine cells and STO cells.

In particular, epithelial cells of the endometrium secrete leukemia inhibitory factor (LIF) during the preimplantation and implantation period. Therefore, in some embodiments, the addition of LIF to the culture medium is encompassed to enhancing the in vitro development of the SCNT-derived embryos. The use of LIF for embryonic or stem-like cell cultures has been described in U.S. Pat. No. 5,712,156, which is herein incorporated by reference.

Another maintenance medium is described in U.S. Pat. No. 5,096,822 to Rosenkrans, Jr. et al., which is incorporated herein by reference. This embryo medium, named CRI, contains the nutritional substances necessary to support an embryo. CRI contains hemicalcium L-lactate in amounts ranging from 1.0 mM to 10 mM, preferably 1.0 mM to 5.0 mM. Hemicalcium L-lactate is L-lactate with a hemicalcium salt incorporated thereon. Also, suitable culture medium for maintaining human embryonic stem cells in culture as discussed in Thomson et al., Science, 282:1145-1147 (1998) and Proc. Natl. Acad. Sci., USA, 92:7844-7848 (1995).

In some embodiments, the feeder cells will comprise mouse embryonic fibroblasts. Means for preparation of a suitable fibroblast feeder layer are described in the example which follows and is well within the skill of the ordinary artisan.

Methods of deriving ES cells (e.g., NT-ESCs or hNT-ESCs) from blastocyst-stage SCNT embryos (or the equivalent thereof) are well known in the art. Such techniques can be used to derive ES cells (e.g., hNT-ESCs) from SCNT embryos, where the SCNT embryos used to generate hNT-ESCs have a reduced level of H3K9me3 in the nuclear genetic material donated from the somatic donor cell, as compared to SCNTs which were not treated with a member of the KDM4 demethylase family and/or an inhibitor of the histone methyltransferase SUV39h1/SUV39h2. hNT-ESCs can be derived from cloned SCNT embryos during earlier stages of development.

In certain embodiments, blastomeres generated from SCNT embryos generated using the methods, compositions and kits as disclosed herein can be dissociated using a glass pipette to obtain totipotent cells. In some embodiments, dissociation may occur in the presence of 0.25% trypsin (Collas and Robl, 43 BIOL. REPROD. 877-84, 1992; Stice and Robl, 39 BIOL. REPROD. 657-664, 1988; Kanka et al., 43 MOL. REPROD. DEV. 135-44, 1996).

In certain embodiments, the resultant blastocysts, or blastocyst-like clusters from the SCNT embryos can be used to obtain embryonic stem cell lines, eg., nuclear transfer ESC (ntESC) cell lines. Such lines can be obtained, for example, according to the culturing methods reported by Thomson et al., Science, 282:1145-1147 (1998) and Thomson et al., Proc. Natl. Acad. Sci., USA, 92:7544-7848 (1995), incorporated by reference in their entirety herein.

Pluripotent embryonic stem cells can also be generated from a single blastomere removed from a SCNT embryo without interfering with the embryo's normal development to birth. See U.S. application Nos. 60/624,827, filed Nov. 4, 2004; 60/662,489, filed Mar. 14, 2005; 60/687,158, filed Jun. 3, 2005; 60/723,066, filed Oct. 3, 2005; 60/726,775, filed Oct. 14, 2005; 11/267,555 filed Nov. 4, 2005; PCT application no. PCT/US05/39776, filed Nov. 4, 2005, the disclosures of which are incorporated by reference in their entirety; see also Chung et al., Nature, Oct. 16, 2005 (electronically published ahead of print) and Chung et al., Nature V. 439, pp. 216-219 (2006), the entire disclosure of each of which is incorporated by reference in its entirety). In such a case, an SCNT embryo is not destroyed for the generation of pluripotent stem cells.

In one aspect of the invention, the method comprises the utilization of cells derived from the SCNT embryo in research and in therapy. Such pluripotent stem cells (PSCs) or totipotent stem cells (TSC) can be differentiated into any of the cells in the body including, without limitation, skin, cartilage, bone, skeletal muscle, cardiac muscle, renal, hepatic, blood and blood forming, vascular precursor and vascular endothelial, pancreatic beta, neurons, glia, retinal, inner ear follicle, intestinal, lung, cells.

In another embodiment of the invention, the SCNT embryo, or blastocyst, or pluripotent or totipotent cells obtained from a SCNT embryo (e.g., NT-ESCs), can be exposed to one or more inducers of differentiation to yield other therapeutically-useful cells such as retinal pigment epithelium, hematopoietic precursors and hemangioblastic progenitors as well as many other useful cell types include ectoderm, mesoderm, and endoderm. Such inducers include but are not limited to: cytokines such as interleukin-alpha A, interferon-alpha A/D, interferon-beta, interferon-gamma, interferon-gamma-inducible protein-10, interleukin-1-17, keratinocyte growth factor, leptin, leukemia inhibitory factor, macrophage colony-stimulating factor, and macrophage inflammatory protein-1 alpha, 1-beta, 2, 3 alpha, 3 beta, and monocyte chemotactic protein 1-3, 6kine, activin A, amphiregulin, angiogenin, B-endothelial cell growth factor, beta cellulin, brain-derived neurotrophic factor, C10, cardiotrophin-1, ciliary neurotrophic factor, cytokine-induced neutrophil chemoattractant-1, eotaxin, epidermal growth factor, epithelial neutrophil activating peptide-78, erythropoietin, estrogen receptor-alpha, estrogen receptor-beta, fibroblast growth factor (acidic and basic), heparin, FLT-3/FLK-2 ligand, glial cell line-derived neurotrophic factor. Gly-His-Lys, granulocyte colony stimulating factor, granulocytemacrophage colony stimulating factor. GRO-alpha/MGSA, GRO-beta, GRO-gamma, HCC-1, heparin-binding epidermal growth factor, hepatocyte growth factor, heregulin-alpha, insulin, insulin growth factor binding protein-1, insulin-like growth factor binding protein-1, insulin-like growth factor, insulin-like growth factor II, nerve growth factor, neurotophin-3,4, oncostatin M, placenta growth factor, pleiotrophin, rantes, stem cell factor, stromal cell-derived factor 1B, thromopoietin, transforming growth factor—(alpha, beta 1,2,3,4,5), tumor necrosis factor (alpha and beta), vascular endothelial growth factors, and bone morphogenic proteins, enzymes that alter the expression of hormones and hormone antagonists such as 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagons, gonadotropin, L-3,3',5'-triiodothyronine, leutinizing hormone, L-thyroxine, melatonin. MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxin-binding globulin, and vasopressin, extracellular matrix components such as fibronectin, proteolytic fragments of fibronectin, laminin, tenascin, thrombospondin, and proteoglycans such as aggrecan, heparan sulphate proteoglycan, chontroitin sulphate proteoglycan, and syndecan. Other inducers include cells or components derived from cells from defined tissues used to provide inductive signals to the differentiating cells derived from the reprogrammed cells of the present invention. Such inducer cells may derive from human, non-human mammal, or avian, such as specific pathogen-free (SPF) embryonic or adult cells.

Blastomere Culturing. In one embodiment, the SCNT embryos can be used to generate blastomeres and utilize in vitro techniques related to those currently used in preimplantation genetic diagnosis (PGD) to isolate single blastomeres from a SCNT embryo, generated by the methods as disclosed herein, without destroying the SCNT embryos or otherwise significantly altering their viability. As demonstrated herein, pluripotent embryonic stem (hES) cells and cell lines can be generated from a single blastomere removed from a SCNT embryo as disclosed herein without interfering with the embryo's normal development to birth.

The discoveries of Wilmut et al. (Wilmut, et al. Nature 385, 810 (1997) in sheep cloning of "Dolly", together with those of Thomson et al. (Thomson et al., Science 282, 1145 (1998)) in deriving hESCs, have generated considerable enthusiasm for regenerative cell transplantation based on the establishment of patient-specific hESCs derived from SCNT-embryos or SCNT-engineered cell masses generated from a patient's own nuclei. This strategy, aimed at avoiding immune rejection through autologous transplantation, is perhaps the strongest clinical rationale for SCNT. By the same token, derivations of complex disease-specific SCNT-hESCs may accelerate discoveries of disease mechanisms. For cell transplantations, innovative treatments of murine SCID and PD models with the individual mouse's own SCNT-derived mESCs are encouraging (Rideout et al, Cell 109, 17 (2002); Barberi, Nat. Biotechnol. 21, 1200 (2003)). Ultimately, the ability to create banks of SCNT-derived stem cells with broad tissue compatibility would reduce the need for an ongoing supply of new oocytes.

In certain embodiments of the invention, pluripotent or totipotent cells obtained from a SCNT embryo (e.g., hNT-ESCs) can be optionally differentiated, and introduced into the tissues in which they normally reside in order to exhibit therapeutic utility. For example, pluripotent or totipotent cells obtained from a SCNT embryo can be introduced into the tissues. In certain other embodiments, pluripotent or totipotent cells obtained from a SCNT embryo can be introduced systemically or at a distance from a cite at which therapeutic utility is desired. In such embodiments, the pluripotent or totipotent cells obtained from a SCNT embryo can act at a distance or may hone to the desired cite.

In certain embodiments of the invention, cloned cells, pluripotent or totipotent cells obtained from a SCNT embryo can be utilized in inducing the differentiation of other pluripotent stem cells. The generation of single cell-derived populations of cells capable of being propagated in vitro while maintaining an embryonic pattern of gene expression is useful in inducing the differentiation of other pluripotent stem cells. Cell-cell induction is a common means of directing differentiation in the early embryo. Many potentially medically-useful cell types are influenced by inductive signals during normal embryonic development including spinal cord neurons, cardiac cells, pancreatic beta cells, and definitive hematopoietic cells. Single cell-derived populations of cells capable of being propagated in vitro while maintaining an embryonic pattern of gene expression can be cultured in a variety of in vitro, in ovo, or in vivo culture conditions to induce the differentiation of other pluripotent stem cells to become desired cell or tissue types.

The pluripotent or totipotent cells obtained from a SCNT embryo (e.g., ntESCs) can be used to obtain any desired differentiated cell type. Therapeutic usages of such differentiated cells are unparalleled. As discussed herein, the donor cell, or the recipient oocyte, the hybrid oocyte or SCNT embryo can be treated with an H3K27me3-specific demethylase according to the methods as disclosed herein.

Alternatively, the donor cells can be adult somatic cells from a subject with a disorder, and the generated SCNT embryos can be used to produce animal models of disease or disease-specific pluripotent or totipotent cells which can be cultured under differentiation conditions to produce cell models of disease. The great advantage of the present invention is that by increasing the efficiency of SCNT, it provides an essentially limitless supply of isogenic or syngeneic ES cells, particularly pluripotent that are not induced pluripotent stem cells (e.g., not iPSCs). Such NT-ESCs have advantages over iPSCs and are suitable for transplantation, as they do not partially pluripotent, and do not have viral transgenes or forced expression of reprogramming factors to direct their reprogramming.

In some embodiments, the NT-ESCs generated from the SCNTs are patient-specific pluripotent obtained from SCNT embryos, where the donor cell was obtained from a subject to be treated with the pluripotent stem cells or differentiated progeny thereof. Therefore, it will obviate the significant problem associated with current transplantation methods, i.e., rejection of the transplanted tissue which may occur because of host-vs-graft or graft-vs-host rejection. Conventionally, rejection is prevented or reduced by the administration of anti-rejection drugs such as cyclosporin. However, such drugs have significant adverse side-effects, e.g., immunosuppression, carcinogenic properties, as well as being very expensive. The present invention should eliminate, or at least greatly reduce, the need for anti-rejection drugs, such as cyclosporine, imulan, FK-506, glucocorticoids, and rapamycin, and derivatives thereof.

Kits

The invention provides kits comprising an H3K27me3-specific demethylase activators (e.g., polynucleotides encoding Kdm6a, Kdm6b, or Kdm6c, a Kdm6a, Kdm6b, or Kdm6c polypeptide, or an enzymatically active fragment thereof).

In some embodiments, the kit comprises a sterile container which contains a therapeutic or prophylactic cellular composition: such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to enhance the efficiency of SCNT. The instructions will generally include information about the use of the composition enhance physiologic X chromosome inactivation. In other embodiments, the instructions include at least one of the following: description of the therapeutic agent; dosage schedule and administration for treatment or prevention of a neurological disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984): "Animal Cell Culture" (Freshney, 1987); "Methods in Enzymology" "Handbook of Experimental Immunology" (Weir, 1996): "Gene Transfer Vectors for Mammalian Cells" (Miller and Calos, 1987): "Current Protocols in Molecular Biology" (Ausubel, 1987): "PCR: The Polymerase Chain Reaction", (Mullis, 1994): "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: H3K9Me3 is Dispensable for Xist Silencing in Biparental Embryos

Figure 1B:
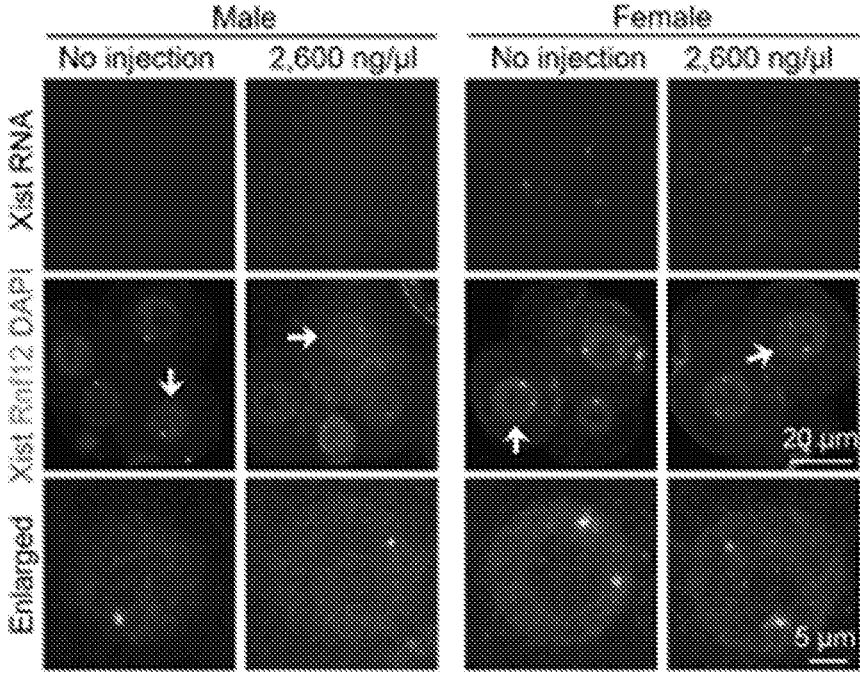
Figure 1C:
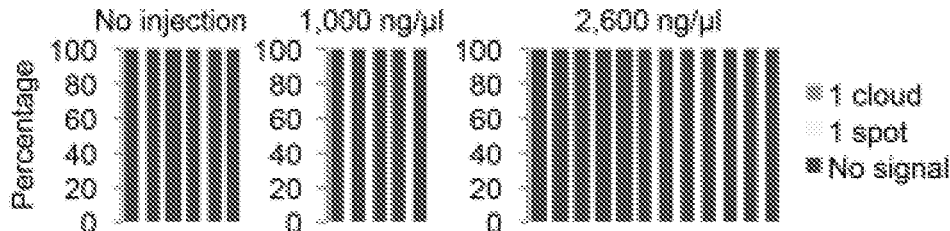
Figure 1D:
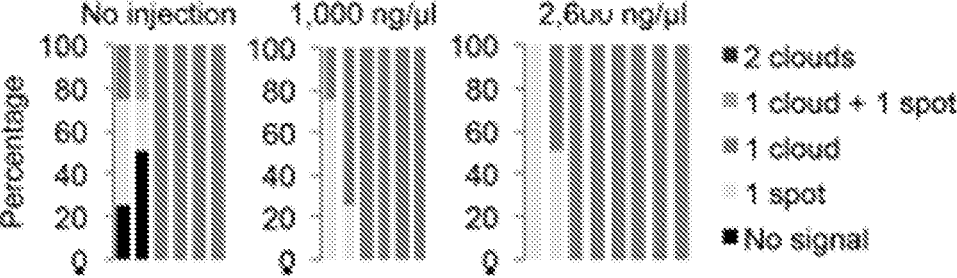

To determine whether Kdm4b-mediated loss of H3K9me3 can induce Xist derepression in biparental embryos, Kdm4b mRNA was injected into in vitro fertilization-derived embryos. Immunostaining analysis confirmed that Kdm4b mRNA injection effectively depleted H3K9me3 in zygotes in a concentration-dependent manner (FIG. 1A). To assess Xist RNA expression, RNA fluorescent in situ hybridization (FISH) analysis was performed in four-cell embryos. To distinguish between male and female embryos, X chromosomes were simultaneously labeled by DNA FISH using a probe specific for the Rnf12 locus. As such, each blastomere of the male or female embryos should have one or two DNA FISH signals, respectively. The "no injection" control male embryos showed no Xist RNA signal, and the majority of female embryos showed one RNA cloud or spot signal (FIGS. 1B-ID). Similarly, Kdm4b-injected embryos did not induce maternal Xist expression in either male or female embryos (FIGS. 1B-1D). Without being bound by theory, this indicates that H3K9me3 does not play a major role in maternal Xist silencing under physiological biparental conditions.

Figure 2A:
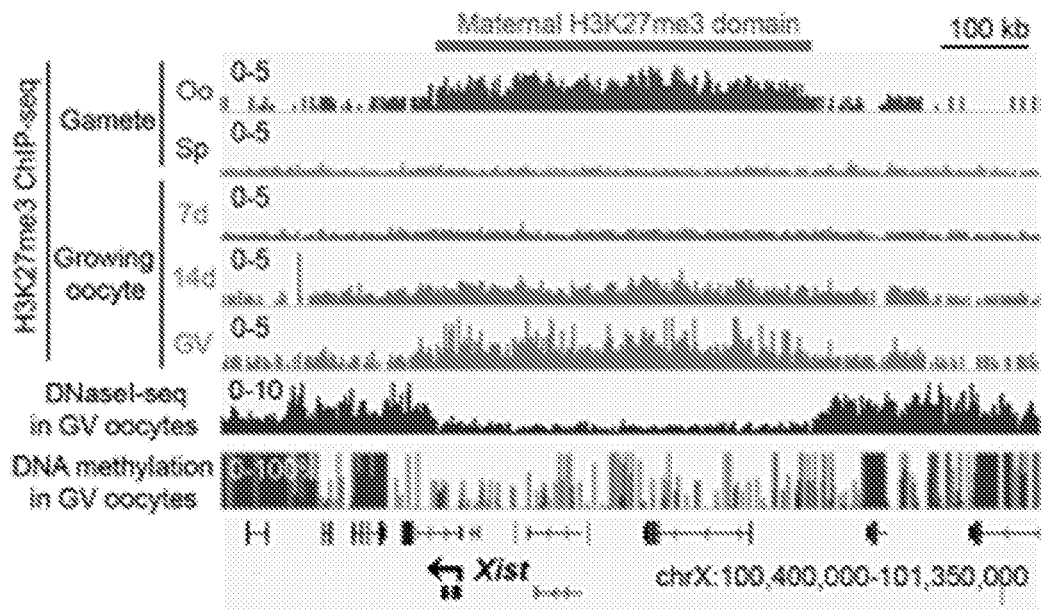
FIGS. 2A-2C show that maternal H3K27me3 coated Xist in oocytes and preimplantation embryos.
Figure 2B:
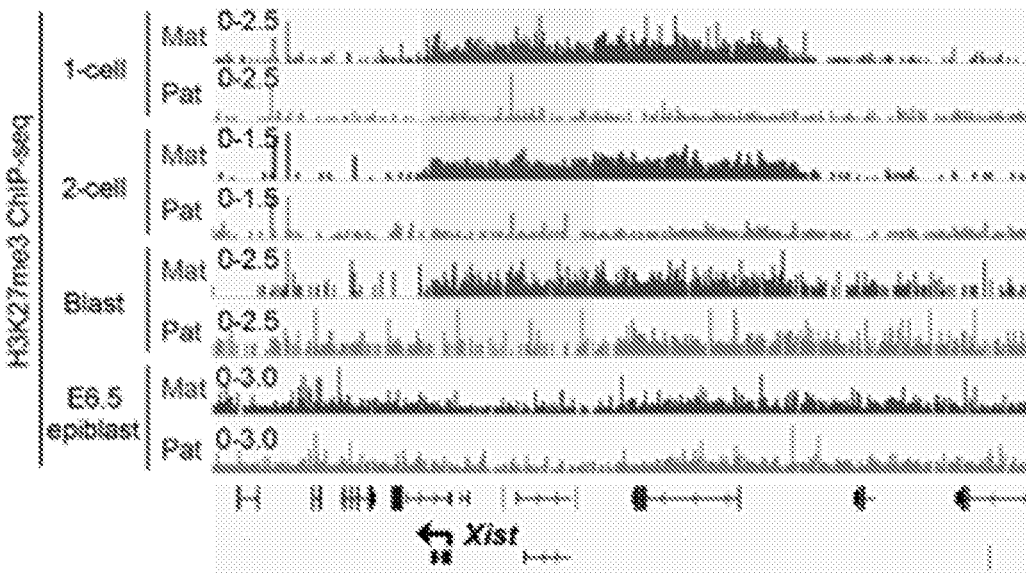
Figure 2C:
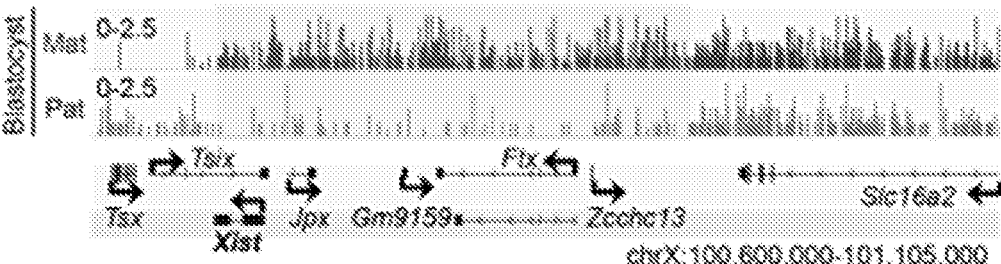

Example 2: Maternal H3K27Me3 Coats Xist in Oocytes and Preimplantation Embryos Since maternal H3K27me3 can function as an imprinting mark (Inoue et al. 2017. Nature 547:419-424), its potential involvement in Xist imprinting was examined. Analysis of H3K27me3 ChIP-seq (chromatin immunoprecipitation [ChIP] combined with high-throughput sequencing) data sets (Zheng et al. 2016. Mol Cell 63:1066-1079) revealed that Xist is coated with a broad H3K27me3 domain, which spans ~450 kb in mature oocytes and is established during oocyte growth (FIG. 2A). Analyses of the oocyte DNase I sequencing (DNase I seq) (Inoue et al. 2017. Nature 547: 419-424) and DNA methylome (Kobayashi et al. 2012. PLOS Genet 8: e1002440) data sets revealed that this entire H3K27me3 domain exhibits low chromatin accessibility and low DNA methylation (FIG. 2A). Without being bound by theory, this suggests formation of a heterochromatin domain independent of DNA methylation. Analyses of the ChIP-seq data sets of post-fertilization embryos (Zheng et al. 2016. Mol Cell 63:1066-1079) revealed that the maternal H3K27me3 domain is maintained throughout preimplantation development but is lost in the embryonic day 6.5 (E6.5) epiblast (FIG. 2B). Notably, the upstream ~200-kb region, which spans Xist to Zeche13, but does not include the T six promoter, maintains the maternal allele bias of H3K27me3 enrichment in blastocyst embryos (FIG. 2C). These data support a potential role for maternal H3K27me3 in maternal Xist silencing.

Example 3. Maternal H3K27Me3 is Responsible for Maternal Xist Silencing

Figure 3A:
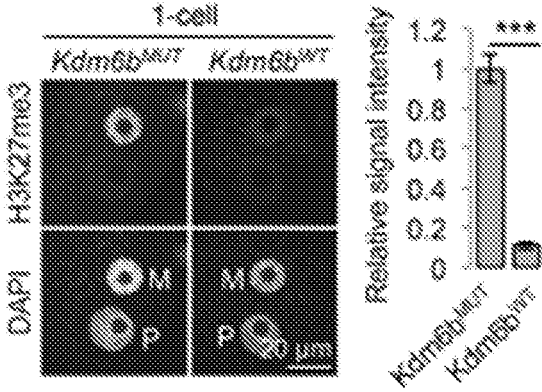
FIGS. 3A-3E show that loss of H3K27me3 induced maternal Xist expression.
Figure 5A:
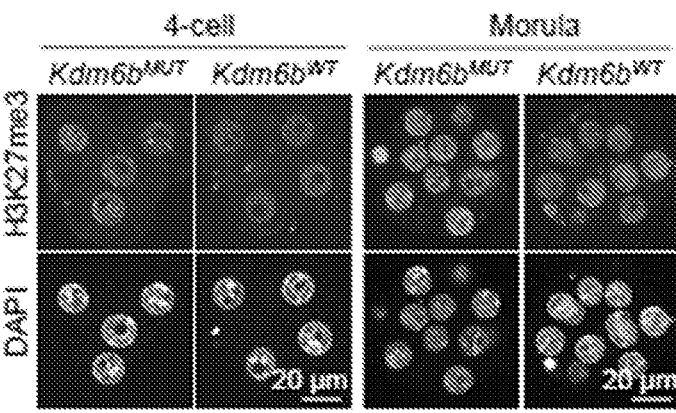
FIGS. 5A and 5B show that ectopic Kdm6b$^{WT}$ mRNA injection resulted in reduction of H3K27me3 in preimplantation embryos. These results are related to those shown in FIGS. 3A-3E.
Figure 5B:
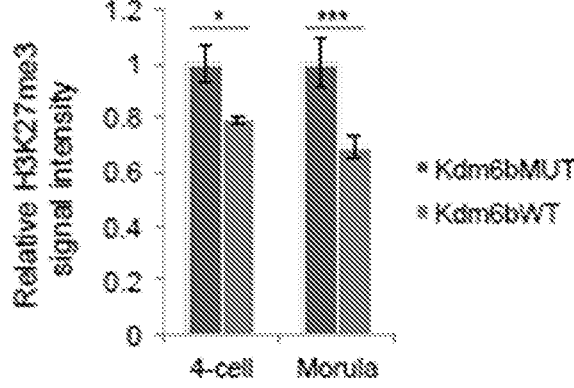

To examine whether H3K27me3 is responsible for maternal Xist silencing. H3K27me3 was depleted in zygotes by injecting mRNA coding an H3K27me3-specific demethylase. Kdm6b (FIG. 3A). As a negative control, zygotes were prepared by injection with the catalytic mutant. Kdm6bMUT, harboring a point mutation at the catalytic domain (FIG. 3A: Inoue et al. 2017. Nature 547:419-424). Despite the transient expression of the exogenous Kdm6b, the H3K27me3 level in Kdm6bWT embryos was significantly lower than that of Kdm6bMUT embryos at the four-cell and morula stages (FIGS. 5A-5B).

Figure 3B:
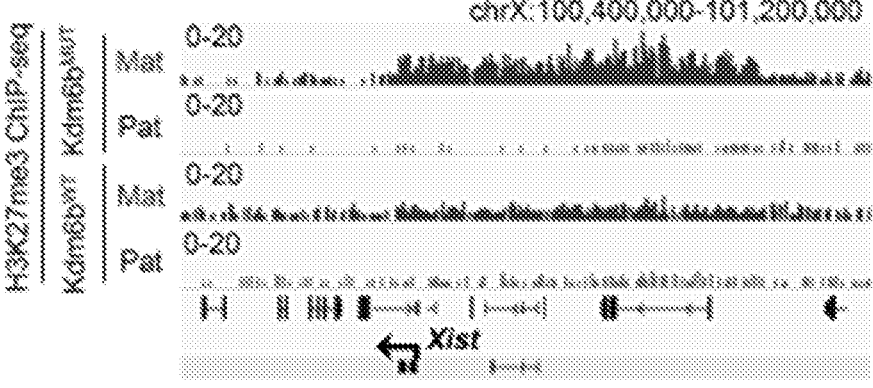
Figure 6A:
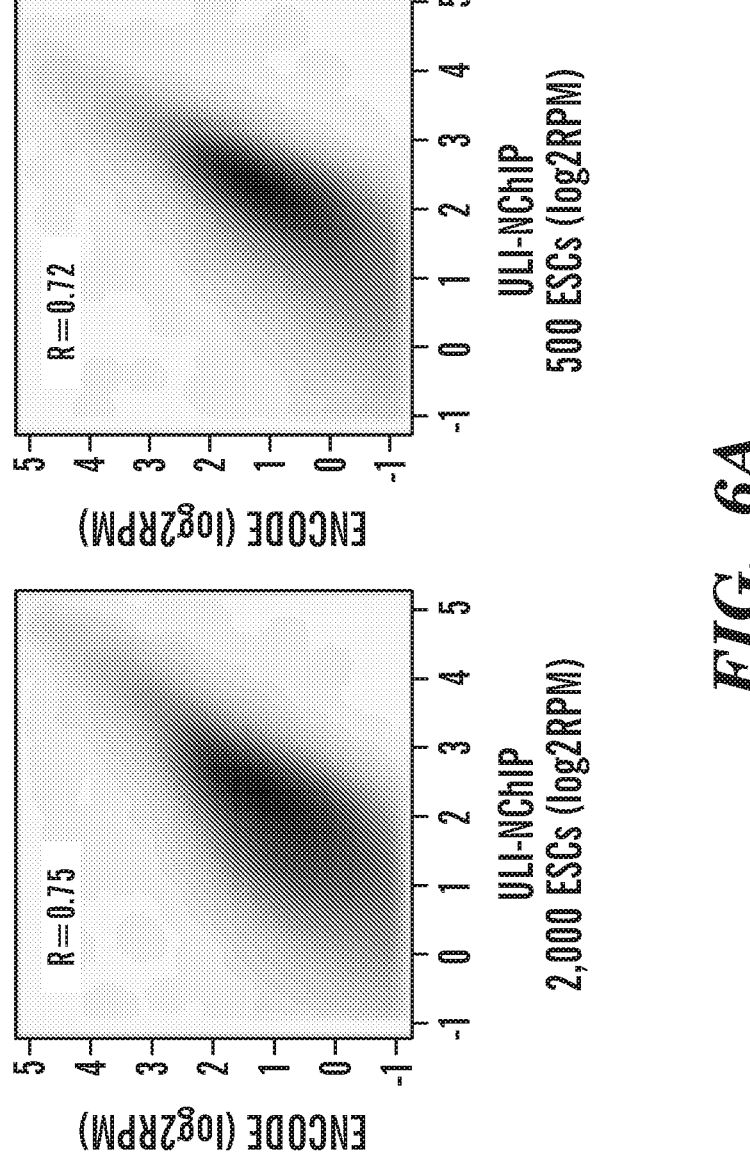
FIGS. 6A-6F show validation of H3K27me3 ULI-NChIP in embryonic stem cells (ESCs) and Kdm6b-injected morula embryos. These results are related to those shown in FIGS. 3A-3E.
Figure 6C:
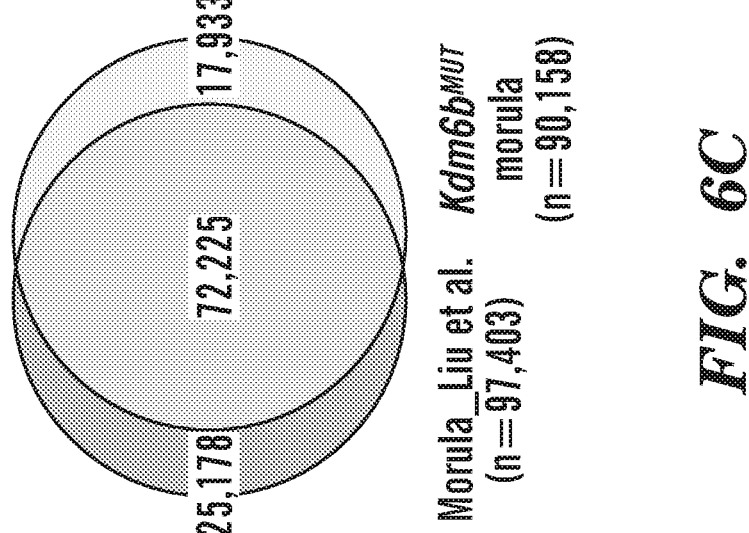
Figure 6B:
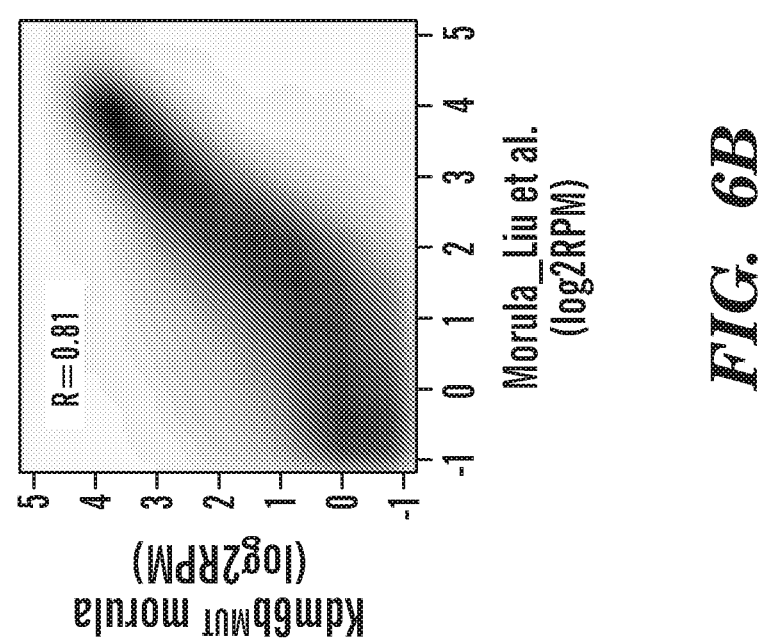
Figure 6D:
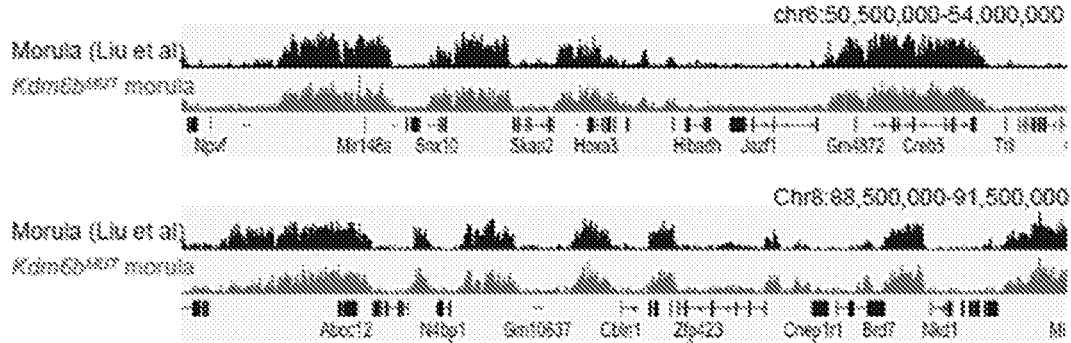
Figure 6E:
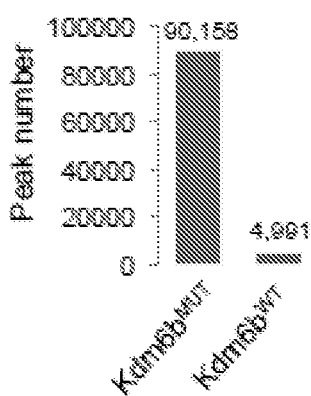
Figure 6F:
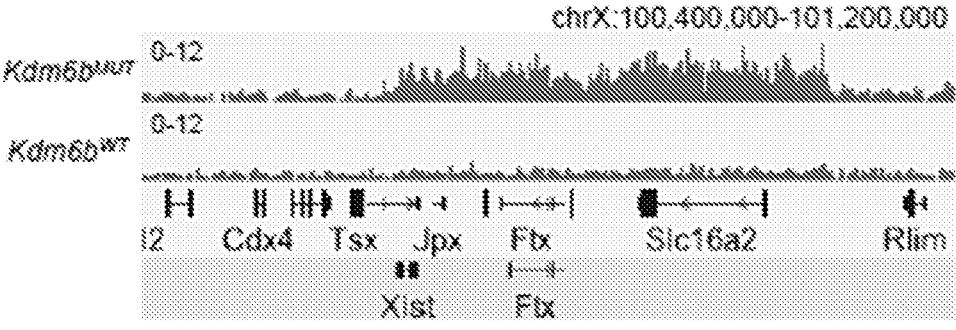

To confirm that H3K27me3 is lost at the Xist locus in Kdm6bWT-injected embryos, ultralow input native ChIP-seq (ULI-NChIP) analysis was performed (Brind'Amour et al. 2015. Nat Commun 6:6033), which worked efficiently using 500-2000 mouse embryonic stem cells (FIG. 6A). H3K27me3 ULI-NChIP was performed using ~2000 blastomeres from Kdm6bWT- or Kdm6bMUT-injected morula embryos. Data quality was validated by comparing Kdm6bMUT-injected embryos with a public morula embryo data set (FIG. 6B-6D; Liu et al. 2016. Nature 537:558-562). The number of H3K27me3 peaks in Kdm6bWT-injected embryos was much smaller than that of Kdm6bMUT-injected embryos (FIG. 6E). Importantly, the Xist locus exhibits a marked decrease of H3K27me3 enrichment throughout the entire domain in Kdm6bWT embryos (FIG. 6F). Furthermore, analysis of single-nucleotide polymorphism (SNP) information revealed that the maternal H3K27me3 domain was lost in Kdm6bWT embryos (FIG. 3B).

Figure 3C:
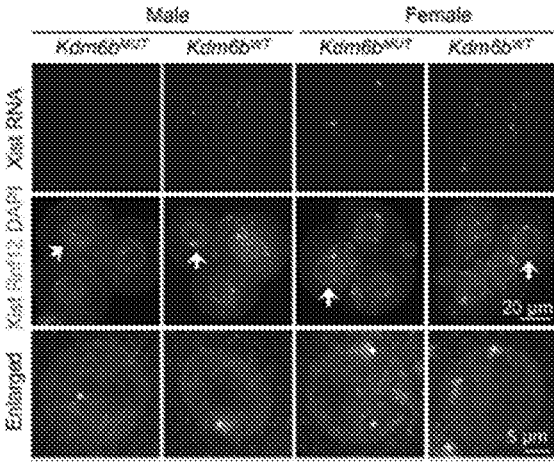
Figure 3D:
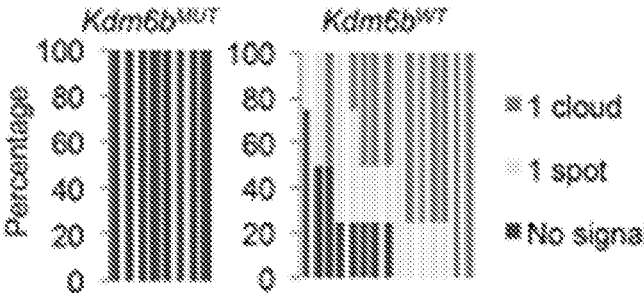
Figure 3E:
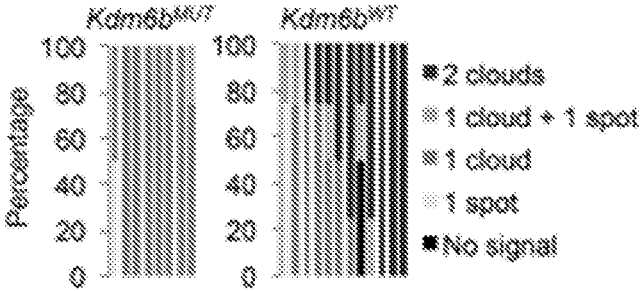

To examine whether maternal Xist is depressed in Kdm6bWT-injected four-cell embryos. RNA/DNA FISH analysis was performed. RNA/DNA FISH analysis revealed that the majority of Kdm6bWT-injected males showed one Xist RNA cloud or spot, while all of the Kdm6bMUT-injected males showed no signal (FIGS. 3C-3D). Furthermore, the majority of Kdm6bWT-injected females showed two Xist RNA clouds or/and spots, while most of the Kdm6bMUT-injected females showed one cloud (FIGS. 3C, 3E). These results demonstrate that loss of maternal H3K27me3 at the Xist locus induced maternal Xist derepression at the four-cell stage.

Example 4. Loss of H3K27Me3 Induces Maternal X-Chromosome Inactivation (XCI)

Figure 4A:
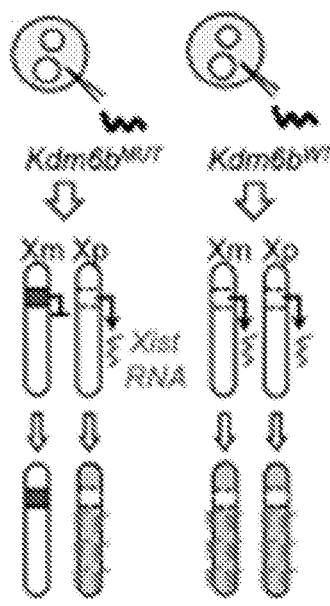
FIGS. 4A-4E show that loss of H3K27me3 induced maternal X-chromosome inactivation (XCI).
Figure 4B:
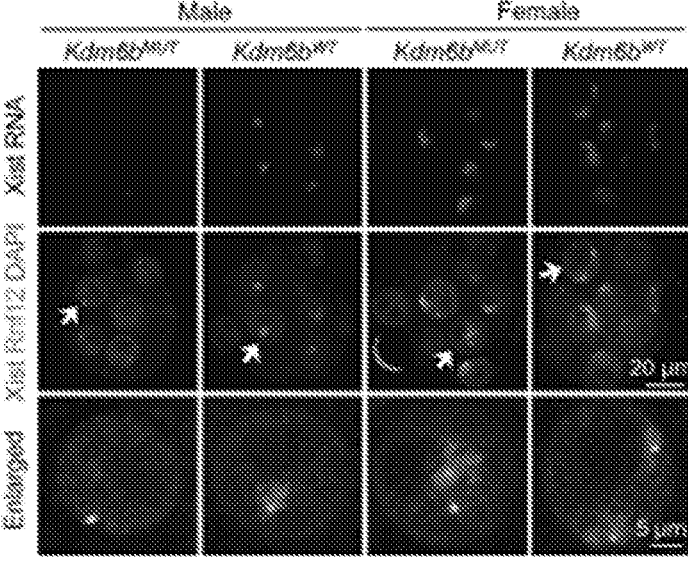
Figure 4C:
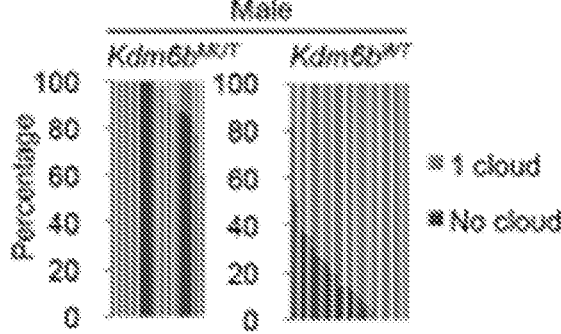
Figure 4D:
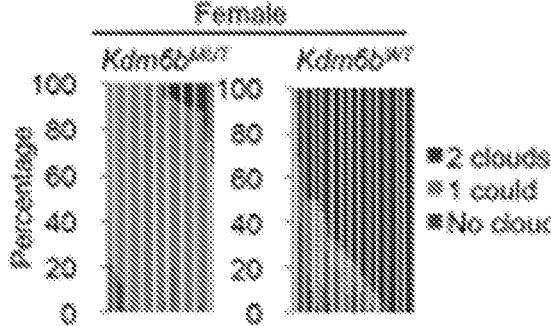
Figure 7:
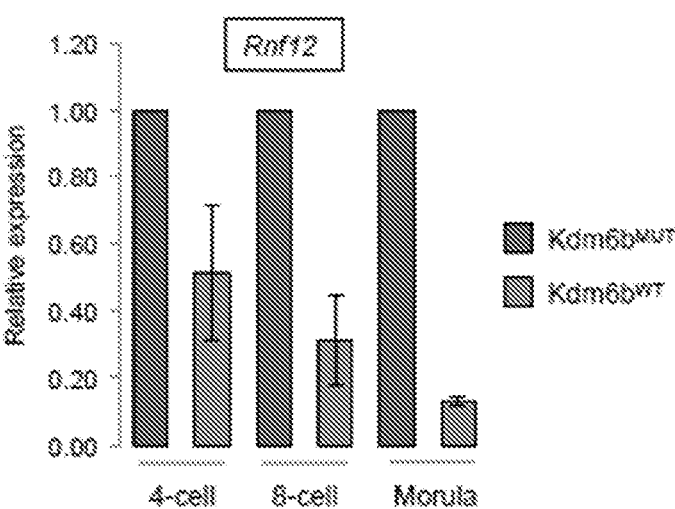
FIG. 7 is a graph depicting RT-qPCR analysis of Rnf12 in Kdm6b-injected embryos. The data were normalized to 18S, and then the values of Kdm6b$^{MUT}$ embryos were set as 1.0. Error bars indicate standard error (SE) of three biological replicates. Each experiment used a pool of 18-24 embryos per group. Note that Rnf12 is downregulated rather than upregulated in Kdm6b$^{WT}$-injected embryos. Without being bound by theory, this is likely due to maternal XCI occurring as early as the 4-cell stage in Kdm6b$^{WT}$-injected embryos, given that Rnf12 is a non-escapee X-linked gene (Borensztein et al. 2017. Nat Struct Mol Biol 24:226-233).

To examine whether maternal Xist expression continues until the morula stage (FIG. 4A). RNA/DNA FISH analysis was performed. Strikingly, the majority of Kdm6bWT-injected male and female embryos showed one and two RNA clouds, respectively, while most of the Kdm6bMUT-injected male and female embryos showed none and one RNA cloud, respectively (FIG. 4B-4D), indicating that the reactivated Xist is persistent. Although Xist can be up-regulated by Rnf12 overexpression (Tan et al. 2016. Proc Natl Acad Sci 113:3197-3202), RT-qPCR analysis found no evidence of Rnf12 up-regulation in Kdm6bWT-injected embryos (FIG. 7), excluding the possibility that Kdm6bWT-mediated Xist depression is due to Rnf12 overexpression.

Figure 4E:
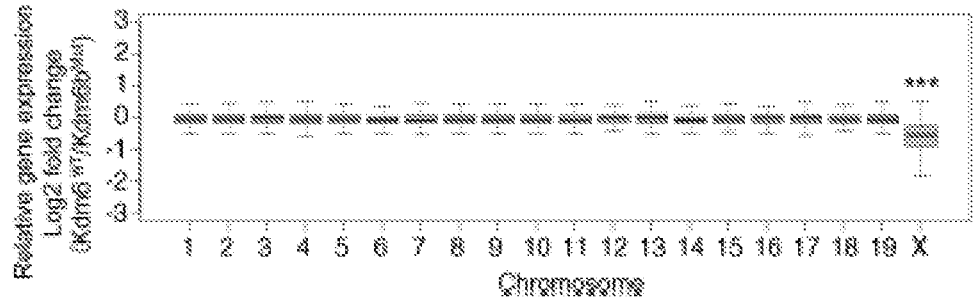
Figure 8A:
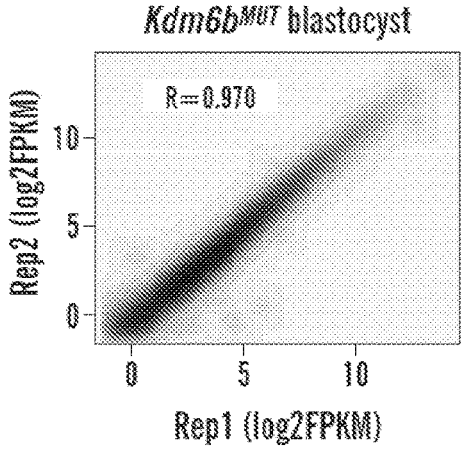
FIGS. 8A-8D show that maternal X chromosome inactivation in Kdm6bWT-injected blastocyst embryos. These results are related to those shown in FIGS. 4A-4E.
Figure 8A:
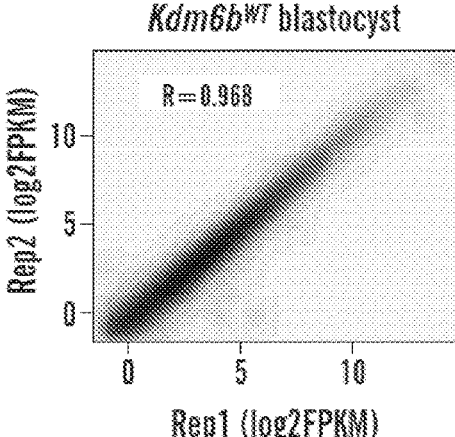
Figure 8B:
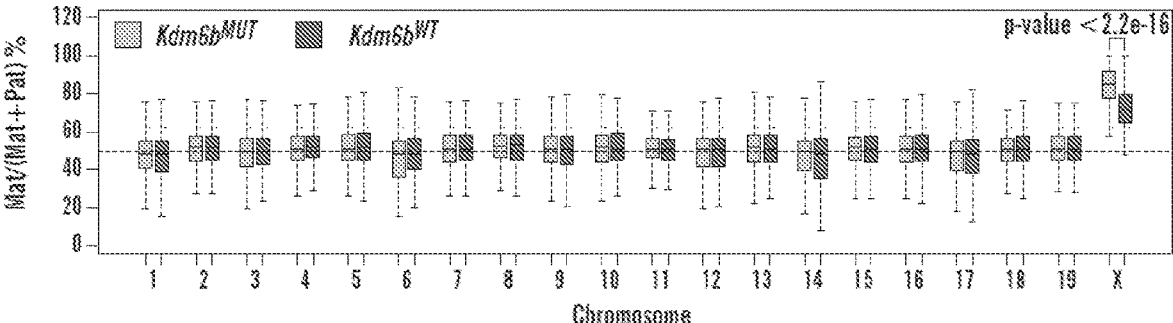
Figure 8C:
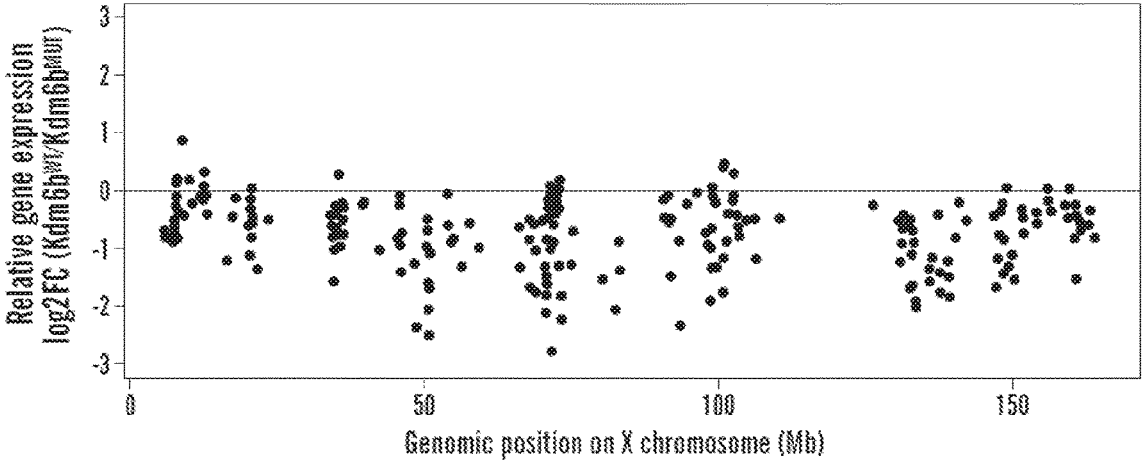
Figure 8D:
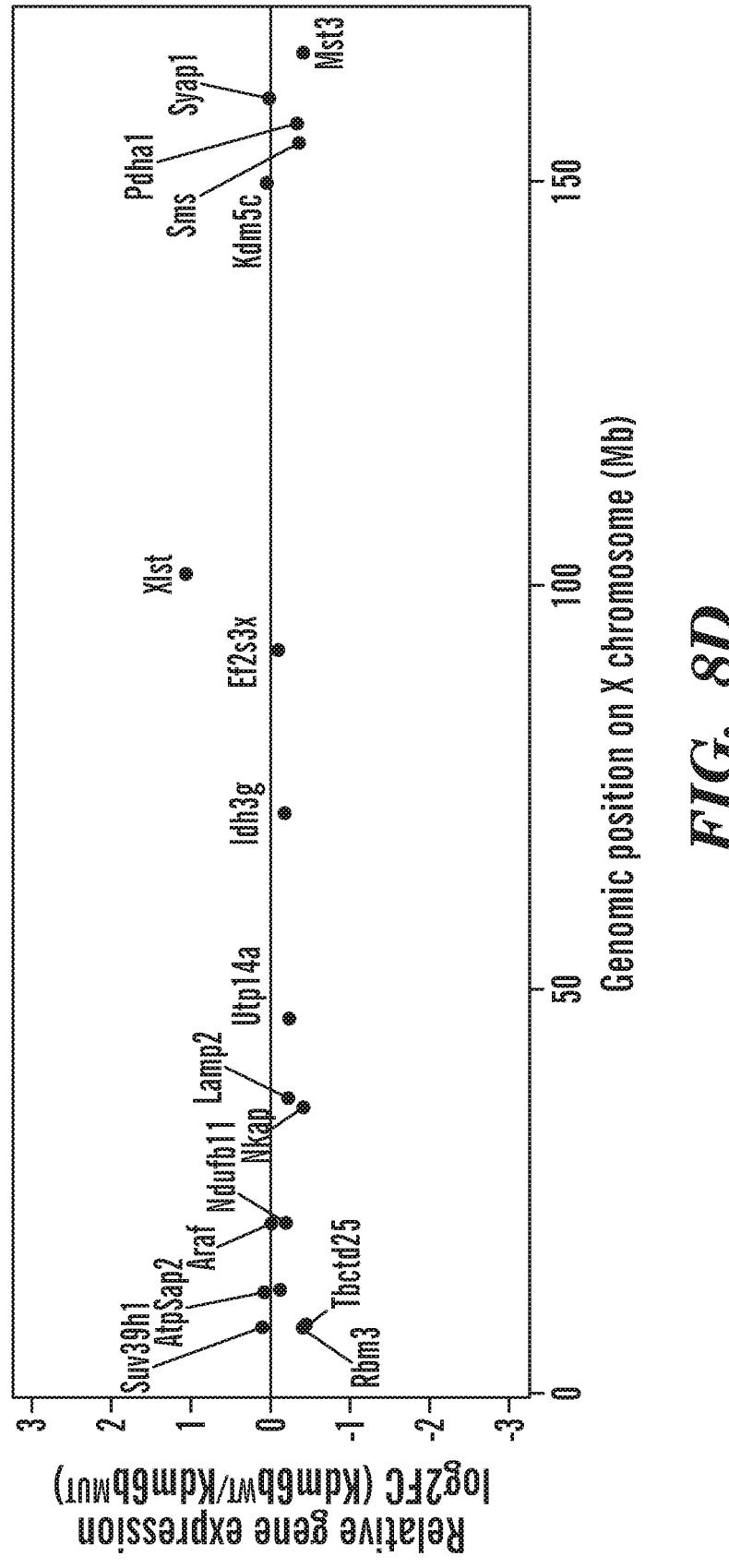

To determine whether maternal Xist expression leads to maternal XCI (FIG. 4A), RNA sequencing (RNA-seq) analysis was performed on early blastocyst stage hybrid mouse embryos with biological duplicates (FIG. 8A). Analysis of SNP information allowed examination of Xm-linked genes, which revealed that the expression level of Xm-linked genes, but not those of autosomal genes was significantly down-regulated in Kdm6bWT-injected embryos (FIG. 4E). Consistently, the maternal allele expression bias [Mat/(Mat+Pat)] of X-linked genes was significantly compromised in Kdm6bWT-injected embryos, although it was still >50% (FIG. 8B). These data demonstrate that maternal XCI occurs at a level milder than paternal XCI in Kdm6bWT-injected embryos. A closer examination of individual X-linked genes confirmed that most genes were down-regulated in Kdm6bWT-injected embryos (FIG. 8C), while genes known to escape imprinted XCI (Borensztein et al. 2017. Nat Struct Mol Biol 24:226-233) were unchanged (FIG. 8D). Without being bound by theory, this suggests that Kdm6b-mediated maternal XCI could recapitulate physiological XCI.

Taken together, the results described herein provide evidence that H3K27me3 serves as the imprinting mark of Xist. The domain-based regulation of maternal H3K27me3 at the Xist locus is an attractive observation and raises important questions. For example, how are the boundaries of the H3K27me3 domain defined during oogenesis? How does the first half (~200 kb) of the domain, spanning Xist and Zeche13, maintain the maternal allele-specific H3K27me3 enrichment in blastocyst embryos? Notably, this ~200-kb region appears to form a topological association domain (Giorgetti et al. 2014. Cell 157:950-963), implicating potential involvement of a protein such as CTCF in regulating chromatin boundaries. Interestingly, this domain highly overlaps transgenes whose insertion into an autosome recapitulated imprinted XCI (Okamoto et al. 2005. Nature 438:369-373). Without being bound by theory, this raises a possibility that a core element attracting Polycomb group complexes might exist in the region and contribute to imprinting establishment during oogenesis.

In conclusion, the present study thus not only identifies Xist as a new member of H3K27me3-dependent imprinted genes (Inoue et al. 2017), but also demonstrates the biological significance of H3K27me3-dependent genomic imprinting in safeguarding the Xm from XCI.

The results described above were obtained with the following materials and methods Collection of Mouse Oocytes All animal studies were performed in accordance with guidelines of the Institutional Animal Care and Use Committee at Harvard Medical School. The procedures of oocyte collection and in vitro fertilization were described previously (Inoue et al. 2017. Nature 547:419-424). The hybrid embryos used for SNP analysis in this study were obtained by in vitro fertilization of B6D2F1/J((BDF1) oocytes and PWK sperm (Jackson Laboratory, 003715)

mRNA Preparation and Injection

The construction and preparation of Kdm6b mRNA and microinjection into fertilized oocytes were described previously (Inoue et al. 2017. Nature 547:419-424). The Kdm4b construct was generated by cloning its cDNA amplicon into the pcDNA3.1-Flag-poly (A) 83 plasmid. mRNA was synthesized with mMES-SAGE mMACHINE T7 Ultra kit (Life technologies), purified by lithium chloride precipitation, and dissolved with nuclease-free water. The concentrations of injected mRNA of Kdm6b$^{WT}$ and Kdm6b$^{MUT}$ were 1800 ng/µL, and those of Kdm4b were 1000 or 2600 ng/µL.

Probe for FISH

A probe for Xist RNA was prepared by using Nick translation reagent kit (Abbott Molecular, 07J00-001) with Cy3-dCTP (GE Healthcare, PA53021). The template DNA was a plasmid coding the full-length mouse Xist gene (Addgene, 26760) (Wutz and Jaenisch. 2000. Mol Cell 5:695-705). A probe for DNA FISH was prepared using the same kit with Green-dUTP (Abbott Molecular, 02N32-050). The template DNA was a BAC clone containing the Rnf12 locus (RP23-36C20) (Fukuda et al. 2015. Development 142:4049-4055). The fluorescent probes were ethanol-precipitated with 5 µg of Cot-1 DNA (Life technologies), 5 µg of herring sperm DNA (Thermo Fisher Scientific), and 2.5 µg of yeast tRNA (Thermo Fisher Scientific, AM7119) and then dissolved with 20 µL of formamide (Thermo Fisher Scientific, 17899). The probes were stored at 4° C. Before being used, the probes (0.75 µL each) were mixed with 0.75 µL of Cot-1 DNA/formamide and 2.25 µL of 4×SSC/20% dextran (Millipore S4030). The probe mixtures were heated for 30 min at 80° C. and then transferred to a 37° C. incubator ("preannealed probes").

Whole-Mount RNA/DNA FISH

Four-cell or morula embryos were fixed at 46 or 78 hr. post-fertilization (hpf) in 2% paraformaldehyde (PFA) in PBS containing 0.5% Triton X-100 for 20 min at room temperature. After three washes with 0.1% BSA/PBS, embryos were treated with 0.1 N HCl containing 0.02% Triton X-100 for 15 min at 4° C. After three washes with 0.1% BSA/2×SSC, embryos were incubated in a series of 10%, 20%, and 50% formamide/2×SSC in a glass dish (Electron Microscopy Science, 705430-30) and incubated for 30 min. The samples were covered with mineral oil, heated for 30 min at 80° C., and then incubated for >30 min at 37° C. The embryos were then transferred into 4.5 µL of "preannealed probes," covered with mineral oil on another glass dish, and incubated for >24 hr. at 37° C. Embryos were washed with 42° C. prewarmed 0.1% BSA/2×SSC, left in the last drop for 30 min, and mounted on a glass slide in VectaShield with DAPI (Vector Laboratories). Fluorescence was detected under a laser-scanning confocal microscope (Zeiss, LSM800).

Whole-Mount Immunostaining

The procedure of immunostaining and quantification was described previously (Inoue et al. 2017. Nature 547:419-424).

Identification of the Maternal Allele-Biased H3K27Me3 Domain

The BED files, including RPKM (reads per kilobase per million mapped reads) values in 100-base-pair (bp) bins for H3K27me3 ChIP-seq in the inner cell mass (ICM), were from GSE76687 (Zheng et al. 2016. Mol Cell 63:1066-1079). BED files labeled maternal- or paternal-containing RPKM values for two parental alleles, and allelic reads were normalized to total read number. "bedtools makewindows" was used to generate 1-kb bins for the entire mm9 genome, and the RPKM value for each bin was calculated by "bedtools map." All of the bins were classified to three categories of "no signal," "biallelic," and "maternal-biased" using a signal cutoff of 1 and a fold change cutoff of 4. A sliding window approach was used to identify domains that were enriched for "maternal-biased" H3K27me3 bins. The criteria used were as follows: Within a window of 20 kb, the minimum number of "maternal-biased" bins was three, and the percentage of "maternal-biased" bins was larger than "biallelic" bins. Overlapped windows were merged by "bedtools merge." A total of 5986 domains was identified in the genome.

ULI-NChIP

At 78 hpf, ~110 morula embryos per group were briefly treated with acid Tyrode's solution (Sigma-Aldrich) to remove zona pellucida, washed with 0.2% BSA/PBS, and transferred to 1.5-mL tubes. The ULI-NChIP was performed using H3K27me3 antibody (Diagenode, C15410069) as described previously (Brind'Amour et al. 2015. Nat Commun 6:6033) with the following modifications. First, we used Beckman SPRIselect beads (Beckman Coulter) instead of Agencourt Ampure XP beads. Second, the sequencing library was prepared using NEBNext Ultra II DNA library preparation kit for Illumina (New England Biolabs). Third, PCR amplification was performed using Kapa Hifi hot start ready mix (Kapa Biosystems). Lastly, no size selection was performed. For input samples, 10% volume of the chromatin lysate was taken and used for library construction and sequencing. The quantification and sequencing of the libraries were described previously (Inoue et al. 2017. Nature 547:419-424).

Data Analysis of ULI-NChIP

For normalization between Kdm6bMUT and Kdm6bWT samples, a strategy similar to MAnorm (Shao et al. 2012. Genome Biol 13: R16) was used. First, the common peaks were identified between the Kdm6bMUT and Kdm6bWT samples. Next, all samples were normalized to the highest coverage samples based on the RPKM value for each sample within the common peaks. SNP-specific reads were normalized to total uniquely mapped reads per library and further normalized to the highest-coverage allele based on the sum of SNP-specific reads per allele.

Reverse Transcription and Real-Time PCR Analysis

Kdm6b-injected embryos were collected at 46 hpf (four-cell), 60 hpf (eight-cell), and 78 hpf (morula). The procedures of reverse transcription and real-time PCR analysis were described previously (Inoue and Zhang. 2014. Nat Struct Mol Biol 21:609-616) except for the use of random primers for reverse transcription in this study. Primer sequences used for real-time PCR were as follows: 18S-F (5'-TTG ACGGAAGGGCACCACCAG-3' (SEQ ID NO: 6)), 18S-R (5'-GCACCACCACCCACGGA ATCG-3' (SEQ ID NO: 7)), Rnf12-F (5'-TTTGTCGCAGGGCAGTCTTA-3' (SEQ ID NO: 8)), and Rnf12-R (5'-GTTTGCCCATCAC-TATTCCAGC-3 (SEQ ID NO: 9).

RNA-Seq and Data Analysis

Blastocyst embryos at 96 hpf were treated briefly with acid Tyrode's solution, washed by 0.2% BSA/PBS, and stored in PCR tubes at −80° C. Forty to 46 embryos per group were pooled and used for RNA-seq. RNA-seq libraries were prepared as described previously [(Inoue et al. 2017) with the exception of using Nextera XT DNA library preparation kit (Illumina) following cDNA amplification.

Statistical Analyses

Statistical analyses were implemented with R (http://www.r-project.org). Pearson's R coefficient was calculated using the "cor" function with default parameters. For FIG. 8B, Mann-Whitney U-Test was performed with the R function "wilcox.test."

Code Availability

A customized pipeline was used to split the alignment of sequencing data from hybrid embryos to their parental origin based on SNP information. The code is available at https://github.com/lanjiangboston/UniversalSNPsplit.

Data Availability

ChIP-seq and RNA-seq data sets generated herein are deposited at the Gene Expression Omnibus database under accession number GSE103714. The WGBS data set for GV oocytes was downloaded from http://www.nodai-genom-e.org/mouse.html?lang=en (Kobayashi et al. 2012. PLOS Genet 8: e1002440). H3K27me3 ChIP-seq data sets were downloaded from GSE76687 (Zheng et al. 2016. Mol Cell 63:1066-1079). The oocyte DNase I-seq data set was from GSE92605 (Inoue et al. 2017. Nature 547:419-424). The BAM file and peak file of ENCODE data were downloaded from https://www.encodeproject.org/files/ENCFF001KDT. Morula embryo H3K27me3 ChIP-seq data sets were from GSE73952 (Liu et al. 2016. Nature 537:558-562).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, and accession numbers mentioned in this specification are herein incorporated by reference to the same extent as if each independent patent, publication, and accession number was specifically and individually indicated to be incorporated by reference.

What is claimed is:

1. A method for depleting and detecting maternal H3K27me3 at an imprinted X-inactivation-specific transcript (Xist) locus of a maternal X chromosome and inducing maternal Xist derepression and maternal X chromosome inactivation (XCI) in a mammalian embryo generated by Somatic Cell Nuclear Transfer (SCNT), the method comprising:

injecting the embryo generated via SCNT with an H3K27me3-specific demethylase Kdm6b polypeptide comprising the amino acid sequence as set forth in SEQ ID NO: 2 and having H3K27me3-specific demethylase activity or a polynucleotide encoding said Kdm6b polypeptide; and detecting in the Kdm6b-injected embryo a down-regulated expression level of maternal X-linked genes compared to the levels of autosomal genes and genes that escape X-chromosome inactivation; wherein (i) the Kdm6b-injected embryo exhibits loss of the maternal H3K27me3 domain at the Xist locus; and (ii) maternal allele expression bias of X-linked genes is greater than 35-60% in the injected embryo compared with an embryo not injected with the Kdm6b polypeptide or with a polynucleotide encoding the Kdm6b polypeptide.

2. The method of claim 1, wherein the embryo is injected with an mRNA encoding the Kdm6b H3K27me3-specific demethylase.

3. The method of claim 2, wherein the embryo is injected with between 1000 and 2000 ng/μl of the Kdm6b-encoding mRNA.

4. The method of claim 3, wherein the embryo is injected with 1800 ng/μL of the Kdm6b-encoding mRNA.

5. The method of claim 1, wherein the polynucleotide encoding Kdm6b is present in a mammalian expression vector.

6. The method of claim 5, wherein the mammalian expression vector comprises a promoter directing constitutive or inducible expression of the Kdm6b H3K27me3-specific demethylase.

7. The method of claim 1, wherein the method does not significantly change the expression of genes that escape X-chromosome imprinting.

8. The method of claim 1, wherein the Kdm6b-injected embryo is an early blastocyst stage embryo.

9. The method of claim 1, further comprising detecting the loss of the maternal H3K27me3 domain at the Xist locus in the Kdm6b-injected embryo by performing ultralow input native combined chromatin immunoprecipitation and next-generation sequencing (ChIP-seq) and single-nucleotide polymorphism (SNP) analyses.

10. The method of claim 1, wherein the detecting step is performed by RNA sequencing and single-nucleotide polymorphism (SNP) analyses.

11. A method for depleting and detecting maternal H3K27me3 at an imprinted X-inactivation-specific transcript (Xist) locus of a maternal X chromosome and inducing maternal Xist derepression and maternal X chromosome inactivation (XCI) in a mammalian embryo generated by Somatic Cell Nuclear Transfer (SCNT), the method comprising:

injecting the embryo generated via SCNT with an H3K27me3-specific demethylase Kdm6b polypeptide comprising an amino acid sequence with at least 98% identity to SEQ ID NO: 2 and having H3K27me3-specific demethylase activity or a polynucleotide encoding said Kdm6b polypeptide; and detecting in the Kdm6b-injected embryo a down-regulated expression level of maternal X-linked genes compared to the levels of autosomal genes and genes that escape X-chromosome inactivation; wherein (i) the Kdm6b-injected embryo exhibits loss of the maternal H3K27me3 domain at the Xist locus; and (ii) maternal allele expression bias of X-linked genes is greater than 35-60% in the injected embryo compared with an embryo not injected with the Kdm6b polypeptide or with a polynucleotide encoding the Kdm6b polypeptide.

12. The method of claim 11, wherein the polynucleotide encoding the Kdm6b polypeptide is an mRNA.

13. The method of claim 11, wherein the polynucleotide encoding Kdm6b is present in a mammalian expression vector and/or wherein the polynucleotide encoding Kdm6b is present in a mammalian expression vector which comprises a promoter directing constitutive or inducible expression of the Kdm6b H3K27me3-specific demethylase.

* * * * *

SEQUENCE LISTING

```
<160> NUMBER OF SEQ ID NOS: 9

<210> SEQ ID NO 1
<211> LENGTH: 1401
<212> TYPE: PRT
<213> ORGANISM: Homo sapiens

<400> SEQUENCE: 1

Met Lys Ser Cys Gly Val Ser Leu Ala Thr Ala Ala Ala Ala Ala Ala
1               5                   10                  15

Ala Phe Gly Asp Glu Glu Lys Lys Met Ala Ala Gly Lys Ala Ser Gly
            20                  25                  30

Glu Ser Glu Glu Ala Ser Pro Ser Leu Thr Ala Glu Glu Arg Glu Ala
        35                  40                  45

Leu Gly Gly Leu Asp Ser Arg Leu Phe Gly Phe Val Arg Phe His Glu
    50                  55                  60

Asp Gly Ala Arg Thr Lys Ala Leu Leu Gly Lys Ala Val Arg Cys Tyr
65                  70                  75                  80

Glu Ser Leu Ile Leu Lys Ala Glu Gly Lys Val Glu Ser Asp Phe Phe
                85                  90                  95

Cys Gln Leu Gly His Phe Asn Leu Leu Leu Glu Asp Tyr Pro Lys Ala
            100                 105                 110

Leu Ser Ala Tyr Gln Arg Tyr Tyr Ser Leu Gln Ser Asp Tyr Trp Lys
        115                 120                 125

Asn Ala Ala Phe Leu Tyr Gly Leu Gly Leu Val Tyr Phe His Tyr Asn
    130                 135                 140

Ala Phe Gln Trp Ala Ile Lys Ala Phe Gln Glu Val Leu Tyr Val Asp
145                 150                 155                 160

Pro Ser Phe Cys Arg Ala Lys Glu Ile His Leu Arg Leu Gly Leu Met
                165                 170                 175
```

```
Phe Lys Val Asn Thr Asp Tyr Glu Ser Ser Leu Lys His Phe Gln Leu
        180                 185                 190

Ala Leu Val Asp Cys Asn Pro Cys Thr Leu Ser Asn Ala Glu Ile Gln
        195                 200                 205

Phe His Ile Ala His Leu Tyr Glu Thr Gln Arg Lys Tyr His Ser Ala
        210                 215                 220

Lys Glu Ala Tyr Glu Gln Leu Leu Gln Thr Glu Asn Leu Ser Ala Gln
225                 230                 235                 240

Val Lys Ala Thr Val Leu Gln Gln Leu Gly Trp Met His His Thr Val
                245                 250                 255

Asp Leu Leu Gly Asp Lys Ala Thr Lys Glu Ser Tyr Ala Ile Gln Tyr
                260                 265                 270

Leu Gln Lys Ser Leu Glu Ala Asp Pro Asn Ser Gly Gln Ser Trp Tyr
                275                 280                 285

Phe Leu Gly Arg Cys Tyr Ser Ser Ile Gly Lys Val Gln Asp Ala Phe
        290                 295                 300

Ile Ser Tyr Arg Gln Ser Ile Asp Lys Ser Glu Ala Ser Ala Asp Thr
305                 310                 315                 320

Trp Cys Ser Ile Gly Val Leu Tyr Gln Gln Gln Asn Gln Pro Met Asp
                325                 330                 335

Ala Leu Gln Ala Tyr Ile Cys Ala Val Gln Leu Asp His Gly His Ala
                340                 345                 350

Ala Ala Trp Met Asp Leu Gly Thr Leu Tyr Glu Ser Cys Asn Gln Pro
        355                 360                 365

Gln Asp Ala Ile Lys Cys Tyr Leu Asn Ala Thr Arg Ser Lys Ser Cys
        370                 375                 380

Ser Asn Thr Ser Ala Leu Ala Ala Arg Ile Lys Tyr Leu Gln Ala Gln
385                 390                 395                 400

Leu Cys Asn Leu Pro Gln Gly Ser Leu Gln Asn Lys Thr Lys Leu Leu
                405                 410                 415

Pro Ser Ile Glu Glu Ala Trp Ser Leu Pro Ile Pro Ala Glu Leu Thr
                420                 425                 430

Ser Arg Gln Gly Ala Met Asn Thr Ala Gln Gln Asn Thr Ser Asp Asn
        435                 440                 445

Trp Ser Gly Gly His Ala Val Ser His Pro Pro Val Gln Gln Gln Ala
        450                 455                 460

His Ser Trp Cys Leu Thr Pro Gln Lys Leu Gln His Leu Glu Gln Leu
465                 470                 475                 480

Arg Ala Asn Arg Asn Asn Leu Asn Pro Ala Gln Lys Leu Met Leu Glu
                485                 490                 495

Gln Leu Glu Ser Gln Phe Val Leu Met Gln Gln His Gln Met Arg Pro
        500                 505                 510

Thr Gly Val Ala Gln Val Arg Ser Thr Gly Ile Pro Asn Gly Pro Thr
        515                 520                 525

Ala Asp Ser Ser Leu Pro Thr Asn Ser Val Ser Gly Gln Gln Pro Gln
        530                 535                 540

Leu Ala Leu Thr Arg Val Pro Ser Val Ser Gln Pro Gly Val Arg Pro
545                 550                 555                 560

Ala Cys Pro Gly Gln Pro Leu Ala Asn Gly Pro Phe Ser Ala Gly His
                565                 570                 575

Val Pro Cys Ser Thr Ser Arg Thr Leu Gly Ser Thr Asp Thr Ile Leu
                580                 585                 590
```

```
Ile Gly Asn Asn His Ile Thr Gly Ser Gly Ser Asn Gly Asn Val Pro
        595                 600             605

Tyr Leu Gln Arg Asn Ala Leu Thr Leu Pro His Asn Arg Thr Asn Leu
        610                 615             620

Thr Ser Ser Ala Glu Glu Pro Trp Lys Asn Gln Leu Ser Asn Ser Thr
625                 630             635                 640

Gln Gly Leu His Lys Gly Gln Ser Ser His Ser Ala Gly Pro Asn Gly
            645             650             655

Glu Arg Pro Leu Ser Ser Thr Gly Pro Ser Gln His Leu Gln Ala Ala
            660             665             670

Gly Ser Gly Ile Gln Asn Gln Asn Gly His Pro Thr Leu Pro Ser Asn
            675             680             685

Ser Val Thr Gln Gly Ala Ala Leu Asn His Leu Ser Ser His Thr Ala
        690             695             700

Thr Ser Gly Gly Gln Gln Gly Ile Thr Leu Thr Lys Glu Ser Lys Pro
705             710             715                 720

Ser Gly Asn Ile Leu Thr Val Pro Glu Thr Ser Arg His Thr Gly Glu
            725             730             735

Thr Pro Asn Ser Thr Ala Ser Val Glu Gly Leu Pro Asn His Val His
            740             745             750

Gln Met Thr Ala Asp Ala Val Cys Ser Pro Ser His Gly Asp Ser Lys
        755             760             765

Ser Pro Gly Leu Leu Ser Ser Asp Asn Pro Gln Leu Ser Ala Leu Leu
        770             775             780

Met Gly Lys Ala Asn Asn Asn Val Gly Thr Gly Thr Cys Asp Lys Val
785             790             795                 800

Asn Asn Ile His Pro Ala Val His Thr Lys Thr Asp Asn Ser Val Ala
                805             810             815

Ser Ser Pro Ser Ser Ala Ile Ser Thr Ala Thr Pro Ser Pro Lys Ser
            820             825             830

Thr Glu Gln Thr Thr Thr Asn Ser Val Thr Ser Leu Asn Ser Pro His
        835             840             845

Ser Gly Leu His Thr Ile Asn Gly Glu Gly Met Glu Glu Ser Gln Ser
        850             855             860

Pro Met Lys Thr Asp Leu Leu Leu Val Asn His Lys Pro Ser Pro Gln
865             870             875                 880

Ile Ile Pro Ser Met Ser Val Ser Ile Tyr Pro Ser Ser Ala Glu Val
            885             890             895

Leu Lys Ala Cys Arg Asn Leu Gly Lys Asn Gly Leu Ser Asn Ser Ser
            900             905             910

Ile Leu Leu Asp Lys Cys Pro Pro Arg Pro Pro Ser Ser Pro Tyr
            915             920             925

Pro Pro Leu Pro Lys Asp Lys Leu Asn Pro Pro Thr Pro Ser Ile Tyr
        930             935             940

Leu Glu Asn Lys Arg Asp Ala Phe Phe Pro Pro Leu His Gln Phe Cys
945             950             955                 960

Thr Asn Pro Asn Asn Pro Val Thr Val Ile Arg Gly Leu Ala Gly Ala
                965             970             975

Leu Lys Leu Asp Leu Gly Leu Phe Ser Thr Lys Thr Leu Val Glu Ala
            980             985             990

Asn Asn Glu His Met Val Glu Val  Arg Thr Gln Leu Leu  Gln Pro Ala
        995             1000             1005
```

-continued

```
Asp Glu Asn Trp Asp Pro Thr  Gly Thr Lys Lys Ile  Trp His Cys
    1010                1015          1020

Glu Ser Asn Arg Ser His Thr  Thr Ile Ala Lys Tyr  Ala Gln Tyr
    1025                1030          1035

Gln Ala Ser Ser Phe Gln Glu  Ser Leu Arg Glu Glu  Asn Glu Lys
    1040                1045          1050

Arg Ser His His Lys Asp His  Ser Asp Ser Glu Ser  Thr Ser Ser
    1055                1060          1065

Asp Asn Ser Gly Arg Arg Arg  Lys Gly Pro Phe Lys  Thr Ile Lys
    1070                1075          1080

Phe Gly Thr Asn Ile Asp Leu  Ser Asp Asp Lys Lys  Trp Lys Leu
    1085                1090          1095

Gln Leu His Glu Leu Thr Lys  Leu Pro Ala Phe Val  Arg Val Val
    1100                1105          1110

Ser Ala Gly Asn Leu Leu Ser  His Val Gly His Thr  Ile Leu Gly
    1115                1120          1125

Met Asn Thr Val Gln Leu Tyr  Met Lys Val Pro Gly  Ser Arg Thr
    1130                1135          1140

Pro Gly His Gln Glu Asn Asn  Asn Phe Cys Ser Val  Asn Ile Asn
    1145                1150          1155

Ile Gly Pro Gly Asp Cys Glu  Trp Phe Val Val Pro  Glu Gly Tyr
    1160                1165          1170

Trp Gly Val Leu Asn Asp Phe  Cys Glu Lys Asn Asn  Leu Asn Phe
    1175                1180          1185

Leu Met Gly Ser Trp Trp Pro  Asn Leu Glu Asp Leu  Tyr Glu Ala
    1190                1195          1200

Asn Val Pro Val Tyr Arg Phe  Ile Gln Arg Pro Gly  Asp Leu Val
    1205                1210          1215

Trp Ile Asn Ala Gly Thr Val  His Trp Val Gln Ala  Ile Gly Trp
    1220                1225          1230

Cys Asn Asn Ile Ala Trp Asn  Val Gly Pro Leu Thr  Ala Cys Gln
    1235                1240          1245

Tyr Lys Leu Ala Val Glu Arg  Tyr Glu Trp Asn Lys  Leu Gln Ser
    1250                1255          1260

Val Lys Ser Ile Val Pro Met  Val His Leu Ser Trp  Asn Met Ala
    1265                1270          1275

Arg Asn Ile Lys Val Ser Asp  Pro Lys Leu Phe Glu  Met Ile Lys
    1280                1285          1290

Tyr Cys Leu Leu Arg Thr Leu  Lys Gln Cys Gln Thr  Leu Arg Glu
    1295                1300          1305

Ala Leu Ile Ala Ala Gly Lys  Glu Ile Ile Trp His  Gly Arg Thr
    1310                1315          1320

Lys Glu Glu Pro Ala His Tyr  Cys Ser Ile Cys Glu  Val Glu Val
    1325                1330          1335

Phe Asp Leu Leu Phe Val Thr  Asn Glu Ser Asn Ser  Arg Lys Thr
    1340                1345          1350

Tyr Ile Val His Cys Gln Asp  Cys Ala Arg Lys Thr  Ser Gly Asn
    1355                1360          1365

Leu Glu Asn Phe Val Val Leu  Glu Gln Tyr Lys Met  Glu Asp Leu
    1370                1375          1380

Met Gln Val Tyr Asp Gln Phe  Thr Leu Ala Pro Pro  Leu Pro Ser
    1385                1390          1395
```

-continued

```
Ala Ser  Ser
    1400

<210> SEQ ID NO 2
<211> LENGTH: 1643
<212> TYPE: PRT
<213> ORGANISM: Homo sapiens

<400> SEQUENCE: 2

Met His Arg Ala Val Asp Pro Pro Gly Ala Arg Ala Ala Arg Glu Ala
1               5                   10                  15

Phe Ala Leu Gly Gly Leu Ser Cys Ala Gly Ala Trp Ser Ser Cys Pro
            20                  25                  30

Pro His Pro Pro Pro Arg Ser Ala Trp Leu Pro Gly Gly Arg Cys Ser
        35                  40                  45

Ala Ser Ile Gly Gln Pro Pro Leu Pro Ala Pro Leu Pro Pro Ser His
    50                  55                  60

Gly Ser Ser Ser Gly His Pro Ser Lys Pro Tyr Tyr Ala Pro Gly Ala
65                  70                  75                  80

Pro Thr Pro Arg Pro Leu His Gly Lys Leu Glu Ser Leu His Gly Cys
                85                  90                  95

Val Gln Ala Leu Leu Arg Glu Pro Ala Gln Pro Gly Leu Trp Glu Gln
            100                 105                 110

Leu Gly Gln Leu Tyr Glu Ser Glu His Asp Ser Glu Glu Ala Thr Arg
            115                 120                 125

Cys Tyr His Ser Ala Leu Arg Tyr Gly Gly Ser Phe Ala Glu Leu Gly
    130                 135                 140

Pro Arg Ile Gly Arg Leu Gln Gln Ala Gln Leu Trp Asn Phe His Thr
145                 150                 155                 160

Gly Ser Cys Gln His Arg Ala Lys Val Leu Pro Pro Leu Glu Gln Val
                165                 170                 175

Trp Asn Leu Leu His Leu Glu His Lys Arg Asn Tyr Gly Ala Lys Arg
            180                 185                 190

Gly Gly Pro Pro Val Lys Arg Ala Ala Glu Pro Pro Val Val Gln Pro
            195                 200                 205

Val Pro Pro Ala Ala Leu Ser Gly Pro Ser Gly Glu Glu Gly Leu Ser
    210                 215                 220

Pro Gly Gly Lys Arg Arg Arg Gly Cys Asn Ser Glu Gln Thr Gly Leu
225                 230                 235                 240

Pro Pro Gly Leu Pro Leu Pro Pro Pro Leu Pro Pro Pro Pro Pro Pro
            245                 250                 255

Pro Pro Pro Pro Pro Pro Pro Leu Pro Gly Leu Ala Thr Ser Pro
            260                 265                 270

Pro Phe Gln Leu Thr Lys Pro Gly Leu Trp Ser Thr Leu His Gly Asp
            275                 280                 285

Ala Trp Gly Pro Glu Arg Lys Gly Ser Ala Pro Pro Glu Arg Gln Glu
    290                 295                 300

Gln Arg His Ser Leu Pro His Pro Tyr Pro Tyr Pro Ala Pro Ala Tyr
305                 310                 315                 320

Thr Ala His Pro Pro Gly His Arg Leu Val Pro Ala Ala Pro Pro Gly
                325                 330                 335

Pro Gly Pro Arg Pro Pro Gly Ala Glu Ser His Gly Cys Leu Pro Ala
            340                 345                 350

Thr Arg Pro Pro Gly Ser Asp Leu Arg Glu Ser Arg Val Gln Arg Ser
            355                 360                 365
```

-continued

```
Arg Met Asp Ser Ser Val Ser Pro Ala Ala Thr Thr Ala Cys Val Pro
    370             375             380

Tyr Ala Pro Ser Arg Pro Pro Gly Leu Pro Gly Thr Thr Thr Ser Ser
385             390             395             400

Ser Ser Ser Ser Ser Ser Asn Thr Gly Leu Arg Gly Val Glu Pro Asn
                405             410             415

Pro Gly Ile Pro Gly Ala Asp His Tyr Gln Thr Pro Ala Leu Glu Val
            420             425             430

Ser His His Gly Arg Leu Gly Pro Ser Ala His Ser Ser Arg Lys Pro
            435             440             445

Phe Leu Gly Ala Pro Ala Ala Thr Pro His Leu Ser Leu Pro Pro Gly
    450             455             460

Pro Ser Ser Pro Pro Pro Pro Cys Pro Arg Leu Leu Arg Pro Pro
465             470             475             480

Pro Pro Pro Ala Trp Leu Lys Gly Pro Ala Cys Arg Ala Ala Arg Glu
            485             490             495

Asp Gly Glu Ile Leu Glu Glu Leu Phe Phe Gly Thr Glu Gly Pro Pro
            500             505             510

Arg Pro Ala Pro Pro Pro Leu Pro His Arg Glu Gly Phe Leu Gly Pro
            515             520             525

Pro Ala Ser Arg Phe Ser Val Gly Thr Gln Asp Ser His Thr Pro Pro
    530             535             540

Thr Pro Pro Thr Pro Thr Thr Ser Ser Ser Asn Ser Asn Ser Gly Ser
545             550             555             560

His Ser Ser Ser Pro Ala Gly Pro Val Ser Phe Pro Pro Pro Tyr
            565             570             575

Leu Ala Arg Ser Ile Asp Pro Leu Pro Arg Pro Pro Ser Pro Ala Gln
            580             585             590

Asn Pro Gln Asp Pro Pro Leu Val Pro Leu Thr Leu Ala Leu Pro Pro
            595             600             605

Ala Pro Pro Ser Ser Cys His Gln Asn Thr Ser Gly Ser Phe Arg Arg
            610             615             620

Pro Glu Ser Pro Arg Pro Arg Val Ser Phe Pro Lys Thr Pro Glu Val
625             630             635             640

Gly Pro Gly Pro Pro Pro Gly Pro Leu Ser Lys Ala Pro Gln Pro Val
            645             650             655

Pro Pro Gly Val Gly Glu Leu Pro Ala Arg Gly Pro Arg Leu Phe Asp
            660             665             670

Phe Pro Pro Thr Pro Leu Glu Asp Gln Phe Glu Glu Pro Ala Glu Phe
            675             680             685

Lys Ile Leu Pro Asp Gly Leu Ala Asn Ile Met Lys Met Leu Asp Glu
            690             695             700

Ser Ile Arg Lys Glu Glu Glu Gln Gln Gln His Glu Ala Gly Val Ala
705             710             715             720

Pro Gln Pro Pro Leu Lys Glu Pro Phe Ala Ser Leu Gln Ser Pro Phe
            725             730             735

Pro Thr Asp Thr Ala Pro Thr Thr Thr Ala Pro Ala Val Ala Val Thr
            740             745             750

Thr Thr Thr Thr Thr Thr Thr Thr Thr Thr Ala Thr Gln Glu Glu Glu
            755             760             765

Lys Lys Pro Pro Pro Ala Leu Pro Pro Pro Pro Leu Ala Lys Phe
770             775             780
```

```
Pro Pro Pro Ser Gln Pro Gln Pro Pro Pro Pro Pro Pro Ser Pro
785             790         795                 800

Ala Ser Leu Leu Lys Ser Leu Ala Ser Val Leu Glu Gly Gln Lys Tyr
                805             810                 815

Cys Tyr Arg Gly Thr Gly Ala Ala Val Ser Thr Arg Pro Gly Pro Leu
            820             825             830

Pro Thr Thr Gln Tyr Ser Pro Gly Pro Pro Ser Gly Ala Thr Ala Leu
        835             840             845

Pro Pro Thr Ser Ala Ala Pro Ser Ala Gln Gly Ser Pro Gln Pro Ser
    850             855             860

Ala Ser Ser Ser Ser Gln Phe Ser Thr Ser Gly Gly Pro Trp Ala Arg
865             870             875                 880

Glu Arg Arg Ala Gly Glu Glu Pro Val Pro Gly Pro Met Thr Pro Thr
            885             890             895

Gln Pro Pro Pro Pro Leu Ser Leu Pro Pro Ala Arg Ser Glu Ser Glu
        900             905             910

Val Leu Glu Glu Ile Ser Arg Ala Cys Glu Thr Leu Val Glu Arg Val
    915             920             925

Gly Arg Ser Ala Thr Asp Pro Ala Asp Pro Val Asp Thr Ala Glu Pro
930             935             940

Ala Asp Ser Gly Thr Glu Arg Leu Leu Pro Pro Ala Gln Ala Lys Glu
945             950             955                 960

Glu Ala Gly Gly Val Ala Ala Val Ser Gly Ser Cys Lys Arg Arg Gln
            965             970             975

Lys Glu His Gln Lys Glu His Arg Arg His Arg Arg Ala Cys Lys Asp
            980             985             990

Ser Val Gly Arg Arg Pro Arg Glu  Gly Arg Ala Lys Ala  Lys Ala Lys
        995             1000                 1005

Val Pro Lys Glu Lys Ser Arg  Arg Val Leu Gly Asn  Leu Asp Leu
    1010             1015                 1020

Gln Ser  Glu Glu Ile Gln Gly  Arg Glu Lys Ser Arg  Pro Asp Leu
    1025             1030                 1035

Gly Gly  Ala Ser Lys Ala Lys  Pro Pro Thr Ala Pro  Ala Pro Pro
    1040             1045                 1050

Ser Ala  Pro Ala Pro Ser Ala  Gln Pro Thr Pro Pro  Ser Ala Ser
    1055             1060                 1065

Val Pro  Gly Lys Lys Ala Arg  Glu Glu Ala Pro Gly  Pro Pro Gly
    1070             1075                 1080

Val Ser  Arg Ala Asp Met Leu  Lys Leu Arg Ser Leu  Ser Glu Gly
    1085             1090                 1095

Pro Pro  Lys Glu Leu Lys Ile  Arg Leu Ile Lys Val  Glu Ser Gly
    1100             1105                 1110

Asp Lys  Glu Thr Phe Ile Ala  Ser Glu Val Glu Glu  Arg Arg Leu
    1115             1120                 1125

Arg Met  Ala Asp Leu Thr Ile  Ser His Cys Ala Ala  Asp Val Val
    1130             1135                 1140

Arg Ala  Ser Arg Asn Ala Lys  Val Lys Gly Lys Phe  Arg Glu Ser
    1145             1150                 1155

Tyr Leu  Ser Pro Ala Gln Ser  Val Lys Pro Lys Ile  Asn Thr Glu
    1160             1165                 1170

Glu Lys  Leu Pro Arg Glu Lys  Leu Asn Pro Pro Thr  Pro Ser Ile
    1175             1180                 1185
```

-continued

```
Tyr Leu Glu Ser Lys Arg Asp   Ala Phe Ser Pro Val   Leu Leu Gln
    1190              1195              1200

Phe Cys Thr Asp Pro Arg Asn   Pro Ile Thr Val Ile   Arg Gly Leu
    1205              1210              1215

Ala Gly Ser Leu Arg Leu Asn   Leu Gly Leu Phe Ser   Thr Lys Thr
    1220              1225              1230

Leu Val Glu Ala Ser Gly Glu   His Thr Val Glu Val   Arg Thr Gln
    1235              1240              1245

Val Gln Gln Pro Ser Asp Glu   Asn Trp Asp Leu Thr   Gly Thr Arg
    1250              1255              1260

Gln Ile Trp Pro Cys Glu Ser   Ser Arg Ser His Thr   Thr Ile Ala
    1265              1270              1275

Lys Tyr Ala Gln Tyr Gln Ala   Ser Ser Phe Gln Glu   Ser Leu Gln
    1280              1285              1290

Glu Glu Lys Glu Ser Glu Asp   Glu Glu Ser Glu Glu   Pro Asp Ser
    1295              1300              1305

Thr Thr Gly Thr Pro Pro Ser   Ser Ala Pro Asp Pro   Lys Asn His
    1310              1315              1320

His Ile Ile Lys Phe Gly Thr   Asn Ile Asp Leu Ser   Asp Ala Lys
    1325              1330              1335

Arg Trp Lys Pro Gln Leu Gln   Glu Leu Leu Lys Leu   Pro Ala Phe
    1340              1345              1350

Met Arg Val Thr Ser Thr Gly   Asn Met Leu Ser His   Val Gly His
    1355              1360              1365

Thr Ile Leu Gly Met Asn Thr   Val Gln Leu Tyr Met   Lys Val Pro
    1370              1375              1380

Gly Ser Arg Thr Pro Gly His   Gln Glu Asn Asn Asn   Phe Cys Ser
    1385              1390              1395

Val Asn Ile Asn Ile Gly Pro   Gly Asp Cys Glu Trp   Phe Ala Val
    1400              1405              1410

His Glu His Tyr Trp Glu Thr   Ile Ser Ala Phe Cys   Asp Arg His
    1415              1420              1425

Gly Val Asp Tyr Leu Thr Gly   Ser Trp Trp Pro Ile   Leu Asp Asp
    1430              1435              1440

Leu Tyr Ala Ser Asn Ile Pro   Val Tyr Arg Phe Val   Gln Arg Pro
    1445              1450              1455

Gly Asp Leu Val Trp Ile Asn   Ala Gly Thr Val His   Trp Val Gln
    1460              1465              1470

Ala Thr Gly Trp Cys Asn Asn   Ile Ala Trp Asn Val   Gly Pro Leu
    1475              1480              1485

Thr Ala Tyr Gln Tyr Gln Leu   Ala Leu Glu Arg Tyr   Glu Trp Asn
    1490              1495              1500

Glu Val Lys Asn Val Lys Ser   Ile Val Pro Met Ile   His Val Ser
    1505              1510              1515

Trp Asn Val Ala Arg Thr Val   Lys Ile Ser Asp Pro   Asp Leu Phe
    1520              1525              1530

Lys Met Ile Lys Phe Cys Leu   Leu Gln Ser Met Lys   His Cys Gln
    1535              1540              1545

Val Gln Arg Glu Ser Leu Val   Arg Ala Gly Lys Lys   Ile Ala Tyr
    1550              1555              1560

Gln Gly Arg Val Lys Asp Glu   Pro Ala Tyr Tyr Cys   Asn Glu Cys
    1565              1570              1575
```

-continued

```
Asp Val Glu Val Phe Asn Ile  Leu Phe Val Thr Ser  Glu Asn Gly
    1580              1585              1590

Ser Arg Asn Thr Tyr Leu Val  His Cys Glu Gly Cys  Ala Arg Arg
    1595              1600              1605

Arg Ser Ala Gly Leu Gln Gly  Val Val Val Leu Glu  Gln Tyr Arg
    1610              1615              1620

Thr Glu Glu Leu Ala Gln Ala  Tyr Asp Ala Phe Thr  Leu Ala Pro
    1625              1630              1635

Ala Ser Thr Ser Arg
    1640

<210> SEQ ID NO 3
<211> LENGTH: 6731
<212> TYPE: DNA
<213> ORGANISM: Homo sapiens

<400> SEQUENCE: 3
ggcaacatgc cagccccgta gcactgccca ccccacccac tgtggtctgt tgtaccccac      60
tgctggggtg gtggttccaa tgagacaggg cacaccaaac tccatctggc tgttactgag     120
gcggagacac gggtgatgat tggctttctg gggagagagg aagtcctgtg attggccaga     180
tctctggagc ttgccgacgc ggtgtgagga cgctcccacg gaggccggaa ttggctgtga     240
aaggactgag gcagccatct gggggtagcc ggcactctta tcagagcggc tggagccgga     300
ccatcgtccc agagagctgg ggcaggggc cgtgcccaat ctccagggct cctggggcca     360
ctgctgacct ggctggatgc atcgggcagt ggaccctcca ggggcccgcg ctgcacggga     420
agcctttgcc cttggggggcc tgagctgtgc tggggcctgg agctcctgcc cgcctcatcc     480
ccctcctcgt agcgcatggc tgcctggagg cagatgctca gccagcattg ggcagccccc     540
gcttcctgct cccctacccc cttcacatgg cagtagttct gggcacccca gcaaaccata     600
ttatgctcca ggggcgccca ctccaagacc cctccatggg aagctggaat ccctgcatgg     660
ctgtgtgcag gcattgctcc gggagccagc ccagccaggg ctttgggaac agcttgggca     720
actgtacgag tcagagcacg atagtgagga ggccacacgc tgctaccaca gcgcccttcg     780
atacggagga agcttcgctg agctgggggcc ccgcattggc cgactgcagc aggcccagct     840
ctggaacttt catactggct cctgccagca ccgagccaag gtcctgcccc cactggagca     900 agtgtgggaac ttgctacacc ttgagcacaa acggaactat ggagccaagc ggggaggtcc     960
cccggtgaag cgagctgctg aaccccccagt ggtgcagcct gtgcctcctg cagcactctc    1020
aggcccctca ggggaggagg gcctcagccc tggaggcaag cgaaggagag ctgcaactc    1080 tgaacagact ggccttcccc cagggctgcc actgcctcca ccaccattac caccaccacc    1140
accaccacca ccaccaccac caccacccct gcctggcctg gctaccagcc ccccatttca    1200
gctaaccaag ccagggctgt ggagtaccct gcatggagat gcctggggcc cagagcgcaa    1260
gggttcagca cccccagagc gccaggagca gcggcactcg ctgcctcacc catatccata    1320
cccagctcca gcgtacaccg cgcacccccc tggccaccgg ctggtcccgg ctgctccccc    1380
aggcccaggc ccccgccccc caggagcaga gagccatggc tgcctgcctg ccacccgtcc    1440 cccccggaagt gaccttagag agagcagagt tcagaggtcg cggatggact ccagcgtttc    1500
accagcagca accaccgcct gcgtgcctta cgcccctttcc cggccccctg gcctccccgg    1560
caccaccacc agcagcagca gtagcagcag cagcaacact ggtctccggg gcgtggagcc    1620
gaacccaggc attcccggcg ctgaccatta ccaaactccc gcgctggagg tctctcacca    1680
```

-continued

```
tggccgcctg gggccctcgg cacacagcag tcggaaaccg ttcttggggg ctcccgctgc    1740
cactccccac ctatccctgc cacctggacc ttcctcaccc cctccacccc cctgtccccg    1800
cctcttacgc cccccaccac cccctgcctg gttgaagggt ccggcctgcc gggcagcccg    1860
agaggatgga gagatcttag aagagctctt ctttgggact gagggacccc cccgccctgc    1920
cccaccaccc ctcccccatc gcgagggctt cttggggcct ccggcctccc gcttttctgt    1980
gggcactcag gattctcaca cccctcccac tcccccaacc ccaaccacca gcagtagcaa    2040
cagcaacagt ggcagccaca gcagcagccc tgctgggcct gtgtcctttc ccccaccacc    2100
ctatctggcc agaagtatag acccccttcc ccggcctccc agcccagcac agaaccccca    2160
ggacccacct cttgtacccc tgactcttgc cctgcctcca gcccctcctt cctcctgcca    2220
ccaaaatacc tcaggaagct tcaggcgccc ggagagcccc cggcccaggg tctccttccc    2280 aaagacccc gaggtggggc cggggccacc cccaggcccc ctgagtaaag cccccagcc     2340 tgtgccgccc ggggttgggg agctgcctgc ccgaggccct cgactctttg attttccccc    2400
cactccgctg gaggaccagt ttgaggagcc agccgaattc aagatcctac ctgatgggct    2460
ggccaacatc atgaagatgc tggacgaatc cattcgcaag gaagaggaac agcaacaaca    2520
cgaagcaggc gtggcccccc aaccccgct gaaggagccc tttgcatctc tgcagtctcc     2580
tttccccacc gacacagccc ccaccactac tgctcctgct gtcgccgtca ccaccaccac    2640
caccaccacc accaccacca cggccaccca ggaagaggag aagaagccac caccagccct    2700
accaccacca ccgcctctag ccaagttccc tccaccctct cagccacagc caccaccacc    2760 cccaccccc agcccggcca gctgctcaa atccttggcc tccgtgctgg agggacaaaa      2820
gtactgttat cggggggactg gagcagctgt ttccacccgg cctgggccct gcccaccac    2880 tcagtattcc cctggccccc catcaggtgc taccgccctg ccgcccacct cagcggcccc    2940
tagcgcccag ggctccccac agccctctgc ttcctcgtca tctcagttct ctacctcagg    3000
cgggccctgg gcccgggagc gcagggcggg cgaagagcca gtcccgggcc ccatgacccc    3060
cacccaaccg cccccacccc tatctctgcc ccctgctcgc tctgagtctg aggtgctaga    3120
agagatcagc cgggcttgcg agacccttgt ggagcgggtg ggccggagtg ccactgaccc    3180
agccgaccca gtggacacag cagagccagc ggacagtggg actgagcgac tgctgccccc    3240
cgcacaggcc aaggaggagg ctggcgggt ggcggcagtg tcaggcagct gtaagcggcg      3300
acagaaggag catcagaagg agcatcggcg gcacaggcgg gcctgtaagg acagtgtggg    3360
tcgtcggccc cgtgagggca gggcaaaggc caaggccaag gtccccaaag aaaagagccg    3420
ccgggtgctg gggaacctgg acctgcagag cgaggagatc cagggtcgtg agaagtcccg    3480
gcccgatctt ggcggggcct ccaaggccaa gccacccaca gctccagccc ctccatcagc    3540
tcctgcacct tctgcccagc ccacaccccc gtcagcctct gtccctggaa agaaggctcg    3600
ggaggaagcc ccagggccac cgggtgtcag ccgggccgac atgctgaagc tgcgctcact    3660
tagtgagggg cccccccaagg agctgaagat ccggctcatc aaggtagaga gtggtgacaa    3720
ggagaccttt atcgcctctg aggtggaaga gcggcggctg cgcatggcag acctcaccat    3780
cagccactgt gctgctgacg tcgtgcgcgc cagcaggaat gccaaggtga agggaagtt     3840 tcgagagtcc tacctttccc ctgcccagtc tgtgaaaccg aagatcaaca ctgaggagaa    3900
gctgccccgg gaaaaaactca acccccctac acccagcatc tatctggaga gcaaacggga    3960
tgccttctca cctgtcctgc tgcagttctg tacagaccct cgaaatccca tcacagtgat    4020
ccggggcctg gcgggctccc tgcggctcaa cttgggcctc ttctccacca agaccctggt    4080
```

-continued

```
ggaagcgagt ggcgaacaca ccgtggaagt tcgcacccag gtgcagcagc cctcagatga    4140
gaactgggat ctgacaggca ctcggcagat ctggccttgt gagagctccc gttcccacac    4200
caccattgcc aagtacgcac agtaccaggc ctcatccttc caggagtctc tgcaggagga    4260
gaaggagagt gaggatgagg agtcagagga gccagacagc accactggaa cccctcctag    4320
cagcgcacca gacccgaaga accatcacat catcaagttt ggcaccaaca tcgacttgtc    4380
tgatgctaag cggtggaagc cccagctgca ggagctgctg aagctgcccg ccttcatgcg    4440
ggtaacatcc acgggcaaca tgctgagcca cgtgggccac accatcctgg gcatgaacac    4500
ggtgcagctg tacatgaagg tgcccggcag ccgaacgcca ggccaccagg agaataacaa    4560
cttctgctcc gtcaacatca acattggccc aggcgactgc gagtggttcg cggtgcacga    4620
gcactactgg gagaccatca gcgctttctg tgatcggcac ggcgtggact acttgacggg    4680
ttcctggtgg ccaatcctgg atgatctcta tgcatccaat attcctgtgt accgcttcgt    4740
gcagcgaccc ggagacctcg tgtggattaa tgcggggact gtgcactggg tgcaggccac    4800
cggctggtgc aacaacattg cctggaacgt ggggcccctc accgcctatc agtaccagct    4860
ggccctggaa cgatacgagt ggaatgaggt gaagaacgtc aaatccatcg tgcccatgat    4920
tcacgtgtca tggaacgtgg ctcgcacggt caaaatcagc gaccccgact tgttcaagat    4980
gatcaagttc tgcctgctgc agtccatgaa gcactgccag gtgcaacgcg agagcctggt    5040
gcgggcaggg aagaaaatcg cttaccaggg ccgtgtcaag gacgagccag cctactactg    5100
caacgagtgc gatgtggagg tgtttaacat cctgttcgtg acaagtgaga atggcagccg    5160
caacacgtac ctggtacact gcgagggctg tgcccggcgc cgcagcgcag gcctgcaggg    5220
cgtggtggtg ctggagcagt accgcactga ggagctggct caggcctacg acgccttcac    5280
gctggtgagg gcccggcggg cgcgcgggca gcggaggagg gcactggggc aggctgcagg    5340
gacgggcttc gggagcccgg ccgcgccttt ccctgagccc ccgccggctt tctccccca     5400 ggccccagcc agcacgtcgc gatgaggccg gacgccccgc ccgcctgcct gcccgcgcaa    5460
ggcgccgcgg ggccaccagc acatgcctgg gctggaccta ggtcccgcct gtggccgaga    5520 aggggtcgg gcccagccct tccaccccat tggcagctcc cctcacttaa tttattaaga    5580
aaaacttttt tttttttttt agcaaatatg aggaaaaaag gaaaaaaaat gggagacggg    5640 ggaggggct ggcagcccct cgcccaccag cgcctcccct caccgacttt ggcctttta     5700 gcaacagaca caaggaccag gctccggcgg cggcggggt cacatacggg ttccctcacc     5760
ctgccagccc cccgcccgcc cggcgcagat gcacgcggct cgtgtatgta catagacgtt    5820
acggcagccg aggtttttaa tgagattctt tctatgggct ttaccccctcc cccggaacct   5880 cctttttac ttccaatgct agctgtgacc cctgtacatg tctctttatt cacttggtta     5940
tgatttgtat tttttgttct tttcttgttt ttttgttttt aatttataac agtcccactc    6000
acctctattt attcattttt gggaaaaccc gacctccac accccaagc catcctgccc      6060 gcccctccag ggaccgcccg tcgccgggct ctccccgcgc cccagtgtgt gtccgggccc    6120
ggcccgaccg tctccacccg tccgcccgcg gctccagccg ggttctcatg gtgctcaaac    6180
ccgctcccct ccctacgtc ctgcactttc tcggaccagt ccccccactc ccgacccgac     6240
cccagcccca cctgagggtg agcaactcct gtactgtagg ggaagaagtg ggaactgaaa    6300
tggtattttg taaaaaaaat aaataaaata aaaaaattaa aggttttaaa gaaagaacta    6360
tgaggaaaag gaaccccgtc cttcccagcc ccggccaact ttaaaaaaca cagaccttca    6420
```

-continued

```
cccccacccc ctttttcttt taagtgtgaa acaacccagg gccagggcct cactggggca      6480
gggacacccc ggggtgagtt tctctggggc tttatttttcg ttttgttggt tgttttttct      6540
ccacgctggg gctgcggagg ggtggggggt ttacagtccc gcaccctcgc actgcactgt      6600
ctctctgccc caggggcaga ggggtcttcc caaccctacc cctatttttcg gtgattttttg      6660 tgtgagaata ttaatattaa aaataaacgg agaaaaaaaa aaaaaaaaaa aaaaaaaaaa      6720
aaaaaaaaaa a                                                          6731
```

<210> SEQ ID NO 4
<211> LENGTH: 1347
<212> TYPE: PRT
<213> ORGANISM: Homo sapiens

<400> SEQUENCE: 4

```
Met Lys Ser Cys Ala Val Ser Leu Thr Thr Ala Ala Val Ala Phe Gly
1               5                   10                  15

Asp Glu Ala Lys Lys Met Ala Glu Gly Lys Ala Ser Arg Glu Ser Glu
            20                  25                  30

Glu Glu Ser Val Ser Leu Thr Val Glu Glu Arg Glu Ala Leu Gly Gly
        35                  40                  45

Met Asp Ser Arg Leu Phe Gly Phe Val Arg Leu His Glu Asp Gly Ala
    50                  55                  60

Arg Thr Lys Thr Leu Leu Gly Lys Ala Val Arg Cys Tyr Glu Ser Leu
65                  70                  75                  80

Ile Leu Lys Ala Glu Gly Lys Val Glu Ser Asp Phe Phe Cys Gln Leu
                85                  90                  95

Gly His Phe Asn Leu Leu Leu Glu Asp Tyr Ser Lys Ala Leu Ser Ala
            100                 105                 110

Tyr Gln Arg Tyr Tyr Ser Leu Gln Ala Asp Tyr Trp Lys Asn Ala Ala
            115                 120                 125

Phe Leu Tyr Gly Leu Gly Leu Val Tyr Phe Tyr Tyr Asn Ala Phe His
    130                 135                 140

Trp Ala Ile Lys Ala Phe Gln Asp Val Leu Tyr Val Asp Pro Ser Phe
145                 150                 155                 160

Cys Arg Ala Lys Glu Ile His Leu Arg Leu Gly Leu Met Phe Lys Val
                165                 170                 175

Asn Thr Asp Tyr Lys Ser Ser Leu Lys His Phe Gln Leu Ala Leu Ile
            180                 185                 190

Asp Cys Asn Pro Cys Thr Leu Ser Asn Ala Glu Ile Gln Phe His Ile
            195                 200                 205

Ala His Leu Tyr Glu Thr Gln Arg Lys Tyr His Ser Ala Lys Glu Ala
    210                 215                 220

Tyr Glu Gln Leu Leu Gln Thr Glu Asn Leu Pro Ala Gln Val Lys Ala
225                 230                 235                 240

Thr Val Leu Gln Gln Leu Gly Trp Met His His Asn Met Asp Leu Val
                245                 250                 255

Gly Asp Lys Ala Thr Lys Glu Ser Tyr Ala Ile Gln Tyr Leu Gln Lys
            260                 265                 270

Ser Leu Glu Ala Asp Pro Asn Ser Gly Gln Ser Trp Tyr Phe Leu Gly
            275                 280                 285

Arg Cys Tyr Ser Ser Ile Gly Lys Val Gln Asp Ala Phe Ile Ser Tyr
    290                 295                 300

Arg Gln Ser Ile Asp Lys Ser Glu Ala Ser Ala Asp Thr Trp Cys Ser
305                 310                 315                 320
```

-continued

```
Ile Gly Val Leu Tyr Gln Gln Gln Asn Gln Pro Met Asp Ala Leu Gln
                325             330             335

Ala Tyr Ile Cys Ala Val Gln Leu Asp His Gly His Ala Ala Ala Trp
                340             345             350

Met Asp Leu Gly Thr Leu Tyr Glu Ser Cys Asn Gln Pro Gln Asp Ala
        355             360             365

Ile Lys Cys Tyr Leu Asn Ala Ala Arg Ser Lys Arg Cys Ser Asn Thr
    370             375             380

Ser Thr Leu Ala Ala Arg Ile Lys Phe Leu Gln Asn Gly Ser Asp Asn
385             390             395             400

Trp Asn Gly Gly Gln Ser Leu Ser His His Pro Val Gln Gln Val Tyr
                405             410             415

Ser Leu Cys Leu Thr Pro Gln Lys Leu Gln His Leu Glu Gln Leu Arg
                420             425             430

Ala Asn Arg Asp Asn Leu Asn Pro Ala Gln Lys His Gln Leu Glu Gln
            435             440             445

Leu Glu Ser Gln Phe Val Leu Met Gln Gln Met Arg His Lys Glu Val
    450             455             460

Ala Gln Val Arg Thr Thr Gly Ile His Asn Gly Ala Ile Thr Asp Ser
465             470             475             480

Ser Leu Pro Thr Asn Ser Val Ser Asn Arg Gln Pro His Gly Ala Leu
            485             490             495

Thr Arg Val Ser Ser Val Ser Gln Pro Gly Val Arg Pro Ala Cys Val
            500             505             510

Glu Lys Leu Leu Ser Ser Gly Ala Phe Ser Ala Gly Cys Ile Pro Cys
        515             520             525

Gly Thr Ser Lys Ile Leu Gly Ser Thr Asp Thr Ile Leu Leu Gly Ser
    530             535             540

Asn Cys Ile Ala Gly Ser Glu Ser Asn Gly Asn Val Pro Tyr Leu Gln
545             550             555             560

Gln Asn Thr His Thr Leu Pro His Asn His Thr Asp Leu Asn Ser Ser
            565             570             575

Thr Glu Glu Pro Trp Arg Lys Gln Leu Ser Asn Ser Ala Gln Gly Leu
        580             585             590

His Lys Ser Gln Ser Ser Cys Leu Ser Gly Pro Asn Glu Glu Gln Pro
        595             600             605

Leu Phe Ser Thr Gly Ser Ala Gln Tyr His Gln Ala Thr Ser Thr Gly
    610             615             620

Ile Lys Lys Ala Asn Glu His Leu Thr Leu Pro Ser Asn Ser Val Pro
625             630             635             640

Gln Gly Asp Ala Asp Ser His Leu Ser Cys His Thr Ala Thr Ser Gly
            645             650             655

Gly Gln Gln Gly Ile Met Phe Thr Lys Glu Ser Lys Pro Ser Lys Asn
            660             665             670

Arg Ser Leu Val Pro Glu Thr Ser Arg His Thr Gly Asp Thr Ser Asn
        675             680             685

Gly Cys Ala Asp Val Lys Gly Leu Ser Asn His Val His Gln Leu Ile
    690             695             700

Ala Asp Ala Val Ser Ser Pro Asn His Gly Asp Ser Pro Asn Leu Leu
705             710             715             720

Ile Ala Asp Asn Pro Gln Leu Ser Ala Leu Leu Ile Gly Lys Ala Asn
            725             730             735
```

-continued

Gly Asn Val Gly Thr Gly Thr Cys Asp Lys Val Asn Asn Ile His Pro
                740               745                750

Ala Val His Thr Lys Thr Asp His Ser Val Ala Ser Ser Pro Ser Ser
            755               760               765

Ala Ile Ser Thr Ala Thr Pro Ser Pro Lys Ser Thr Glu Gln Arg Ser
    770               775               780

Ile Asn Ser Val Thr Ser Leu Asn Ser Pro His Ser Gly Leu His Thr
785               790               795               800

Val Asn Gly Glu Gly Leu Gly Lys Ser Gln Ser Ser Thr Lys Val Asp
                805               810               815

Leu Pro Leu Ala Ser His Arg Ser Thr Ser Gln Ile Leu Pro Ser Met
            820               825               830

Ser Val Ser Ile Cys Pro Ser Ser Thr Glu Val Leu Lys Ala Cys Arg
            835               840               845

Asn Pro Gly Lys Asn Gly Leu Ser Asn Ser Cys Ile Leu Leu Asp Lys
    850               855               860

Cys Pro Pro Pro Arg Pro Pro Thr Ser Pro Tyr Pro Pro Leu Pro Lys
865               870               875               880

Asp Lys Leu Asn Pro Pro Thr Pro Ser Ile Tyr Leu Glu Asn Lys Arg
                885               890               895

Asp Ala Phe Phe Pro Pro Leu His Gln Phe Cys Thr Asn Pro Lys Asn
                900               905               910

Pro Val Thr Val Ile Arg Gly Leu Ala Gly Ala Leu Lys Leu Asp Leu
                915               920               925

Gly Leu Phe Ser Thr Lys Thr Leu Val Glu Ala Asn Asn Glu His Met
    930               935               940

Val Glu Val Arg Thr Gln Leu Leu Gln Pro Ala Asp Glu Asn Trp Asp
945               950               955               960

Pro Thr Gly Thr Lys Lys Ile Trp Arg Cys Glu Ser Asn Arg Ser His
                965               970               975

Thr Thr Ile Ala Lys Tyr Ala Gln Tyr Gln Ala Ser Ser Phe Gln Glu
            980               985               990

Ser Leu Arg Glu Glu Asn Glu Lys  Arg Thr Gln His Lys  Asp His Ser
    995               1000               1005

Asp Asn  Glu Ser Thr Ser Ser  Glu Asn Ser Gly Arg  Arg Arg Lys
    1010               1015               1020

Gly Pro  Phe Lys Thr Ile Lys  Phe Gly Thr Asn Ile  Asp Leu Ser
    1025               1030               1035

Asp Asn  Lys Lys Trp Lys Leu  Gln Leu His Glu Leu  Thr Lys Leu
    1040               1045               1050

Pro Ala  Phe Ala Arg Val Val  Ser Ala Gly Asn Leu  Leu Thr His
    1055               1060               1065

Val Gly  His Thr Ile Leu Gly  Met Asn Thr Val Gln  Leu Tyr Met
    1070               1075               1080

Lys Val  Pro Gly Ser Arg Thr  Pro Gly His Gln Glu  Asn Asn Asn
    1085               1090               1095

Phe Cys  Ser Val Asn Ile Asn  Ile Gly Pro Gly Asp  Cys Glu Trp
    1100               1105               1110

Phe Val  Val Pro Glu Asp Tyr  Trp Gly Val Leu Asn  Asp Phe Cys
    1115               1120               1125

Glu Lys  Asn Asn Leu Asn Phe  Leu Met Ser Ser Trp  Trp Pro Asn
    1130               1135               1140

-continued

```
Leu Glu  Asp Leu Tyr Glu Ala  Asn Val Pro Val Tyr  Arg Phe Ile
    1145             1150             1155

Gln Arg  Pro Gly Asp Leu Val  Trp Ile Asn Ala Gly  Thr Val His
    1160             1165             1170

Trp Val  Gln Ala Val Gly Trp  Cys Asn Asn Ile Ala  Trp Asn Val
    1175             1180             1185

Gly Pro  Leu Thr Ala Cys Gln  Tyr Lys Leu Ala Val  Glu Arg Tyr
    1190             1195             1200

Glu Trp  Asn Lys Leu Lys Ser  Val Lys Ser Pro Val  Pro Met Val
    1205             1210             1215

His Leu  Ser Trp Asn Met Ala  Arg Asn Ile Lys Val  Ser Asp Pro
    1220             1225             1230

Lys Leu  Phe Glu Met Ile Lys  Tyr Cys Leu Leu Lys  Ile Leu Lys
    1235             1240             1245

Gln Tyr  Gln Thr Leu Arg Glu  Ala Leu Val Ala Ala  Gly Lys Glu
    1250             1255             1260

Val Ile  Trp His Gly Arg Thr  Asn Asp Glu Pro Ala  His Tyr Cys
    1265             1270             1275

Ser Ile  Cys Glu Val Glu Val  Phe Asn Leu Leu Phe  Val Thr Asn
    1280             1285             1290

Glu Ser  Asn Thr Gln Lys Thr  Tyr Ile Val His Cys  His Asp Cys
    1295             1300             1305

Ala Arg  Lys Thr Ser Lys Ser  Leu Glu Asn Phe Val  Val Leu Glu
    1310             1315             1320

Gln Tyr  Lys Met Glu Asp Leu  Ile Gln Val Tyr Asp  Gln Phe Thr
    1325             1330             1335

Leu Ala  Leu Ser Leu Ser Ser  Ser Ser
    1340             1345

<210> SEQ ID NO 5
<211> LENGTH: 6817
<212> TYPE: DNA
<213> ORGANISM: Homo sapiens

<400> SEQUENCE: 5
gctcatcgtt tgttgtttag ataatatcat gaactgataa atgcagttgc cacgttgatt      60
ccctagggcc tggcttaccg actgaggtca taagatatta tgccttctct ttagacttgg     120
tcagtggaga ggaaatgggc aaagaaccag cctatggagg tgacaaggcc ttagggccaa     180
aagtcttgag ggtgaaggtt tagggcctgc gcagcttccc tgccatgccc cgcaaggtct     240
cgcattcgca aggcttgtga cagtgggagc tccattacgg actctcctaa agtccatggt     300
gtcctctttt cgcatttgcg ccccgtgggt gatgcccgat gccgcccttc ccatcgctct     360 cttcccctc aagcgtatcg caactgcaaa aacacccagc acagacactc cattttctat      420
cttaatgcat ttaactagca caacctacag gttgttccat cccagagact acccttttct     480
ccatagacgt gaccatcaac caaccagcgg tcagaatcag tcagcctctg tcatgttcct     540
aggtccttgg cgaactggct gggcggggtc ccagcagcct aggagtacag tggagcaatg     600
cctgacgtaa gtcaacaaag atcacgtgag acgaatcagt cgcctagatt ggctacaact     660
aagtggttgg gagcggggag gtcgcggcgg ctgcgtgggg ttcgcccgtg acacaattac     720
aactttgtgc tggtgctggc aaagtttgtg attttaagaa attctgctgt gctctccagc     780
actgcgagct tctgccttcc ctgtagtttc ccagatgtga tccaggtagc cgagttccgc     840
```

-continued

```
tgcccgtgct tcggtagctt aagtctttgc ctcagctttt ttccttgcag ccgctgagga    900
ggcgataaaa ttggcgtcac agtctcaagc agcgattgaa ggcgtctttt caactactcg    960
attaaggttg ggtatcgtcg tgggacttgg aaatttgttg tttccatgaa atcctgcgca   1020
gtgtcgctca ctaccgccgc tgttgccttc ggtgatgagg caaagaaaat ggcggaagga   1080
aaagcgagcc gcgagagtga agaggagtct gttagcctga cagtcgagga aagggaggcg   1140
cttggtggca tggacagccg tctcttcggg ttcgtgaggc ttcatgaaga tggcgccaga   1200
acgaagaccc tactaggcaa ggctgttcgc tgctacgaat ctttaatctt aaaagctgaa   1260
ggaaaagtgg agtctgactt cttttgccaa ttaggtcact tcaacctctt gttggaagat   1320
tattcaaaag cattatctgc atatcagaga tattacagtt tacaggctga ctactggaag   1380
aatgctgcgt tttttatatgg ccttggtttg gtctacttct actacaatgc atttcattgg   1440
gcaattaaag catttcaaga tgtcctttat gttgacccca gcttttgtcg agccaaggaa   1500
attcatttac gacttgggct catgttcaaa gtgaacacag actacaagtc tagtttaaag   1560
cattttcagt tagccttgat tgactgtaat ccatgtactt tgtccaatgc tgaaattcaa   1620
tttcatattg cccatttgta tgaaacccag aggaagtatc attctgcaaa ggaggcatat   1680
gaacaacttt tgcagacaga aaaccttcct gcacaagtaa aagcaactgt attgcaacag   1740
ttaggttgga tgcatcataa tatggatcta gtaggagaca aagccacaaa ggaaagctat   1800
gctattcagt atctccaaaa gtctttggag gcagatccta attctggcca atcgtggtat   1860
tttcttggaa ggtgttattc aagtattggg aaagttcagg atgcctttat atcttacagg   1920
caatctattg ataaatcaga agcaagtgca gatacatggt gttcaatagg tgtgttgtat   1980
cagcagcaaa atcagcctat ggatgcttta caggcatata tttgtgctgt acaattggac   2040
catgggcatg ccgcagcctg gatggaccta ggtactctct atgaatcctg caatcaacct   2100
caagatgcca ttaaatgcta cctaaatgca gctagaagca aacgttgtag taatacctct   2160
acgcttgctg caagaattaa atttctacag gctcagttgt gtaaccttcc acaaagtagt   2220
ctacagaata aaactaaatt acttcctagt attgaggagg catggagcct accaatcccc   2280
gcagagctta cctccaggca gggtgccatg aacacagcac agcaggctta tagagctcat   2340
gatccaaata ctgaacatgt attaaaccac agtcaaacac caattttaca gcaatccttg   2400
tcactacaca tgattacttc tagccaagta gaaggcctgt ccagtcctgc caagaagaaa   2460
agaacatcta gtccaacaaa gaatggttct gataactgga atggtggcca gagtctttca   2520
catcatccag tacagcaagt ttattcgttg tgtttgacac cacagaaatt acagcacttg   2580
gaacaactgc gagcaaatag agataattta aatccagcac agaagcatca gctggaacag   2640
ttagaaagtc agtttgtctt aatgcagcaa atgagacaca aagaagttgc tcaggtacga   2700
actactggaa ttcataacgg ggccataact gattcatcac tgcctacaaa ctctgtctct   2760
aatcgacaac cacatggtgc tctgaccaga gtatctagcg tctctcagcc tggagttcgc   2820
cctgcttgtg ttgaaaaact tttgtccagt ggagcttttt ctgcaggctg tattccttgt   2880
ggcacatcaa aaattctagg aagtacagac actatcttgc taggcagtaa ttgtatagca   2940
ggaagtgaaa gtaatggaaa tgtgccttac ctgcagcaaa atacacacac tctacctcat   3000
aatcatacag acctgaacag cagcacagaa gagccatgga gaaaacagct atctaactcc   3060
gctcaggggc ttcataaaag tcagagttca tgtttgtcag acctaatga agaacaacct   3120 ctgttttcca ctgggtcagc ccagtatcac caggcaacta gcactggtat taagaaggcg   3180
aatgaacatc tcactctgcc tagtaattca gtaccacagg gggatgctga cagtcacctc   3240
```

```
tcctgtcata ctgctacctc aggtggacaa caaggcatta tgtttaccaa agagagcaag    3300
ccttcaaaaa atagatcctt ggtgcctgaa acaagcaggc atactggaga cacatctaat    3360
ggctgtgctg atgtcaaggg actttctaat catgttcatc agttgatagc agatgctgtt    3420
tccagtccta accatggaga ttcaccaaat ttattaattg cagacaatcc tcagctctct    3480
gctttgttga ttggaaaagc caatggcaat gtgggtactg gaacctgtga caaagtgaat    3540
aatattcacc cagctgttca tacaaagact gatcattctg ttgcctcttc accctcttca    3600
gccatttcca cagcaacacc ttctcctaaa tccactgagc agagaagcat aaacagtgtt    3660
accagcctta acagtcctca cagtggatta cacacagtca atggagaggg gctggggaag    3720
tcacagagct ctacaaaagt agacctgcct ttagctagcc acagatctac ttctcagatc    3780
ttaccatcaa tgtcagtgtc tatatgcccc agttcaacag aagttctgaa agcatgcagg    3840
aatccaggta aaaatggctt gtctaatagc tgcattttgt tagataaatg tccacctcca    3900
agaccaccaa cttcaccata cccacccttg ccaaaggaca agttgaatcc acccacacct    3960
agtatttact tggaaaataa acgtgatgct ttctttcctc cattacatca attttgtaca    4020
aatccaaaaa accctgttac agtaatacgt ggccttgctg gagctcttaa attagatctt    4080
ggacttttct ctaccaaaac tttggtagaa gctaacaatg aacatatggt agaagtgagg    4140
acacagttgc tgcaaccagc agatgaaaac tgggatccca ctggaacaaa gaaaatctgg    4200
cgttgtgaaa gcaatagatc tcatactaca attgccaaat acgcacaata ccaggcttcc    4260
tccttccagg aatcattgag agaagaaaat gagaaaagaa cacaacacaa agatcattca    4320
gataacgaat ccacatcttc agagaattct ggaaggagaa ggaaaggacc ttttaaaacc    4380
ataaaatttg ggaccaacat tgacctctct gataacaaaa agtggaagtt gcagttacat    4440
gaactgacta aacttcctgc ttttgcgcgt gtggtgtcag caggaaatct tctaacccat    4500
gttgggcata ccattctggg catgaataca gtacaactgt atatgaaagt tccagggagt    4560
cggacaccag gtcaccaaga aaataacaac ttctgctctg ttaacataaa tattggtcca    4620
ggagattgtg aatggtttgt tgtacctgaa gattattggg gtgttctgaa tgacttctgt    4680
gaaaaaaata atttgaattt tttaatgagt tcttggtggc ccaaccttga agatctttat    4740
gaagcaaatg tccctgtgta tagatttatt cagcgacctg agatttggt ctggataaat    4800 gcaggcactg tgcattgggt tcaagctgtt ggctggtgca ataacattgc ctggaatgtt    4860
ggtccactta cagcctgcca gtataaattg gcagtggaac ggtatgaatg gaacaaattg    4920
aaaagtgtga agtcaccagt acccatggtg catctttcct ggaatatggc acgaaatatc    4980
aaagtctcag atccaaagct ttttgaaatg attaagtatt gtcttttgaa aattctgaag    5040
caatatcaga cattgagaga agctcttgtt gcagcaggaa aagaggttat atggcatggg    5100
cggacaaatg atgaaccagc tcattactgt agcatttgtg aggtggaggt ttttaatctg    5160
ctttttgtca ctaatgaaag caatactcaa aaaacctaca tagtacattg ccatgattgt    5220
gcacgaaaaa caagcaaaag tttggaaaat tttgtggtgc tcgaacagta caaaatggag    5280
gacctaatcc aagtttatga tcaatttaca ctagctcttt cattatcatc ctcatcttga    5340
tatagttcca tgaatattaa atgagattat ttctgctctt caggaaattt ctgcaccact    5400
ggttttgtag ctgtttcata aaactgttga ctaaaagcta tgtctatgca accttccaag    5460
aatagtatgt caagcaactg gacacagtgc tgcctctgct tcaggactta acatgctgat    5520
ccagctgtac ttcagaaaaa taatattaat catatgtttt gtgtacgtat gacaaactgt    5580
```

-continued

```
caaagtgaca cagaatactg atttgaagat agcctttttt atgtttctct atttctgggc      5640
tgatgaatta atattcattt gtattttaac cctgcagaat tttccttagt taaaaacact      5700
ttcctagctg gtcatttctt cataagatag caaatttaaa tctctcctcg atcagctttt      5760
aaaaaatgtg tactattatc tgaggaagtt ttttactgct ttatgttttt gtgtgttttg      5820
aggccatgat gattacattt gtggttccaa aataattttt ttaaatatta atagcccata      5880
tacaaagata atggattgca catagacaaa gaaataaact tcagatttgt gatttttgtt      5940
tctaaacttg atacagattt acactattta taaatacgta tttattgcct gaaaatattt      6000
gtgaatggaa tgttgttttt ttccagacgt aactgccatt aaatactaag gagttctgta      6060
gttttaaaca ctactcctat tacattttat atgtgtagat aaaactgctt agtattatac      6120
agaaattttt attaaaattg ttaaatgttt aaagggtttc ccaatgtttg agtttaaaaa      6180
agactttctg aaaaaatcca cttttttgttc attttcaaac ctaatgatta tatgtatttt      6240
atatgtgtgt gtatgtgtac acacatgtat aatatataca gaaacctcga tatataattg      6300
tatagatttt aaaagtttta ttttttacat ctatggtagt ttttgaggtg cctattataa      6360
agtattacgg aagtttgctg tttttaaagt aaatgtcttt tagtgtgatt tattaagttg      6420
tagtcaccat agtgatagcc cataaataat tgctggaaaa ttgtatttta taacagtaga      6480
aaacatatag tcagtgaagt aaatattttta aaggaaacat tatatagatt tgataaatgt      6540
tgtttataat taagagtttc ttatggaaaa gagattcaga atgataacct cttttagaga      6600
acaaataagt gacttatttt tttaaagcta gatgactttg aaatgctata ctgtcctgct      6660
tgtacaacat ggtttggggt gaaggggagg aaagtattaa aaaatctata tcgctagtaa      6720
attgtaataa gttctattaa aacttgtatt tcatatgaaa aatttgctaa tttaatatta      6780
actcatttga taataatact tgtcttttct acctctc                              6817
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
ttgacggaag ggcaccacca g                                                21
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
gcaccaccac ccacggaatc g                                                21
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 8
tttgtcgcag ggcagtctta                                              20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtttgcccat cactattcca gc                                           22
```